(12) United States Patent
Schinazi et al.

(10) Patent No.: US 11,629,125 B2
(45) Date of Patent: Apr. 18, 2023

(54) ELIMINATION OF HEPATITIS B VIRUS WITH ANTIVIRAL AGENTS

(71) Applicant: Emory University, Atlanta, GA (US)

(72) Inventors: Raymond F. Schinazi, Miami, FL (US); Sebastien Boucle, Smyrna, GA (US); Franck Amblard, Atlanta, GA (US); Ozkan Sari, Decatur, GA (US); Leda Bassit, Smyrna, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 16/998,944

(22) Filed: Aug. 20, 2020

(65) Prior Publication Data

US 2021/0114981 A1 Apr. 22, 2021

Related U.S. Application Data

(63) Continuation of application No. 16/082,747, filed as application No. PCT/US2017/021551 on Mar. 9, 2017, now Pat. No. 10,752,584.

(60) Provisional application No. 62/305,865, filed on Mar. 9, 2016.

(51) Int. Cl.
| | |
|---|---|
| *A61K 31/4025* | (2006.01) |
| *A61K 31/454* | (2006.01) |
| *A61K 31/427* | (2006.01) |
| *A61K 31/4192* | (2006.01) |
| *A61P 31/20* | (2006.01) |
| *C07D 207/34* | (2006.01) |
| *C07D 249/04* | (2006.01) |
| *C07D 401/12* | (2006.01) |
| *C07D 403/12* | (2006.01) |
| *A61K 45/06* | (2006.01) |
| *C07D 417/12* | (2006.01) |
| *A61K 31/40* | (2006.01) |
| *A61K 31/41* | (2006.01) |
| *A61K 31/4178* | (2006.01) |
| *A61K 31/4184* | (2006.01) |
| *A61K 31/496* | (2006.01) |
| *A61K 31/506* | (2006.01) |
| *A61K 31/5377* | (2006.01) |
| *C07D 207/36* | (2006.01) |
| *C07D 401/06* | (2006.01) |
| *C07D 403/06* | (2006.01) |

(52) U.S. Cl.
CPC ............ *C07D 207/34* (2013.01); *A61K 31/40* (2013.01); *A61K 31/41* (2013.01); *A61K 31/4178* (2013.01); *A61K 31/4184* (2013.01); *A61K 31/4192* (2013.01); *A61K 31/427* (2013.01); *A61K 31/454* (2013.01); *A61K 31/496* (2013.01); *A61K 31/506* (2013.01); *A61K 31/5377* (2013.01); *A61K 45/06* (2013.01); *A61P 31/20* (2018.01); *C07D 207/36* (2013.01); *C07D 249/04* (2013.01); *C07D 401/06* (2013.01); *C07D 401/12* (2013.01); *C07D 403/06* (2013.01); *C07D 403/12* (2013.01); *C07D 417/12* (2013.01)

(58) Field of Classification Search
CPC .............. A61K 31/4025; A61K 31/454; A61K 31/427; A61K 31/4192; A61P 31/20; C07D 207/34; C07D 249/04; C07D 401/12; C07D 403/12
See application file for complete search history.

(56) References Cited

U.S. PATENT DOCUMENTS

9,567,299 B2 * 2/2017 Vandyck .............. A61K 31/445

FOREIGN PATENT DOCUMENTS

| CO | 16008168 | 1/2016 |
|---|---|---|
| WO | 2013006394 A1 | 1/2013 |
| WO | 2013096744 A1 | 6/2013 |
| WO | 2014184350 A1 | 11/2014 |
| WO | 2015011281 A1 | 1/2015 |
| WO | 2015118057 A1 | 8/2015 |

OTHER PUBLICATIONS

STN Printout of Reg. No. 1317973-06-0, Aug. 15, 2011.*
STN Printout of Reg No. 1316297-36-5, Aug. 11, 2011.*
STN Printout of Reg No. 1302772-99-1, May 30, 2011.*
STN Printout of Reg No. 1302772-68-4, May 30, 2011.*
STN Printout of Reg No. 1624399-02-5, Sep. 23, 2014.*
STN Printout of Reg No. 1290536-07-0, May 5, 2011.*
STN Printout of Reg No. 1288403-81-5, May 1, 2011.*
STN Printout of Reg No. 1278771-26-8, Apr. 12, 2011.*
STN Printout of Reg No. 1277546-59-4, Apr. 10, 2011.*
STN Printout of Reg No. 1252541-99-3, Nov. 10, 2010.*
STN Printout of Reg No. 1252519-97-3, Nov. 10, 2010.*
STN Printout of Reg No. 1252363-65-7, Nov. 10, 2010.*
STN Printout of Reg No. 1252318-17-4, Nov. 10, 2010.*
STN Printout of Reg No. 1252277-16-9, Nov. 10, 2010.*
STN Printout of Reg No. 1252209-02-1, Nov. 10, 2010.*

(Continued)

*Primary Examiner* — Brenda L Coleman
(74) *Attorney, Agent, or Firm* — David S. Bradin; Nexsen Pruet, PLLC

(57) ABSTRACT

The present invention is directed to compounds, compositions and methods for preventing, treating or curing Hepatitis B (HBV) infection in human subjects or other animal hosts. The compounds are as also pharmaceutically acceptable, salts, prodrugs, and other derivatives thereof as pharmaceutical compositions and methods for treatment, prevention or eradication of HBV infection.

9 Claims, 3 Drawing Sheets
Specification includes a Sequence Listing.

(56) References Cited

OTHER PUBLICATIONS

STN Printout of Reg No. 1252208-76-6, Nov. 10, 2010.*
STN Printout of Reg No. 1252191-01-7, Nov. 10, 2010.*
STN Printout of Reg No. 1252119-69-9, Nov. 9, 2010.*
STN Printout of Reg No. 1296162-99-6, May 17, 2011.*
STN Printout of Reg No. 1277546-73-2, Apr. 10, 2011.*
STN Printout of Reg No. 1626731-03-0, Sep. 26, 2014.*
International Search Report and Written Opinion issued in counterpart PCT Application No. PCT/US2017/021551 dated Jul. 6, 2017 (ten (10) pages).
Perry et al., Preparation of N-Substituted Phthalimides by the Palladium-Catalyzed Carbonylation and Coupling of o-Dihalo Aromatics and Primary Amines, Journal of Organic Chemistry, vol. 56, No. 23, pp. 6573-6579, 1991.
STN printout of Reg. No. 1279413-35-2, Apr. 13, 2011.
STN printout of Reg. No. 1294741-16-4, May 15, 2011.
STN printout of Reg. No. 1299676-18-8, May 24, 2011.
STN printout of Reg. No. 1299258-74-4, May 24, 2011.
STN printout of Reg. No. 1299094-89-5, May 24, 2011.
STN printout of Reg. No. 1298919-90-0, May 22, 2011.
STN printout of Reg. No. 1302765-20-3, May 30, 2011.
STN printout of Reg. No. 1301339-7 4-1, May 27, 2011.
STN printout of Reg. No. 1300446-34-7, May 25, 2011.
STN printout of Reg. No. 1300446-23-4, May 25, 2011.
STN printout of Reg. No. 1625934-53-3, Sep. 25, 2014.
STN printout of Reg. No. 1623306-88-6, Sep. 18, 2014.
CAPLUS printout of Kuroda et al., Phthalonic acid, 4,5-Dimethoxyphthalonic Acid and 4,5-Dimethoxy-o-Tolylglyoxylic Acid, Journal of the Chemical Society, Transactions, vol. 123, pp. 2094-2111, 1923.
CAPLUS printout of Staunton et al.. The Constitution of Ciba Yellow 3G, Journal of the Chemical Society, pp. 1889-1894, 1953.

* cited by examiner

ELIMINATION OF HEPATITIS B VIRUS WITH ANTIVIRAL AGENTS

CROSS REFERENCE TO RELATED APPLICATIONS

This application is a continuation application of U.S. patent application Ser. No. 16/082,747, filed Sep. 6, 2018, which is the national stage application under 35 U.S.C. § 371 of International Application No. PCT/US2017/021551, filed Mar. 9, 2017, which claims priority pursuant to 35 U.S.C. § 119(e) to U.S. Provisional Patent Application 62/305,865, filed on Mar. 9, 2016, each of which is hereby incorporated by reference in its entirety.

FIELD OF THE INVENTION

The present invention is directed to compounds, methods and compositions for preventing, treating and/or curing hepatitis B virus (HBV) infections. More specifically, the invention describes specifically substituted aromatic/heteroaromatic compounds, pharmaceutically acceptable salts, or other derivatives thereof, and the use thereof in the treatment of HBV infections.

BACKGROUND OF THE INVENTION

Hepatitis B virus (HBV) causes a serious human health problem and is second only to tobacco as a cause of human cancer. The mechanism by which HBV induces cancer is unknown. It is postulated that it may directly trigger tumor development, or indirectly trigger tumor development through chronic inflammation, cirrhosis, and cell regeneration associated with the infection.

After a 2- to 6-month incubation period, during which the host is typically unaware of the infection, HBV infection can lead to acute hepatitis and liver damage, resulting in abdominal pain, jaundice and elevated blood levels of certain enzymes. HBV can cause fulminant hepatitis, a rapidly progressive, often fatal form of the disease in which large sections of the liver are destroyed.

Subjects typically recover from the acute phase of HBV infection. In some patients, however, the virus continues replication for an extended or indefinite period, causing a chronic infection. Chronic infections can lead to chronic persistent hepatitis. Patients infected with chronic persistent HBV are most common in developing countries. By mid-1991, there were approximately 225 million chronic carriers of HBV in Asia alone and worldwide almost 300 million carriers. Chronic persistent hepatitis can cause fatigue, cirrhosis of the liver, and hepatocellular carcinoma, a primary liver cancer.

In industrialized countries, the high-risk group for HBV infection includes those in contact with HBV carriers or their blood samples. The epidemiology of HBV is very similar to that of HIV/AIDS, which is a reason why HBV infection is common among patients infected with HIV or suffering from AIDS. However, HBV is more contagious than HIV.

3TC (lamivudine), interferon alpha-2b, peginterferon alpha-2a, hepsera (adefovir dipivoxil), baraclude (entecavir), and Tyzeka (Telbivudine) are currently FDA-approved drugs for treating HBV infection. Another nucleoside, tenofovir alafenamide fumarate (TAF) (formerly GS-7340) is currently in phase 3. All these drugs are highly effective in reducing viral load, but none of these drugs provide a cure for HBV. In addition, their impact can be limited by drug resistance, low efficacy and tolerability issues. The low cure rates of HBV are attributed at least in part to the presence and persistence of covalently closed circular DNA (cccDNA) in the nucleus of infected hepatocytes.

Accordingly, there is an urgent need for new HBV drugs that are potent, safe, that work by a different mechanism than nucleoside analogs, and can reduce the latent form of HBV known as cccDNA.

It would be advantageous to provide new antiviral agents, compositions including these agents, and methods of treatment using these agents to treat HBV and prevent the emergence of drug-resistant HBV. The present invention provides such agents, compositions and methods.

SUMMARY OF THE INVENTION

The present invention provides compounds, methods and compositions for preventing, treating and/or curing HBV infection in a host, or reducing the activity of HBV in the host. The methods involve administering a therapeutically or prophylactically-effective amount of at least one compound as described herein to treat, cure or prevent an infection by, or an amount sufficient to reduce the biological activity of, an HBV infection.

The compounds can also be used to treat other viral infections, including those by flaviviridae viruses, such as West Nile virus (WNV) and, hepatitis C virus (HCV), Dengue Fever, Zika virus.

The pharmaceutical compositions include one or more of the compounds described herein, in combination with a pharmaceutically acceptable carrier or excipient, for treating a host infected with HBV. These compounds can be used in combination with nucleoside and non-nucleoside inhibitors of HBV. The formulations can further include at least one other therapeutic agent. In addition, the present invention includes processes for preparing such compounds.

In one embodiment, the compounds have the following formula:

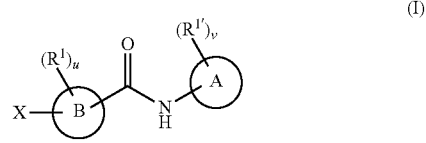

(I)

or a pharmaceutically acceptable salt or prodrug thereof, wherein:

A is phenyl, a six-membered heteroaromatic ring containing one, two, or three nitrogen atoms, a five-membered heteroaromatic ring containing one, two, or three heteroatoms which are, independently, N, O, or S; a $C_{4-14}$ bicyclic ring, alkylheteroaryl, or alkylaryl;

B is a six or seven-membered ring or a six or seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a $C_{5-14}$ bicyclic ring, When $R^1$ and $R^{1'}$ are attached to a carbon, they are, independently, hydrogen, halogen (including F, Cl, Br, and I), $SF_5$, $CF_3$, hydroxy, $N(R')S(O)_2R'$, $S(O)_2R'$, $S(O)_2N(R')_2$, $C_{1-6}$ alkoxy, $C_{1-6}$ haloalkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl;

When $R^1$ and $R^{1'}$ are attached to a nitrogen, they are, independently, hydrogen, $C_{2-6}$ alkoxy, $C_{3-6}$ alkoxyalkyl, $C_{2-6}$ alkenyl, alkoxycarbonyl, carbonylalkyl, carbonyl aryl, $C_{1-6}$ alkyl, heterocyclylalkyl, $C_{2-6}$ hydroxyalkyl, or $S(O)_2R'$;

Each R' is independently H, $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl, or if two R' reside on the same nitrogen atom, they can come together to form a $C_{3-6}$ ring optionally containing a N, O, or S heteroatom;

The R' groups can optionally be substituted with one or more substituents, which substituents are, independently, halo, $C_{1-6}$ haloalkyl, $C_{1-6}$ hydroxyalkyl, hydroxyl, carboxyl, acyl, aryl, acyloxy, amino, amido, carboxyl derivatives, alkylamino, dialkylamino, arylamino, alkoxy, alkoxyalkyl, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference;

u and v are independently 0, 1, 2, 3, 4 or 5;

X is

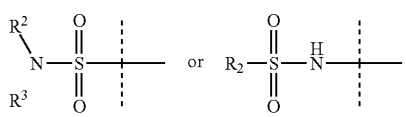

$R^3$ is H, $C_{1-6}$ alkyl, $C_{1-6}$ haloalkyl, $C_{2-6}$ alkenyl, or $C_{2-6}$ alkynyl, $R^2$ is $C_{1-6}$ alkyl, $C_{1-6}$ haloalkyl, $C_{2-8}$ alkoxyalkyl, $C_{2-6}$ alkenyl, $C_{2-6}$ alkynyl, aryl, such as phenyl, heteroaryl, including six-membered heteroaromatic rings containing one, two, or three nitrogen atoms and five-membered heteroaromatic rings containing one, two, or three heteroatoms, which, independently, are N, O, or S, alkylaryl, arylalkyl, a six-membered ring or a six-membered bridged or spiro-fused ring containing zero, one, or two heteroatoms which are, independently, N, O, or S, a seven-membered bridged or spiro-fused ring containing zero, one, or two heteroatoms which are, independently, N, O, or S, a five-membered ring containing zero, one, or two heteroatoms which are, independently, N, O, or S; a four-membered ring containing zero, one, or two heteroatoms which are, independently, N, O, or S; cycloalkyl, alkylheteroaryl, or alkylaryl;

$R^2$ is optionally substituted with one or more substituents, which each, independently, are halogen (including F, Cl, Br, and I), $CF_3$, $SF_5$, hydroxy, $N(R')S(O)_2R'$, $S(O)_2R'$, $S(O)_2N(R')_2$, $C_{1-6}$ alkoxy, $C_{1-6}$ haloalkoxy, cyano, azido, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl; or is optionally substituted with aryl, substituted aryl, heteroaryl, or substituted heteroaryl, where substituents on the substituted aryl and substituted heteroaryl are selected from the group consisting of halogen, $SF_5$, $CF_3$, hydroxy, $N(R')S(O)_2R'$, $S(O)_2R'$, $S(O)_2N(R')_2$, $C(O)R'$, $C_{1-6}$ alkoxy, cyano, azido, $C_{2-6}$ alkynyl, $C_{3-6}$ alkoxyalkyl, alkoxycarbonyl, alkoxycarbonylalkyl, and $C_{1-6}$ alkyl.

or $R^2$ and $R^3$ can come together with the nitrogen to which they are attached to form a 6-10 membered bicyclic or bridged ring, a 3 to 8 saturated ring, or a 5 membered unsaturated ring; such bicyclic, bridged, saturated and unsaturated rings optionally containing one or more additional heteroatoms, where each is, independently, O, S or N, and optionally being substituted with one or more substituents, wherein each, independently, is halogen (including F, Cl, Br, I), $CF_3$, hydroxy, $N(R')S(O)_2R'$, $S(O)_2R'$, $S(O)_2N(R')_2$, $C_{1-6}$ alkoxy, cyano, azido, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl.

In a second embodiment, the compounds have the following formula:

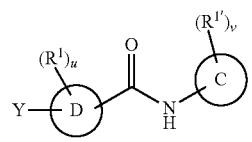

(II)

or a pharmaceutically acceptable salt or prodrug thereof, wherein $R^1$ and $R^{1'}$ are as defined with respect to Formula I, u and v are independently 0, 1, 2, 3, 4 or 5;

C is phenyl, a six-membered heteroaromatic ring containing one, two, or three nitrogen atoms, a five-membered heteroaromatic ring containing one, two, or three heteroatoms which are, independently, N, O, or S; a $C_{4-14}$ bicyclic ring, alkylaryl, or alkylheteroaryl;

D is phenyl, a six-membered heteroaromatic ring containing one, two, or three nitrogen atoms, a five-membered heteroaromatic ring containing one, two, or three heteroatoms, which are, independently, N, O, or S, or a $C_{5-14}$ bicyclic ring, Y is

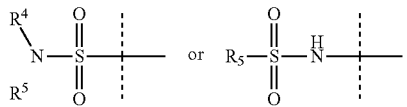

$R^4$ is H or $C_{1-6}$ alkyl, $C_{1-6}$ haloalkyl, $C_{2-6}$ alkenyl, $C_{2-6}$ alkynyl; in one embodiment, $R^4$ is $C_{1-6}$ alkyl, $C_{1-6}$ haloalkyl, $C_{2-6}$ alkenyl, $C_{2-6}$ alkynyl, $R^5$ is alkylaryl, arylalkyl, $C_{2-6}$ alkenyl, $C_{2-6}$ alkynyl, aryl, such as phenyl, heteroaryl, including six-membered heteroaromatic rings containing one, two, or three nitrogen atoms and five-membered heteroaromatic rings containing one, two, or three heteroatoms, which, independently, are N, O, or S; and a six-membered bridged or spiro-fused ring containing zero, one, or two heteroatoms which are, independently, N, O, or S; in one embodiment, $R^5$ is alkylaryl, arylalkyl, phenyl, a five or six-membered heteroaryl, or a six-membered bridged or spiro-fused ring containing zero, one, or two heteroatoms which are, independently, N, O, or S;

$R^5$ is optionally substituted with one or more substituents, each of which is, independently, halogen (including F, Cl, Br, and I), $CF_3$, $SF_5$, hydroxy, $N(R')S(O)_2R'$, $S(O)_2R'$, $S(O)_2N(R')_2$, $C_{1-6}$ alkoxy, $C_{1-6}$ haloalkoxy, cyano, azido, $C_{2-6}$ alkynyl, $C_{3-6}$ alkoxyalkyl, alkoxycarbonyl, alkoxycarbonylalkyl, $C_{1-6}$ alkyl, cycloalkyl, arylalkoxycarbonyl, carboxy, $C_{1-6}$ haloalkyl, heterocyclylalkyl, or $C_{1-6}$ hydroxyalkyl; or is substituted with aryl, substituted aryl, heteroaryl, or substituted heteroaryl, where substituents on the substituted aryl and substituted heteroaryl are selected from the group consisting of halogen, $SF_5$, $CF_3$, hydroxy, $N(R')S(O)_2R'$, $S(O)_2R'$, $S(O)_2N(R')_2$, $C(O)R'$, $C_{1-6}$ alkoxy, cyano, azido, $C_{2-6}$ alkynyl, $C_{3-6}$ alkoxyalkyl, alkoxycarbonyl, alkoxycarbonylalkyl, and $C_{1-6}$ alkyl;

where, in one embodiment, if C is phenyl, D is not phenyl or a 5-membered ring heteroaryl, and in another embodiment, if C is phenyl and D is phenyl or a 5-membered ring heteroaryl, then $R^5$ is not alkylaryl, alkenyl, or a six-membered bridged ring;

or when Y is

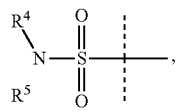

$R^4$ and $R^5$ together with the nitrogen to which they are attached to form a 3 to 4 membered ring optionally substituted with one or more substituents, each of which is, independently, halogen (including F, Cl, Br, I), $CF_3$, hydroxy, $N(R')S(O)_2R'$, $S(O)_2R'$, $S(O)_2N(R')_2$, $C_{1-6}$ alkoxy, cyano, azido, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl.

In one embodiment, D is

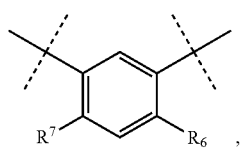

where $R^6$ is H, Cl, F or Br, and $R^7$ is H, methyl, F or Cl.

In one aspect of this embodiment, when Y is

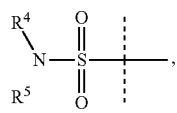

$R^5$ is not

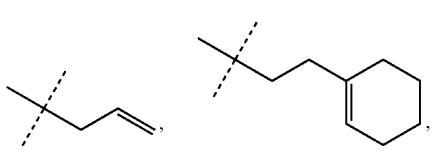

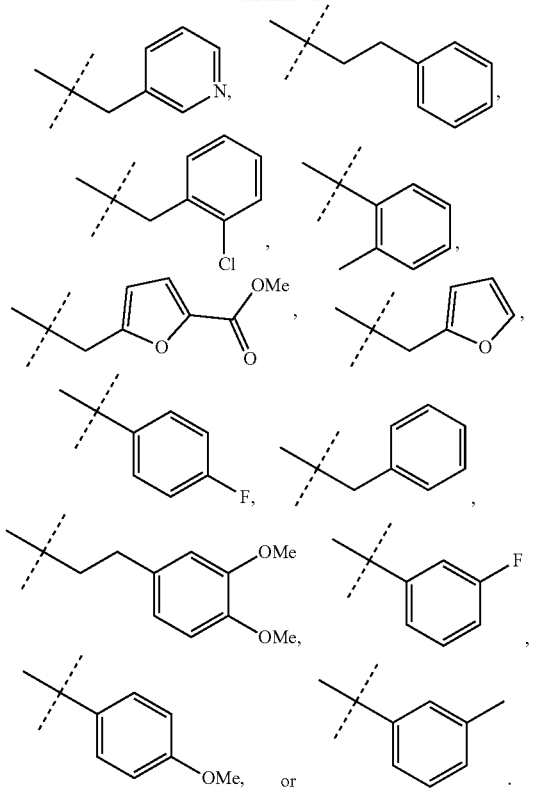

In another aspect of this embodiment, when $R^4$ is ethyl, then $R^5$ is not

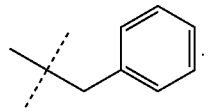

In a third embodiment, the compounds have the following formula:

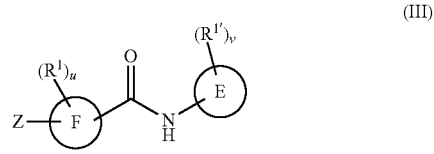

(III)

or a pharmaceutically acceptable salt or prodrug thereof, wherein $R^1$ and $R^{1'}$ are as defined with respect to Formula I, u and v are independently 0, 1, 2, 3, 4 or 5;

E is a six-membered heteroaromatic ring containing one, two, or three nitrogen atoms, a five-membered heteroaromatic ring containing one, two, or three heteroatoms, where each is, independently, N, O, or S; a $C_{4-14}$ bicyclic ring, alkylheteroaryl, or alkylaryl;

F is a five-membered heteroaromatic ring containing one, two, or three heteroatoms which are, independently, N, O, or S, or a $C_{4-14}$ bicyclic ring, Z is

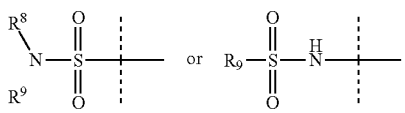

R$^8$ is H, C$_{1-6}$ alkyl, C$_{1-6}$ haloalkyl, C$_{2-6}$ alkenyl, or C$_{2-6}$ alkynyl, R$^9$ is C$_{1-6}$ alkyl, C$_{1-6}$ haloalkyl, C$_{2-8}$ alkoxyalkyl, a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring;

R$^9$ is optionally substituted with one or more substituents, each of which is independently halogen (including F, Cl, Br, and I), CF$_3$, SF$_5$, hydroxy, N(R')S(O)$_2$R', S(O)$_2$R', S(O)$_2$N(R')$_2$, C$_{1-6}$ alkoxy, C$_{1-6}$ halo alkoxy, cyano, azido, C$_{2-6}$ alkynyl, C$_{3-6}$ alkoxyalkyl, alkoxycarbonyl, alkoxycarbonylalkyl, C$_{1-6}$ alkyl, cycloalkyl, arylalkoxycarbonyl, carboxy, C$_{1-6}$ haloalkyl, heterocyclylalkyl, or C$_{1-6}$ hydroxyalkyl; or is substituted with aryl, substituted aryl, heteroaryl, or substituted heteroaryl, where substituents on the substituted aryl and substituted heteroaryl are selected from the group consisting of halogen, SF$_5$, CF$_3$, hydroxy, N(R')S(O)$_2$R', S(O)$_2$R', S(O)$_2$N(R')$_2$, C(O)R', C$_{1-6}$ alkoxy, cyano, azido, C$_{2-6}$ alkynyl, C$_{3-6}$ alkoxyalkyl, alkoxycarbonyl, alkoxycarbonylalkyl, and C$_{1-6}$ alkyl; or R$^8$ and R$^9$ can come together with the nitrogen to which they are attached to form a 6-10 membered bicyclic or bridged ring or a 3 to 8 saturated ring; such bicyclic, bridged and saturated ring moiety optionally containing one or more additional heteroatoms which, independently, are 0, S or N and optionally being substituted with one or more substituents, each, independently, is halogen (including F, Cl, Br, and I), CF$_3$, hydroxy, N(R')S(O)$_2$R', S(O)$_2$R', S(O)$_2$N(R')$_2$, C$_{1-6}$ alkoxy, cyano, azido, C$_{2-6}$ alkynyl, C$_{3-6}$ alkoxyalkyl, alkoxycarbonyl, alkoxycarbonylalkyl, C$_{1-6}$ alkyl, arylalkoxycarbonyl, carboxy, C$_{1-6}$ haloalkyl, heterocyclylalkyl, or C$_{1-6}$ hydroxyalkyl.

In a fourth embodiment, the compounds have the following formula:

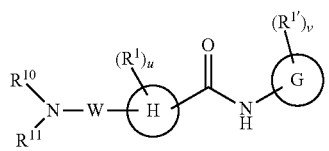

or a pharmaceutically acceptable salt or prodrug thereof, wherein

G is phenyl, a six-membered heteroaromatic ring containing one, two, or three nitrogen atoms, a five-membered heteroaromatic ring containing one, two, or three heteroatoms, which are, independently, N, O, or S; a C$_{4-14}$ bicyclic ring, alkylheteroaryl, or alkylaryl;

H is phenyl, a six-membered heteroaromatic ring containing one, two, or three nitrogen atoms, a six-membered non-aromatic ring optionally containing one, two, or three heteroatoms, which are, independently, N, O, or S; or a C$_{4-14}$ bicyclic ring;

When R$^1$ and R$^{1'}$ are attached to a carbon they are, independently, hydrogen, halogen (including F, Cl, Br, and I), CF$_3$, hydroxy, N(R')S(O)$_2$R', S(O)$_2$R', S(O)$_2$N(R')$_2$, C$_{1-6}$ alkoxy, cyano, C$_{2-6}$ alkynyl, C$_{3-6}$ alkoxyalkyl, alkoxycarbonyl, alkoxycarbonylalkyl, C$_{1-6}$ alkyl, arylalkoxycarbonyl, carboxy, C$_{1-6}$ haloalkyl, heterocyclylalkyl, or C$_{1-6}$ hydroxyalkyl;

When R$^1$ and R$^{1'}$ are attached to a nitrogen they are, independently, hydrogen, C$_{1-6}$ alkoxy, C$_{3-6}$ alkoxyalkyl, alkoxycarbonyl, carbonylalkyl, carbonyl aryl, C$_{1-6}$ alkyl, C$_{2-6}$ alkynyl, C$_{2-6}$ alkenyl, heterocyclylalkyl, C$_{1-6}$ hydroxyalkyl, or S(O)$_2$R';

Each R' is independently H, C$_{1-6}$ alkyl, C$_{1-6}$ haloalkyl, C$_{1-6}$ alkoxy, C$_{2-6}$ alkenyl, C$_{2-6}$ alkynyl, C$_{3-6}$ cycloalkyl, aryl, heteroaryl, alkylaryl, or arylalkyl, or if two R' reside on the same nitrogen atom they can come together to form a C$_{3-6}$ alkyl ring optionally containing a N, O, or S; wherein the R' groups can be substituted with one or more substituents as defined above, for example, C$_{1-6}$ hydroxyalkyl, aminoalkyl, and alkoxyalkyl;

u and v are independently 0, 1, 2, 3, 4 or 5;

W is

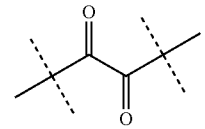

R$^{10}$ is H, C$_{1-6}$ alkyl, C$_{1-6}$ haloalkyl, C$_{2-6}$ alkenyl, or C$_{2-6}$ alkynyl, R$^{11}$ is C$_{1-6}$ alkyl, C$_{1-6}$ haloalkyl, C$_{2-8}$ alkoxyalkyl, C$_{2-6}$ alkenyl, C$_{2-6}$ alkynyl, aryl, heteroaryl, alkylaryl, arylalkyl, phenyl, a six-membered heteroaromatic ring containing one, two, or three nitrogen atoms, a six-membered ring or a six-membered bridged or spiro-fused ring containing zero, one, or two heteroatoms, which are, independently, N, O, or S, a seven-membered bridged or spiro-fused ring containing zero, one, or two heteroatoms, which are, independently, N, O, or S, a five-membered heteroaromatic ring containing one, two, or three heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S; a three membered ring, alkylheteroaryl, or alkylaryl;

wherein R$^{11}$ is optionally substituted with one or more substituents selected from the group consisting of halogen (including F, Cl, Br, and I), SF$_5$, CF$_3$, hydroxy, N(R')S(O)$_2$R', S(O)$_2$R', S(O)$_2$N(R')$_2$, C$_{1-6}$ alkoxy, C$_{1-6}$ haloalkoxy, C$_{2-6}$ alkenyl, cyano, C$_{2-6}$ alkynyl, C$_{3-6}$ alkoxyalkyl, alkoxycarbonyl, alkoxycarbonylalkyl, C$_{1-6}$ alkyl, arylalkoxycarbonyl, carboxy, C$_{1-6}$ haloalkyl, heterocyclylalkyl, C$_{1-6}$ hydroxyalkyl, aryl, substituted aryl, heteroaryl, and substituted heteroaryl, where substituents on the substituted aryl and substituted heteroaryl are selected from the group consisting of halogen, SF$_5$, CF$_3$, hydroxy, N(R')S(O)$_2$R', S(O)$_2$R', S(O)$_2$ N(R')$_2$, C(O)R', C$_{1-6}$ alkoxy, cyano, azido, C$_{2-6}$ alkynyl, C$_{3-6}$ alkoxyalkyl, alkoxycarbonyl, alkoxycarbonylalkyl, and C$_{1-6}$ alkyl;

or

R$^{10}$ and R$^{11}$ can come together with the nitrogen to which they are attached to form a 6-10 membered bicyclic or bridged ring or a 3 to 8 saturated ring; such bicyclic, bridged or saturated ring moiety optionally containing one or more additional heteroatoms, which are each, independently, O, S or N, and optionally substituted with one or more substituents, each of which is, independently, halogen (including F, Cl, Br, and I), CF$_3$, SF$_5$, hydroxy, N(R')S(O)$_2$R', S(O)$_2$R', S(O)$_2$N(R')$_2$, C$_{1-6}$ alkoxy, cyano, azido, C$_{2-6}$ alkynyl, C$_{3-6}$ alkoxyalkyl, alkoxycarbonyl, alkoxycarbonylalkyl, C$_{1-6}$ alkyl, arylalkoxycarbonyl, carboxy, C$_{1-6}$ haloalkyl, heterocyclylalkyl, or C$_{1-6}$ hydroxyalkyl.

In a fifth embodiment, the compounds have the following formula:

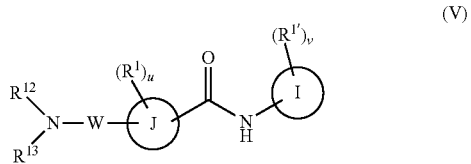

(V)

or a pharmaceutically acceptable salt or prodrug thereof, wherein

R$^1$ and R$^{1'}$ are as defined with respect to Formula I, u and v are independently 0, 1, 2, 3, 4 or 5;

I is phenyl, a six-membered heteroaromatic ring containing one, two, or three nitrogen atoms, a five-membered heteroaromatic ring containing one, two, or three heteroatoms, which are, independently, N, O, or S, a C$_{4-14}$ bicyclic ring; alkylheteroaryl, or alkylaryl;

J is a five-membered heteroaromatic ring containing one, two, or three heteroatoms, which are, independently, N, O, or S, a six or seven-membered ring or a six or seven-membered bridged or spiro-fused ring containing zero, one, or two heteroatoms which are, independently, N, O, or S, a five-membered ring containing zero, one, or two heteroatoms which are, independently, N, O, or S; or a four-membered ring containing zero, one, or two heteroatoms which are, independently, N, O, or S, W is

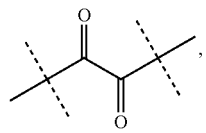

R$^{12}$ is H, C$_{1-6}$ alkyl, C$_{1-6}$ haloalkyl, C$_{2-6}$ alkenyl, or C$_{2-6}$ alkynyl, R$^{13}$ is C$_{2-6}$ alkenyl, C$_{2-6}$ alkynyl, aryl, including phenyl, heteroaryl, including six-membered heteroaromatic rings containing one, two, or three nitrogen atoms and five-membered heteroaromatic rings containing one, two, or three heteroatoms, which are, independently, N, O, or S; alkylaryl, arylalkyl, a C$_{4-14}$ bicyclic ring; a six-membered bridged or spiro-fused ring containing zero, one, or two heteroatoms which are, independently, N, O, or S, R$^{13}$ is optionally substituted with one or more substituents each independently selected from the group consisting of hydrogen, halogen (F, Cl, Br, I), CF$_3$, SF$_5$, hydroxy, N(R')S(O)$_2$R', S(O)$_2$R', S(O)$_2$N(R')$_2$, C(O)R', C$_{1-6}$ alkoxy, C$_{1-6}$ haloalkoxy, cyano, azido, C$_{2-6}$ alkynyl, C$_{3-6}$ alkoxyalkyl, alkoxycarbonyl, alkoxycarbonylalkyl, C$_{1-6}$ alkyl, cycloalkyl, arylalkoxycarbonyl, carboxyl, haloalkyl, heterocyclylalkyl, or C$_{1-6}$ hydroxyalkyl; or is optionally substituted with aryl, substituted aryl, heteroaryl, and substituted heteroaryl, where substituents on the substituted aryl and substituted heteroaryl are selected from the group consisting of halogen, SF$_5$, CF$_3$, hydroxy, N(R')S(O)$_2$R', S(O)$_2$R', S(O)$_2$N(R')$_2$, C(O)R', C$_{1-6}$ alkoxy, cyano, azido, C$_{2-6}$ alkynyl, C$_{3-6}$ alkoxyalkyl, alkoxycarbonyl, alkoxycarbonylalkyl, and C$_{1-6}$ alkyl;

or R$^{12}$ and R$^{13}$ together with the nitrogen to which they are attached form a 3 to 4 membered ring optionally substituted with one or more substituents each independently selected from the group consisting of hydrogen, halogen (F, Cl, Br, I), CF$_3$, hydroxy, N(R')S(O)$_2$R', S(O)$_2$R', S(O)$_2$N(R')$_2$, C$_{1-6}$ alkoxy, cyano, azido, C$_{2-6}$ alkynyl, C$_{3-6}$ alkoxyalkyl, alkoxycarbonyl, alkoxycarbonylalkyl, C$_{1-6}$ alkyl, arylalkoxycarbonyl, carboxy, C$_{1-6}$ haloalkyl, heterocyclylalkyl, and C$_{1-6}$ hydroxyalkyl.

In a sixth embodiment, the compounds have the following formula:

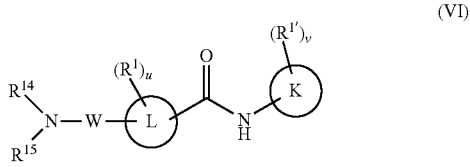

(VI)

or a pharmaceutically acceptable salt or prodrug thereof, wherein

R$^1$ and R$^{1'}$ are as defined with respect to Formula I, u and v are independently 0, 1, 2, 3, 4 or 5;

K is a six-membered heteroaromatic ring containing one, two, or three nitrogen atoms, a five-membered heteroaromatic ring containing one, two, or three heteroatoms which are, independently, N, O, or S; a C$_{4-14}$ bicyclic ring, alkylheteroaryl, or alkylaryl;

L is a five-membered heteroaromatic ring containing one, two, or three heteroatoms which are, independently, N, O, or S, a six or seven-membered ring or a six or seven-membered bridged or spiro-fused ring containing zero, one, or two heteroatoms which are, independently, N, O, or S, a five-membered ring containing zero, one, or two heteroatoms which are, independently, N, O, or S; a four-membered ring containing zero, one, or two heteroatoms which are, independently, N, O, or S, or a C$_{4-14}$ bicyclic ring, W is

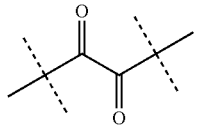

R$^{14}$ is H, C$_{1-6}$ alkyl, C$_{1-6}$ haloalkyl, C$_{2-6}$ alkenyl, or C$_{2-6}$ alkynyl, R$^{15}$ is C$_{1-6}$ alkyl, C$_{1-6}$ haloalkyl, C$_{2-8}$ alkoxyalkyl, a six-membered ring or a six-membered bridged or spiro-fused ring containing zero, one, or two heteroatoms which are, independently, N, O, or S, a seven-membered bridged or spiro-fused ring containing zero, one, or two heteroatoms which are, independently, N, O, or S, a five-membered ring containing zero, one, or two heteroatoms which are, independently, N, O, or S; a four-membered ring containing zero, one, or two heteroatoms which are, independently, N, O, or S;

R$^{15}$ is optionally substituted with one or more substituents which are, independently, halogen (F, Cl, Br, I), SF$_5$, CF$_3$, hydroxy, N(R')S(O)$_2$R', S(O)$_2$R', S(O)$_2$N(R')$_2$, C$_{1-6}$ alkoxy, C$_{1-6}$ haloalkoxy, cyano, azido, C$_{2-6}$ alkynyl, C$_{3-6}$ alkoxyalkyl, alkoxycarbonyl, alkoxycarbonylalkyl, C$_{1-6}$ alkyl, cycloalkyl, arylalkoxycarbonyl, carboxy, C$_{1-6}$ haloalkyl, heterocyclylalkyl, or C$_{1-6}$ hydroxyalkyl; or is optionally substituted with aryl, substituted aryl, heteroaryl, or substituted heteroaryl, where substituents on the substituted aryl and substituted heteroaryl are selected from the group consisting of halogen, SF$_5$, CF$_3$, hydroxy, N(R')S(O)$_2$R', S(O)$_2$R', S(O)$_2$N(R')$_2$, C(O)R', C$_{1-6}$ alkoxy, cyano, azido, C$_{2-6}$ alkynyl, C$_{3-6}$ alkoxyalkyl, alkoxycarbonyl, alkoxycarbonylalkyl, and C$_{1-6}$ alkyl;

or

R$^{14}$ and R$^{15}$ can come together with the nitrogen to which they are attached to form a 6-10 membered bicyclic or bridged ring or a 3 to 8 saturated ring; such bicyclic, bridged and saturated ring moiety optionally containing one or more additional heteroatoms which are, independently, O, S or N, and optionally being substituted with one or more substituents each independently selected from the group consisting of halogen (including F, Cl, Br, and I), SF$_5$, CF$_3$, hydroxy, N(R')S(O)$_2$R', S(O)$_2$R', S(O)$_2$N(R')$_2$, C$_{1-6}$ alkoxy, cyano, azido, C$_{2-6}$ alkynyl, C$_{3-6}$ alkoxyalkyl, alkoxycarbonyl, alkoxycarbonylalkyl, C$_{1-6}$ alkyl, arylalkoxycarbonyl, carboxy, C$_{1-6}$ haloalkyl, heterocyclylalkyl, and C$_{1-6}$ hydroxyalkyl.

In a seventh embodiment, the compounds have the following formula:

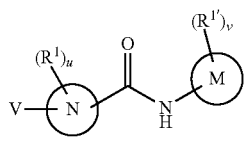

(VII)

or a pharmaceutically acceptable salt or prodrug thereof, wherein

R$^1$ and R$^{1'}$ are as defined with respect to Formula I, u and v are independently 0, 1, 2, 3, 4 or 5;

M is phenyl, a six-membered heteroaromatic ring containing one, two, or three nitrogen atoms, a five-membered heteroaromatic ring containing one, two, or three heteroatoms which are, independently, N, O, or S, a C$_{4-14}$ bicyclic ring, alkylheteroaryl, or alkylaryl, N is phenyl, a six-membered heteroaromatic ring containing one, two, or three nitrogen atoms, a five-membered heteroaromatic ring containing one, two, or three heteroatoms independently N, O, or S, a six or seven-membered ring or a six or seven-membered bridged or spiro-fused ring containing zero, one, or two heteroatoms which are, independently, N, O, or S, a five-membered ring containing zero, one, or two heteroatoms which are, independently, N, O, or S; a four-membered ring containing zero, one, or two heteroatoms which are, independently, N, O, or S; or a C$_{4-14}$ bicyclic ring, V is

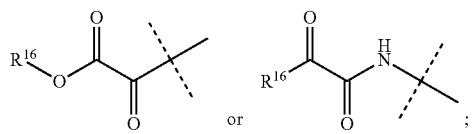

and

R$^{16}$ is C$_{1-6}$ alkyl, C$_{1-6}$ haloalkyl, C$_{2-8}$ alkoxyalkyl, C$_{2-6}$ alkenyl, C$_{2-6}$ alkynyl, aryl, such as phenyl, heteroaryl, such as a six-membered heteroaromatic ring containing one, two, or three nitrogen atoms or a five-membered heteroaromatic ring containing one, two, or three heteroatoms which are, independently, N, O, or S; a six-membered ring or a six-membered bridged or spiro-fused ring containing zero, one, or two heteroatoms which are, independently, N, O, or S, a five-membered ring containing zero, one, or two heteroatoms which are, independently, N, O, or S; a four-membered ring containing zero, one, or two heteroatoms which are, independently, N, O, or S; alkylaryl, arylalkyl, alkylheteroaryl, or alkylaryl, wherein R$^{16}$ is optionally substituted with one or more substituents selected from the group consisting of halogen (including F, Cl, Br, and I), SF$_5$, CF$_3$, hydroxy, N(R')S(O)$_2$R', S(O)$_2$R', S(O)$_2$N(R')$_2$, C$_{1-6}$ alkoxy, C$_{1-6}$ haloalkoxy, C$_{2-6}$ alkenyl, cyano, C$_{2-6}$ alkynyl, C$_{3-6}$ alkoxyalkyl, alkoxycarbonyl, alkoxycarbonylalkyl, C$_{1-6}$ alkyl, arylalkoxycarbonyl, carboxy, C$_{1-6}$ haloalkyl, heterocyclylalkyl, C$_{1-6}$ hydroxyalkyl, aryl, substituted aryl, heteroaryl, and substituted heteroaryl, where substituents on the substituted aryl and substituted heteroaryl are selected from the group consisting of halogen, SF$_5$, CF$_3$, hydroxy, N(R')S(O)$_2$R', S(O)$_2$R', S(O)$_2$N(R')$_2$, C(O)R', C$_{1-6}$ alkoxy, cyano, azido, C$_{2-6}$ alkynyl, C$_{3-6}$ alkoxyalkyl, alkoxycarbonyl, alkoxycarbonylalkyl, and C$_{1-6}$ alkyl.

Representative compounds falling within the scope of the invention include the following:

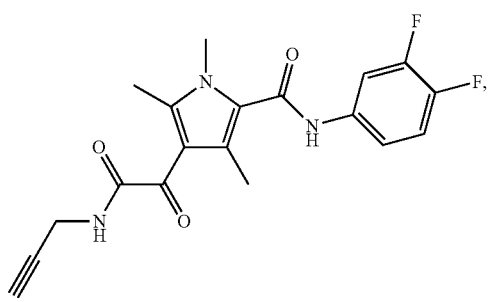

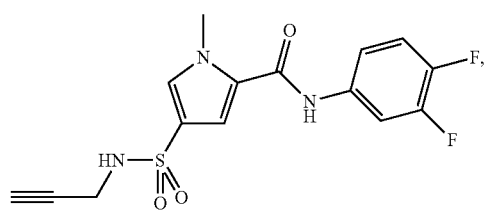

-continued
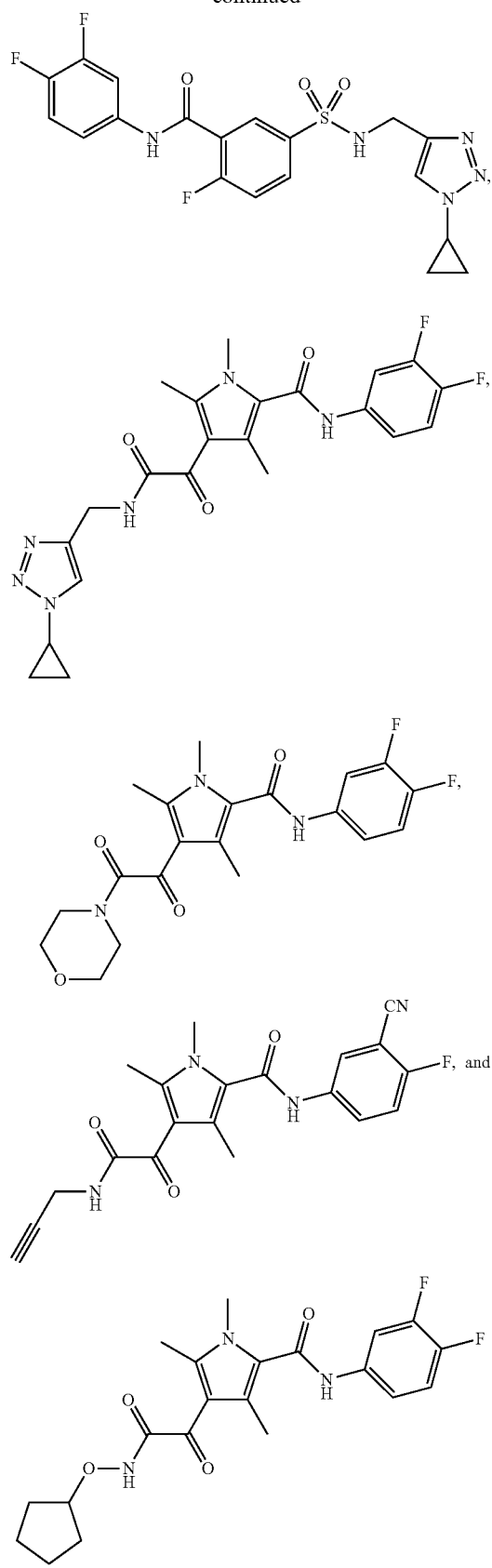
and pharmaceutically acceptable salts or prodrugs thereof.
Additional compounds also include
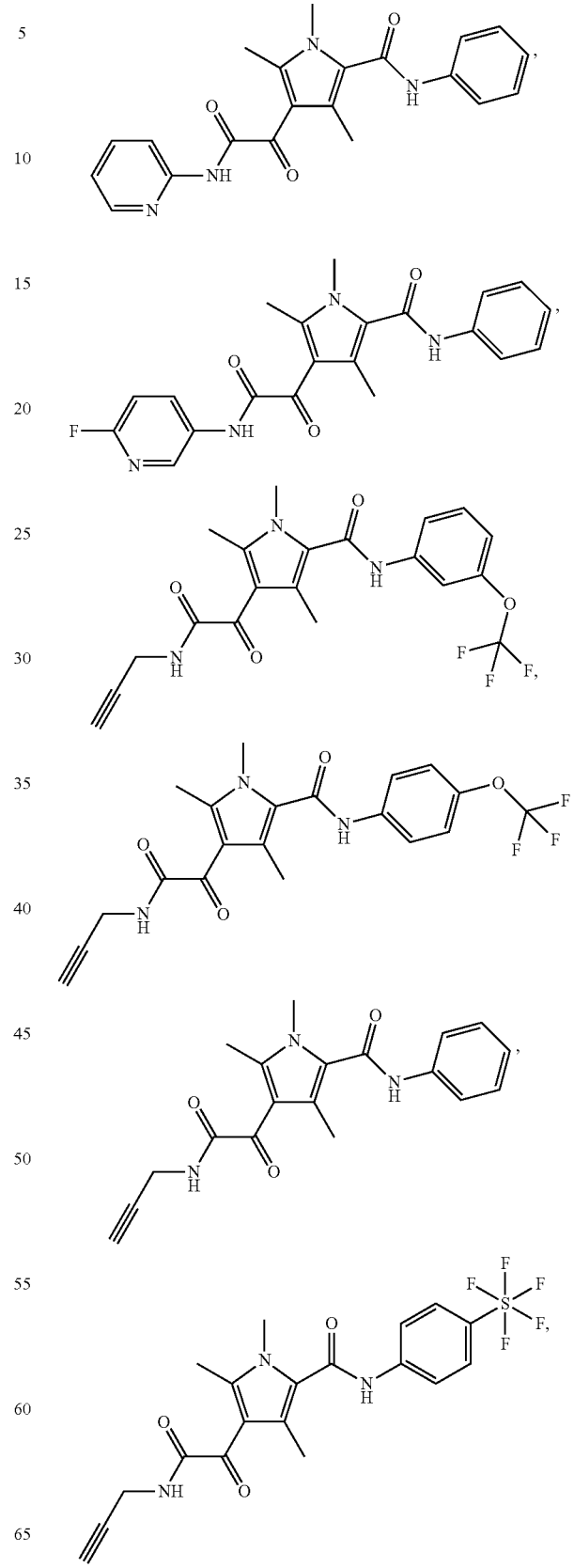

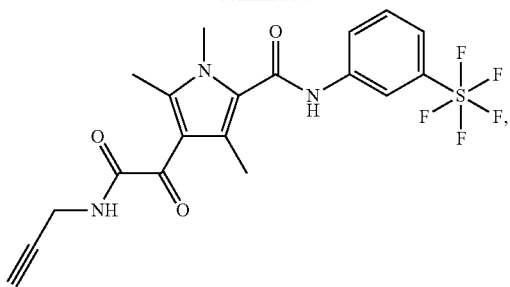
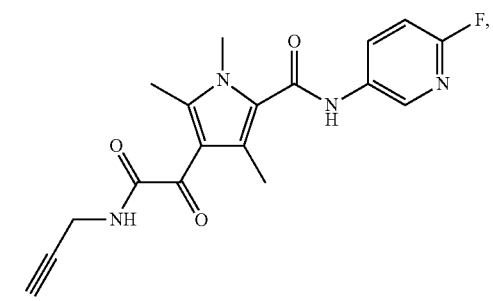
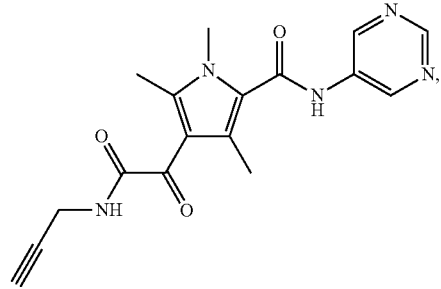
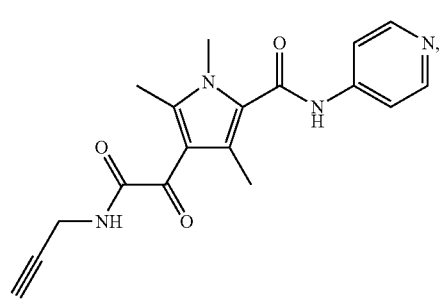
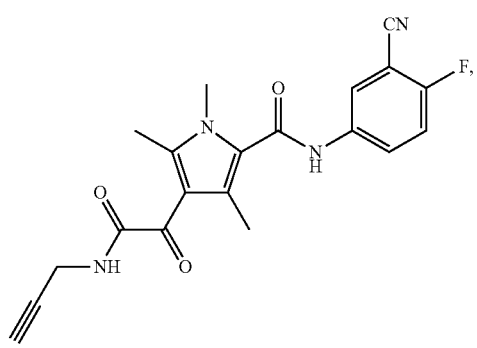
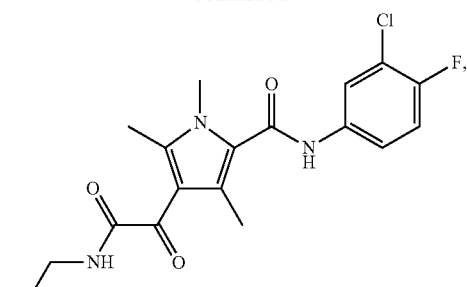
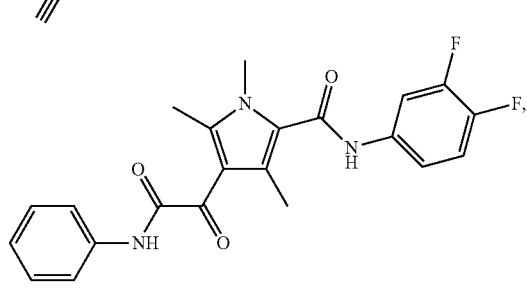
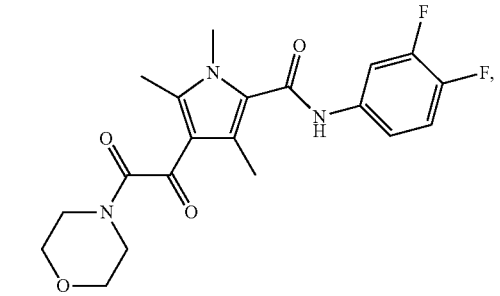
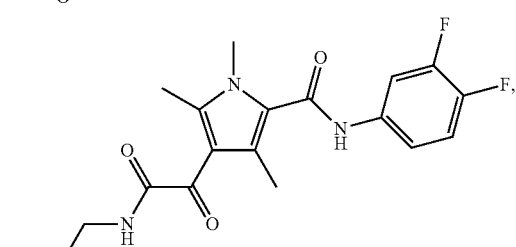
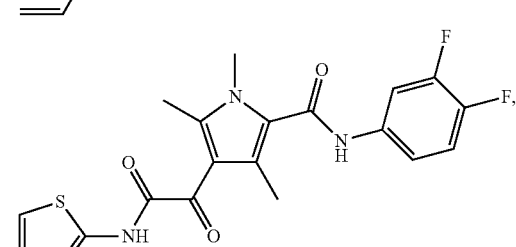
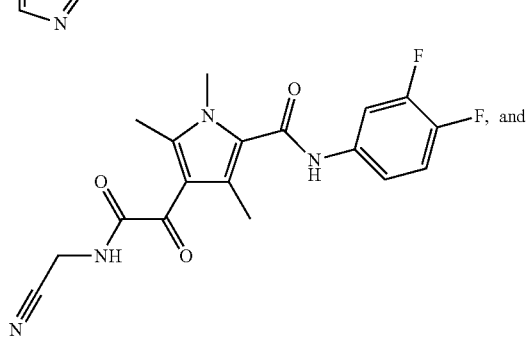

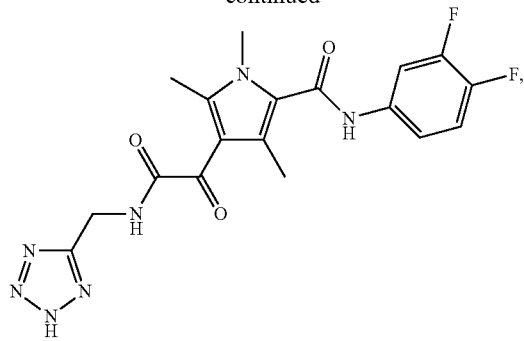

and pharmaceutically acceptable salts or prodrugs thereof.

Particularly preferred compounds include:

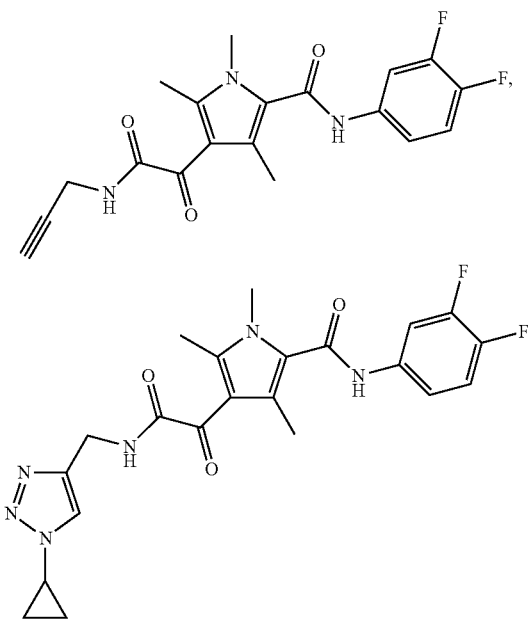

or a pharmaceutically acceptable salt or prodrug thereof.

Also disclosed are pharmaceutical compositions that include one or more of the compounds of Formulas I-VII, and a pharmaceutically-acceptable carrier. The carrier can be, for example, an oral composition, an injectable composition, a transdermal composition, or a nanoparticulate composition. The compositions can further include a second antiviral agent, particularly where the agent is active against HBV infection, and more particularly where the second antiviral agent is active against HBV infection via a different mechanism than the instantly-described compounds.

Representative types of second antiviral agents include polymerase inhibitors, viral entry inhibitors, viral maturation inhibitors, capsid assembly modulators, IMPDH inhibitors, protease inhibitors, immune-based therapeutic agents, reverse transcriptase inhibitors, TLR-agonists, and agents of distinct or unknown mechanism Combinations of these agents can be used.

The compounds described herein can be used to prepare medicaments for treating HBV infection, preventing an HBV infection, or reducing the biological activity of an infection with HBV. The medicaments can further include another anti-HBV agent.

The compounds and compositions can be used in methods for treating a host infected with HBV, preventing an infection from a HBV, and reducing the biological activity of an infection with HBV in a host. The methods can also involve the co-administration of another anti-HBV agent, which co-administration can be simultaneous or sequential.

These and other aspects of the invention are further explained in the following detailed description.

Figure 1:
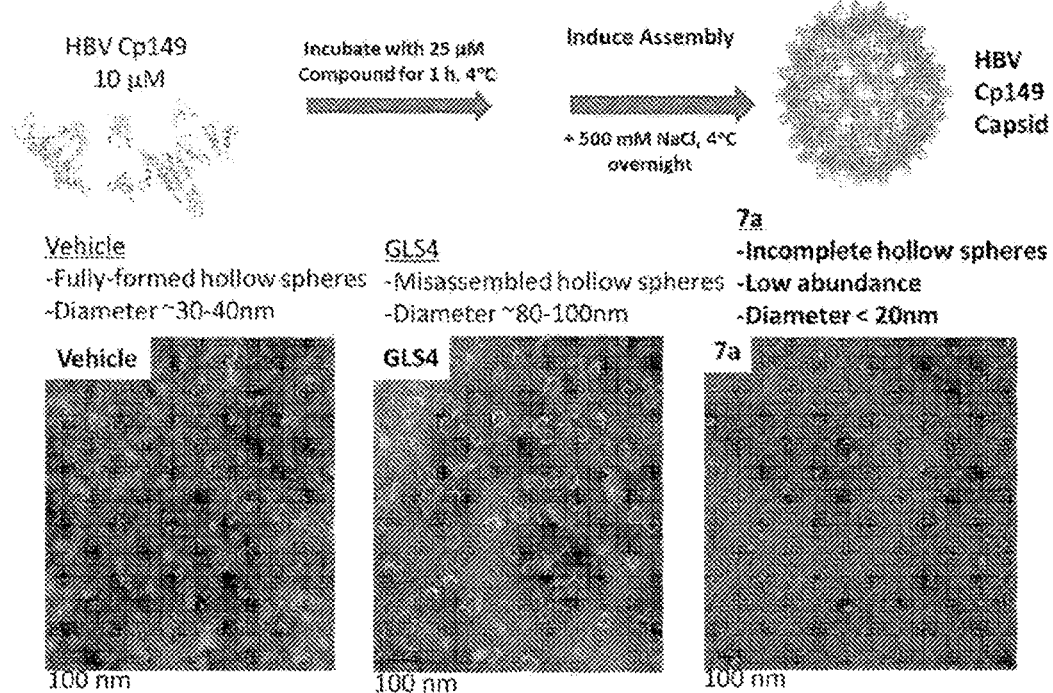
FIG. 1 shows a series of electron micrographs of the result of incubating HBV Cp149 under conditions that would normally form capsids, and where the incubation was accompanied by the addition of a putative active agent, where the active agent functions at least in part by inhibiting capsid formation. Where the incubation was permed using vehicle alone, the electron micrographs show the capsids in the form of fully-formed hollow spheres. When incubated with GLS4, the capsids formed misassembled hollow spheres, and with Compound 7a, the capsids formed incomplete hollow spheres, in a relatively low abundance.

The results show that the compounds effectively disrupted HBV capsid formation.

DETAILED DESCRIPTION

Compounds and compositions useful in treating, preventing, or curing HBV infection are disclosed. Methods for treating, preventing, or curing HBV infection are also disclosed.

The compounds described herein show inhibitory activity against HBV in cell-based assays. Therefore, the compounds can be used to treat or prevent a HBV in a host, or reduce the biological activity of the virus. The host can be a mammal, and in particular, a human, infected with HBV. The methods involve administering an effective amount of one or more of the compounds described herein.

Pharmaceutical formulations including one or more compounds described herein, in combination with a pharmaceutically acceptable carrier or excipient, are also disclosed. In one embodiment, the formulations include at least one compound described herein and at least one further therapeutic agent.

The present invention will be better understood with reference to the following definitions:

I. Definitions

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

As used herein, the term "enantiomerically pure" refers to a compound composition that comprises at least approximately 95%, and, preferably, approximately 97%, 98%, 99% or 100% of a single enantiomer of that compound.

As used herein, the term "substantially free of" or "substantially in the absence of" refers to a compound composition that includes at least 85 to 90% by weight, preferably 95% to 98% by weight, and, even more preferably, 99% to 100% by weight, of the designated enantiomer of that compound. In a preferred embodiment, the compounds described herein are substantially free of enantiomers.

Similarly, the term "isolated" refers to a compound composition that includes at least 85 to 90% by weight, preferably 95% to 98% by weight, and, even more preferably, 99% to 100% by weight, of the compound, the remainder comprising other chemical species or enantiomers.

The term "alkyl," as used herein, unless otherwise specified, refers to a saturated straight, branched, or cyclic, primary, secondary, or tertiary hydrocarbons, including both substituted and unsubstituted alkyl groups. The alkyl group can be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. Specifically included are $CF_3$ and $CH_2CF_3$.

In the text, whenever the term C(alkyl range) is used, the term independently includes each member of that class as if specifically and separately set out. The term "alkyl" includes $C_{1-22}$ alkyl moieties, and the term "lower alkyl" includes $C_{1-6}$ alkyl moieties. It is understood to those of ordinary skill in the art that the relevant alkyl radical is named by replacing the suffix "-ane" with the suffix "-yl".

As used herein, a "bridged alkyl" refers to a bicyclo- or tricyclo alkane, for example, a 2:1:1 bicyclohexane.

As used herein, a "spiro alkyl" refers to two rings that are attached at a single (quaternary) carbon atom.

The term "alkenyl" refers to an unsaturated, hydrocarbon radical, linear or branched, in so much as it contains one or more double bonds. The alkenyl group disclosed herein can be optionally substituted with any moiety that does not adversely affect the reaction process, including but not limited to but not limited to those described for substituents on alkyl moieties. Non-limiting examples of alkenyl groups include ethylene, methylethylene, isopropylidene, 1,2-ethane-diyl, 1,1-ethane-diyl, 1,3-propane-diyl, 1,2-propane-diyl, 1,3-butane-diyl, and 1,4-butane-diyl.

The term "alkynyl" refers to an unsaturated, acyclic hydrocarbon radical, linear or branched, in so much as it contains one or more triple bonds. The alkynyl group can be optionally substituted with any moiety that does not adversely affect the reaction process, including but not limited to those described above for alkyl moieties. Non-limiting examples of suitable alkynyl groups include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, and hexyn-3-yl, 3,3-dimethylbutyn-1-yl radicals.

The term "alkylamino" or "arylamino" refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis, and are described, for example, in Greene et al., Protective Groups in Organic Synthesis, supra.

The term "aryl", alone or in combination, means a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties. The aryl group can be optionally substituted with any moiety that does not adversely affect the process, including but not limited to but not limited to those described above for alkyl moieties. Non-limiting examples of substituted aryl include heteroarylamino, N-aryl-N-alkylamino, N-hetero arylamino-N-alkylamino, heteroaralkoxy, arylamino, aralkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydroxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from the group consisting of straight, branched, or cyclic alkyl or lower alkyl, alkoxyalkyl, including, but not limited to methoxymethyl, aralkyl, including, but not limited to, benzyl, aryloxyalkyl, such as phenoxymethyl, aryl, including, but not limited to, phenyl, optionally substituted with halogen (F, Cl, Br, or I), alkyl (including but not limited to $C_1$, $C_2$, $C_3$, and $C_4$) or alkoxy (including but not limited to $C_1$, $C_2$, $C_3$, and $C_4$), sulfonate esters such as alkyl or aralkyl sulphonyl, including but not limited to methanesulfonyl, the mono, di or triphosphate ester, trityl or monomethoxytrityl, substituted benzyl, trialkylsilyl (e.g., dimethyl-t-butylsilyl) and diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals.

Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

The terms "heteroaryl" or "heteroaromatic," as used herein, refer to an aromatic that includes at least one sulfur, oxygen, nitrogen or phosphorus in the aromatic ring.

The term "heterocyclic," "heterocyclyl," and cycloheteroalkyl refer to a nonaromatic cyclic group wherein there is at least one heteroatom, such as oxygen, sulfur, nitrogen, or phosphorus in the ring.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituents selected from the group consisting of halogen, haloalkyl, alkyl, alkoxy, hydroxy, carboxyl derivatives, amido, amino, alkylamino, and dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl. The heterocyclic or heteroaromatic group can be substituted with any moiety that does not adversely affect the reaction, including but not limited to but not limited to those described above for aryl.

The term "host," as used herein, refers to a unicellular or multicellular organism in which the virus can replicate, including but not limited to cell lines and animals, and, preferably, humans. Alternatively, the host can be carrying a part of the viral genome, whose replication or function can be altered by the compounds of the present invention. The term host specifically refers to infected cells, cells transfected with all or part of the viral genome and animals, in particular, primates (including but not limited to chimpanzees) and humans. In most animal applications of the present invention, the host is a human being. Veterinary applications, in certain indications, however, are clearly contemplated by the present invention (such as for use in treating chimpanzees).

The term "peptide" refers to a natural or synthetic compound containing two to one hundred amino acids linked by the carboxyl group of one amino acid to the amino group of another.

The term "pharmaceutically acceptable salt or prodrug" is used throughout the specification to describe any pharmaceutically acceptable form (such as an ester) compound which, upon administration to a patient, provides the compound. Pharmaceutically-acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art.

The term "pharmaceutically acceptable salt or prodrug" is used throughout the specification to describe any pharmaceutically acceptable form (such as an ester) compound which, upon administration to a patient, provides the compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on functional moieties of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. The prodrug forms of the compounds of this invention can possess antiviral activity, can be metabolized to form a compound that exhibits such activity, or both.

II. Active Compounds

The Hepatitis B virus (HBV) is an enveloped, partially double-stranded DNA (dsDNA) virus of the Hepadnavirus family (Hepadnaviridae). Its genome contains 4 overlapping reading frames: the precore/core gene; the polymerase gene; the L, M, and S genes, which encode for the 3 envelope proteins; and the X gene.

Upon infection, the partially double-stranded DNA genome (the relaxed circular DNA; rcDNA) is converted to a covalently closed circular DNA (cccDNA) in the nucleus of the host cell, and the viral mRNAs are transcribed. Once encapsidated, the pregenomic RNA (pgRNA), which also codes for core protein and Pol, serves as the template for reverse transcription, which regenerates the partially dsDNA genome (rcDNA) in the nucleocapsid.

Following hepatitis B infections, cccDNA can remain following clinical treatment in liver cells, and can reactivate. The relative quantity of cccDNA present is an indicator for HBV treatment (Bourne, et al., (January 2007). "Quantitative analysis of HBV cccDNA from clinical specimens: correlation with clinical and virological response during antiviral therapy". Journal of Viral Hepatitis 14 (1): 56-63).

A capsid is the protein shell of a virus, and includes oligomeric structural subunits made of proteins called protomers. The observable 3-dimensional morphological subunits, which may or may not correspond to individual proteins, are called capsomeres. The capsid encloses the genetic material of the virus.

In vivo, HBV capsids assemble around an RNA-reverse transcriptase complex. Assembly of the capsid is required for reverse transcription of the RNA pregenome to the mature DNA form. In HBV, the dominant form of capsid is composed of 120 copies of the capsid protein dimer. Even modest mutations of the capsid protein can have dramatic effects on the viability of progeny virus.

Most of the compounds described herein are active as capsid inhibitors. Inhibiting capsid assembly can reduce cccDNA, the main reservoir for HBV, and can also decrease the levels of HBV DNA, HBeAg and HBsAg.

In one embodiment, the compounds have the following formula:

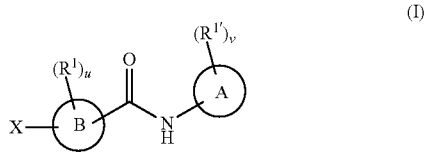

(I)

or a pharmaceutically acceptable salt or prodrug thereof, wherein

A is phenyl, a six-membered heteroaromatic ring containing one, two, or three nitrogen atoms, a five-membered heteroaromatic ring containing one, two, or three heteroatoms which are, independently, N, O, or S; a $C_{4-14}$ bicyclic ring, alkylheteroaryl, or alkylaryl;

B is a six or seven-membered ring or a six or seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a $C_{4-14}$ bicyclic ring, When $R^1$ and $R^{1'}$ are attached to a carbon, they are, independently, hydrogen, halogen (including F, Cl, Br, and I), $CF_3$, $SF_5$, hydroxy, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl;

When $R^1$ and $R^{1'}$ are attached to a nitrogen, they are, independently, hydrogen, $C_{2-6}$ alkoxy, $C_{3-6}$ alkoxyalkyl, $C_{2-6}$ alkenyl, alkoxycarbonyl, carbonylalkyl, carbonyl aryl, $C_{1-6}$ alkyl, heterocyclylalkyl, $C_{2-6}$ hydroxyalkyl, or $S(O)_2R'$;

Each R' is independently H, $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl, or if two R' reside on the same nitrogen atom, they can come together to form a $C_{3-6}$ ring optionally containing a N, O, or S heteroatom;

The R' groups can optionally be substituted with one or more substituents, which substituents are, independently, halo, $C_{1-6}$ haloalkyl, $C_{1-6}$ hydroxyalkyl, hydroxyl, carboxyl, acyl, aryl, acyloxy, amino, amido, carboxyl derivatives, alkylamino, dialkylamino, arylamino, alkoxy, alkoxyalkyl, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference;

u and v are independently 0, 1, 2, 3, 4 or 5;

X is

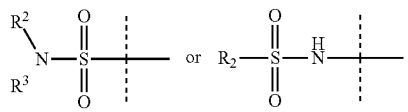

$R^3$ is H, $C_{1-6}$ alkyl, $C_{1-6}$ haloalkyl, $C_{2-6}$ alkenyl, or $C_{2-6}$ alkynyl, $R^2$ is $C_{1-6}$ alkyl, $C_{1-6}$ haloalkyl, $C_{2-8}$ alkoxyalkyl, $C_{2-6}$ alkenyl, $C_{2-6}$ alkynyl, aryl, such as phenyl, heteroaryl, including six-membered heteroaromatic rings containing one, two, or three nitrogen atoms and five-membered heteroaromatic rings containing one, two, or three heteroatoms, which, independently, are N, O, or S, alkylaryl, arylalkyl, a six-membered ring or a six-membered bridged or spiro-fused ring containing zero, one, or two heteroatoms which are, independently, N, O, or S, a seven-membered bridged or spiro-fused ring containing zero, one, or two heteroatoms which are, independently, N, O, or S, a five-membered ring containing zero, one, or two heteroatoms which are, independently, N, O, or S; a four-membered ring containing zero, one, or two heteroatoms which are, independently, N, O, or S; cycloalkyl, alkylheteroaryl, or alkylaryl;

$R^2$ is optionally substituted with one or more substituents, which each, independently, are halogen (including F, Cl, Br, and I), $CF_3$, $SF_5$, hydroxy, $N(R')S(O)_2R'$, $S(O)_2R'$, $S(O)_2N(R')_2$, $C_{1-6}$ alkoxy, $C_{1-6}$ haloalkoxy, cyano, azido, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl; or is substituted with aryl, substituted aryl, heteroaryl, or substituted heteroaryl, where substituents on the substituted aryl and substituted heteroaryl are selected from the group consisting of halogen, $SF_5$, $CF_3$, hydroxy, $N(R')S(O)_2R'$, $S(O)_2R'$, $S(O)_2N(R')_2$, $C(O)R'$, $C_{1-6}$ alkoxy, cyano, azido, $C_{2-6}$ alkynyl, $C_{3-6}$ alkoxyalkyl, alkoxycarbonyl, alkoxycarbonylalkyl, and $C_{1-6}$ alkyl.

$R^2$ and $R^3$ can come together with the nitrogen to which they are attached form a 6-10 membered bicyclic or bridged ring, a 3 to 8 saturated ring, or a 5 membered unsaturated ring; such bicyclic, bridged, saturated and unsaturated rings optionally containing one or more additional heteroatoms, where each is, independently, O, S or N, and optionally being substituted with one or more substituents, wherein each, independently, is halogen (including F, Cl, Br, I), $CF_3$, hydroxy, $N(R')S(O)_2R'$, $S(O)_2R'$, $S(O)_2N(R')_2$, $C_{1-6}$ alkoxy, cyano, azido, $C_{2-6}$ alkynyl, $C_{3-6}$ alkoxyalkyl, alkoxycarbonyl, alkoxycarbonylalkyl, C$_{1-6}$ alkyl, arylalkoxycarbonyl, carboxy, C$_{1-6}$ haloalkyl, heterocyclylalkyl, or C$_{1-6}$ hydroxyalkyl.

In a second embodiment, the compounds have the following formula:

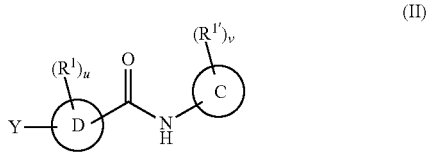

(II)

or a pharmaceutically acceptable salt or prodrug thereof, wherein

R$^1$ and R$^{1'}$ are as defined with respect to Formula I, u and v are independently 0, 1, 2, 3, 4 or 5;

C is phenyl, a six-membered heteroaromatic ring containing one, two, or three nitrogen atoms, a five-membered heteroaromatic ring containing one, two, or three heteroatoms which are, independently, N, O, or S; a C$_{4-14}$ bicyclic ring, alkylaryl, or alkylheteroaryl;

D is phenyl, a six-membered heteroaromatic ring containing one, two, or three nitrogen atoms, a five-membered heteroaromatic ring containing one, two, or three heteroatoms, which are, independently, N, O, or S, or a C$_{4-14}$ bicyclic ring, Y is

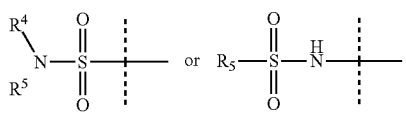

R$^4$ is H or C$_{1-6}$ alkyl, C$_{1-6}$ haloalkyl, C$_{2-6}$ alkenyl, C$_{2-6}$ alkynyl; in one embodiment, R$^4$ is C$_{1-6}$ alkyl, C$_{1-6}$ haloalkyl, C$_{2-6}$ alkenyl, C$_{2-6}$ alkynyl, where, in one embodiment, if C is phenyl, D is not phenyl or a 5-membered ring heteroaryl, and in another embodiment, if C is phenyl and D is phenyl or a 5-membered ring heteroaryl, then R$^5$ is not alkylaryl, alkenyl, or a six-membered bridged ring;

R$^5$ is alkylaryl, arylalkyl, C$_{2-6}$ alkenyl, C$_{2-6}$ alkynyl, aryl, such as phenyl, heteroaryl, including six-membered heteroaromatic rings containing one, two, or three nitrogen atoms and five-membered heteroaromatic rings containing one, two, or three heteroatoms, which, independently, are N, O, or S; and a six-membered bridged or spiro-fused ring containing zero, one, or two heteroatoms which are, independently, N, O, or S; in one embodiment, R$^5$ is alkylaryl, arylalkyl, phenyl, a five or six-membered heteroaryl, or a six-membered bridged or spiro-fused ring containing zero, one, or two heteroatoms which are, independently, N, O, or S;

R$^5$ is optionally substituted with one or more substituents, each of which is, independently, halogen (including F, Cl, Br, and I), CF$_3$, SF$_5$, hydroxy, N(R')S(O)$_2$R', S(O)$_2$R', S(O)$_2$N(R')$_2$, C$_{1-6}$ alkoxy, C$_{1-6}$ haloalkoxy, cyano, azido, C$_{2-6}$ alkynyl, C$_{3-6}$ alkoxyalkyl, alkoxycarbonyl, alkoxycarbonylalkyl, C$_{1-6}$ alkyl, cycloalkyl, arylalkoxycarbonyl, carboxy, C$_{1-6}$ haloalkyl, heterocyclylalkyl, or C$_{1-6}$ hydroxyalkyl; or is substituted with aryl, substituted aryl, heteroaryl, or substituted heteroaryl, where substituents on the substituted aryl and substituted heteroaryl are selected from the group consisting of halogen, SF$_5$, CF$_3$, hydroxy, N(R')S(O)$_2$R', S(O)$_2$R', S(O)$_2$N(R')$_2$, C(O)R', C$_{1-6}$ alkoxy, cyano, azido, C$_{2-6}$ alkynyl, C$_{3-6}$ alkoxyalkyl, alkoxycarbonyl, alkoxycarbonylalkyl, and C$_{1-6}$ alkyl;

or when Y is

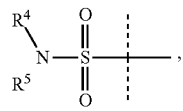

R$^4$ and R$^5$ together with the nitrogen to which they are attached form a 3 to 4 membered ring optionally substituted with one or more substituents, each of which is, independently, halogen (including F, Cl, Br, I), CF$_3$, hydroxy, N(R')S(O)$_2$R', S(O)$_2$R', S(O)$_2$N(R')$_2$, C$_{1-6}$ alkoxy, cyano, azido, C$_{2-6}$ alkynyl, C$_{3-6}$ alkoxyalkyl, alkoxycarbonyl, alkoxycarbonylalkyl, C$_{1-6}$ alkyl, arylalkoxycarbonyl, carboxy, C$_{1-6}$ haloalkyl, heterocyclylalkyl, or C$_{1-6}$ hydroxyalkyl.

In one embodiment of the compounds of Formula II, D is

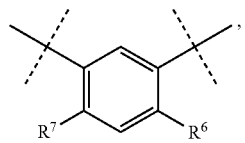

where R$^6$ is H, Cl, F or Br, and R$^7$ is H, methyl, F or Cl.

In one aspect of this embodiment, when Y is

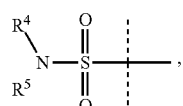

R$^5$ is not

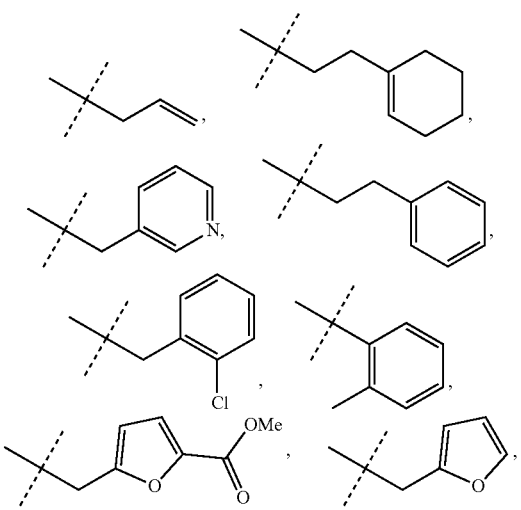

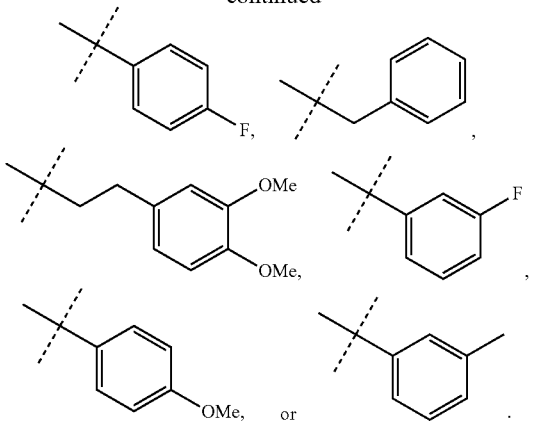

In another aspect of this embodiment, when $R^4$ is ethyl, then $R^5$ is not

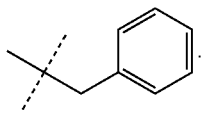

In one embodiment of the compounds of Formula II, C is a six-membered heteroaromatic ring containing one, two, or three nitrogen atoms, a five-membered heteroaromatic ring containing one, two, or three heteroatoms which are, independently, N, O, or S; a $C_{4-14}$ bicyclic ring, alkylaryl, or alkylheteroaryl.

In one embodiment of the compounds of Formula II, D is a $C_{4-14}$ bicyclic ring.

In another embodiment of the compounds of Formula II, $R^5$ is arylalkyl, $C_{2-6}$ alkynyl, aryl, such as phenyl, heteroaryl, including six-membered heteroaromatic rings containing one, two, or three nitrogen atoms and five-membered heteroaromatic rings containing one, two, or three heteroatoms, which, independently, are N, O, or S; and a six-membered spiro-fused ring containing zero, one, or two heteroatoms which are, independently, N, O, or S.

In a third embodiment, the compounds have the following formula:

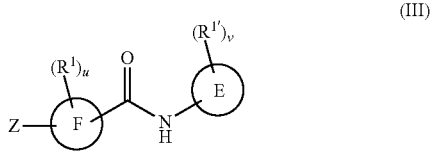

(III)

or a pharmaceutically acceptable salt or prodrug thereof, wherein $R^1$ and $R^{1'}$ are as defined with respect to Formula I, u and v are independently 0, 1, 2, 3, 4 or 5;

E is a six-membered heteroaromatic ring containing one, two, or three nitrogen atoms, a five-membered heteroaromatic ring containing one, two, or three heteroatoms, where each is, independently, N, O, or S; a $C_{4-14}$ bicyclic ring, alkylheteroaryl, or alkylaryl;

F is a five-membered heteroaromatic ring containing one, two, or three heteroatoms which are, independently, N, O, or S, or a $C_{4-14}$ bicyclic ring, Z is

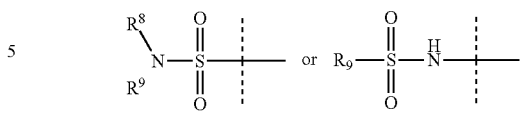

$R^8$ is H, $C_{1-6}$ alkyl, $C_{1-6}$ haloalkyl, $C_{2-6}$ alkenyl, or $C_{2-6}$ alkynyl, $R^9$ is $C_{1-6}$ alkyl, $C_{1-6}$ haloalkyl, $C_{2-8}$ alkoxyalkyl, a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring;

$R^9$ is optionally substituted with one or more substituents, each of which is independently halogen (including F, Cl, Br, and I), $CF_3$, $SF_5$, hydroxy, $N(R')S(O)_2R'$, $S(O)_2R'$, $S(O)_2N(R')_2$, $C_{1-6}$ alkoxy, $C_{1-6}$ haloalkoxy, cyano, azido, $C_{2-6}$ alkynyl, $C_{3-6}$ alkoxyalkyl, alkoxycarbonyl, alkoxycarbonylalkyl, $C_{1-6}$ alkyl, cycloalkyl, arylalkoxycarbonyl, carboxy, $C_{1-6}$ haloalkyl, heterocyclylalkyl, $C_{1-6}$ hydroxyalkyl; or is substituted with aryl, substituted aryl, heteroaryl, or substituted heteroaryl, where substituents on the substituted aryl and substituted heteroaryl are selected from the group consisting of halogen, $SF_5$, $CF_3$, hydroxy, $N(R')S(O)_2R'$, $S(O)_2R'$, $S(O)_2N(R')_2$, $C(O)R'$, $C_{1-6}$ alkoxy, cyano, azido, $C_{2-6}$ alkynyl, $C_{3-6}$ alkoxyalkyl, alkoxycarbonyl, alkoxycarbonylalkyl, and $C_{1-6}$ alkyl.

$R^8$ and $R^9$ can come together with the nitrogen to which they are attached form a 6-10 membered bicyclic or bridged ring or a 3 to 8 saturated ring; such bicyclic, bridged and saturated ring moiety optionally containing one or more additional heteroatoms which, independently, are O, S or N and optionally being substituted with one or more substituents, each, independently, is halogen (including F, Cl, Br, and I), $CF_3$, hydroxy, $N(R')S(O)_2R'$, $S(O)_2R'$, $S(O)_2N(R')_2$, $C_{1-6}$ alkoxy, cyano, azido, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl.

In a fourth embodiment, the compounds have the following formula:

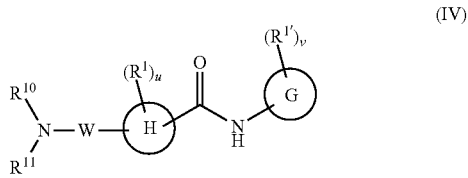

(IV)

or a pharmaceutically acceptable salt or prodrug thereof, wherein

G is phenyl, a six-membered heteroaromatic ring containing one, two, or three nitrogen atoms, a five-membered heteroaromatic ring containing one, two, or three heteroatoms, which are, independently, N, O, or S; a $C_{4-14}$ bicyclic ring, alkylheteroaryl, or alkylaryl;

H is phenyl, a six-membered heteroaromatic ring containing one, two, or three nitrogen atoms, a six-membered non-aromatic ring optionally containing one, two, or three heteroatoms, which are, independently, N, O, or S; or a $C_{4-14}$ bicyclic ring;

When $R^1$ and $R^{1'}$ are attached to a carbon they are, independently, hydrogen, halogen (including F, Cl, Br, and I), $CF_3$, $SF_5$, hydroxy, $N(R')S(O)_2R'$, $S(O)_2R'$, $S(O)_2N(R')_2$, $C_{1-6}$ alkoxy, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl;

When $R^1$ and $R^{1'}$ are attached to a nitrogen they are, independently, hydrogen, $C_{1-6}$ alkoxy, $C_{3-6}$ alkoxyalkyl, alkoxycarbonyl, carbonylalkyl, carbonyl aryl, $C_{1-6}$ alkyl, $C_{2-6}$ alkynyl, $C_{2-6}$ alkenyl, heterocyclylalkyl, $C_{1-6}$ hydroxyalkyl, or $S(O)_2R'$;

Each R' is independently H, $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl, or if two R' reside on the same nitrogen atom they can come together to form a $C_{3-6}$ alkyl ring optionally containing a N, O, or S; wherein the R' groups can be substituted with one or more substituents as defined above, for example, $C_{1-6}$ hydroxyalkyl, aminoalkyl, and alkoxyalkyl;

u and v are independently 0, 1, 2, 3, 4 or 5;

W is

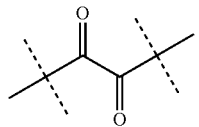

$R^{10}$ is H, $C_{1-6}$ alkyl, $C_{1-6}$ haloalkyl, $C_{2-6}$ alkenyl, or $C_{2-6}$ alkynyl, $R^{11}$ is $C_{1-6}$ alkyl, $C_{1-6}$ haloalkyl, $C_{2-8}$ alkoxyalkyl, $C_{2-6}$ alkenyl, $C_{2-6}$ alkynyl, aryl, heteroaryl, alkylaryl, arylalkyl, phenyl, a six-membered heteroaromatic ring containing one, two, or three nitrogen atoms, a six-membered ring or a six-membered bridged or spiro-fused ring containing zero, one, or two heteroatoms, which are, independently, N, O, or S, a seven-membered bridged or spiro-fused ring containing zero, one, or two heteroatoms, which are, independently, N, O, or S, a five-membered heteroaromatic ring containing one, two, or three heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S; a three membered ring, alkylheteroaryl, or alkylaryl;

wherein $R^{11}$ is optionally substituted with one or more substituents selected from the group consisting of halogen (including F, Cl, Br, and I), $SF_5$, $CF_3$, hydroxy, $N(R')S(O)_2R'$, $S(O)_2R'$, $S(O)_2N(R')_2$, $C_{1-6}$ alkoxy, $C_{1-6}$ haloalkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, $C_{1-6}$ hydroxyalkyl, aryl, substituted aryl, heteroaryl, and substituted heteroaryl, where substituents on the substituted aryl and substituted heteroaryl are selected from the group consisting of halogen, $SF_5$, $CF_3$, hydroxy, $N(R')S(O)_2R'$, $S(O)_2R'$, $S(O)_2N(R')_2$, $C(O)R'$, $C_{1-6}$ alkoxy, cyano, azido, alkynyl, $C_{3-6}$ alkoxyalkyl, alkoxycarbonyl, alkoxycarbonylalkyl, and $C_{1-6}$ alkyl; or $R^{10}$ and $R^{11}$ can come together with the nitrogen to which they are attached form a 6-10 membered bicyclic or bridged ring or a 3 to 8 saturated ring; such bicyclic, bridged or saturated ring moiety optionally containing one or more additional heteroatoms, which are each, independently, O, S or N, and optionally substituted with one or more substituents, each of which is, independently, halogen (including F, Cl, Br, and I), $CF_3$, hydroxy, $N(R')S(O)_2R'$, $S(O)_2R'$, $S(O)_2N(R')_2$, $C_{1-6}$ alkoxy, cyano, azido, alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl.

In a fifth embodiment, the compounds have the following formula:

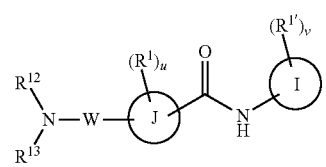

(V)

or a pharmaceutically acceptable salt or prodrug thereof, wherein $R^1$ and $R^{1'}$ are as defined with respect to Formula I, u and v are independently 0, 1, 2, 3, 4 or 5;

I is phenyl, a six-membered heteroaromatic ring containing one, two, or three nitrogen atoms, a five-membered heteroaromatic ring containing one, two, or three heteroatoms, which are, independently, N, O, or S, a $C_{4-14}$ bicyclic ring; alkylheteroaryl, or alkylaryl;

J is a five-membered heteroaromatic ring containing one, two, or three heteroatoms, which are, independently, N, O, or S, a six or seven-membered ring or a six or seven-membered bridged or spiro-fused ring containing zero, one, or two heteroatoms which are, independently, N, O, or S, a five-membered ring containing zero, one, or two heteroatoms which are, independently, N, O, or S; or a four-membered ring containing zero, one, or two heteroatoms which are, independently, N, O, or S, W is

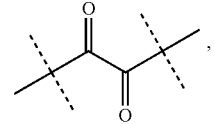, $R^{12}$ is H, $C_{1-6}$ alkyl, $C_{1-6}$ haloalkyl, $C_{2-6}$ alkenyl, or $C_{2-6}$ alkynyl, $R^{13}$ is $C_{2-6}$ alkenyl, $C_{2-6}$ alkynyl, aryl, including phenyl, heteroaryl, including six-membered heteroaromatic rings containing one, two, or three nitrogen atoms and five-membered heteroaromatic rings containing one, two, or three heteroatoms, which are, independently, N, O, or S; alkylaryl, arylalkyl, a $C_{4-14}$ bicyclic ring; a six-membered bridged or spiro-fused ring containing zero, one, or two heteroatoms which are, independently, N, O, or S, $R^{13}$ is optionally substituted with one or more substituents each independently selected from the group consisting of hydrogen, halogen (F, Cl, Br, I), $CF_3$, $SF_5$, hydroxy, $N(R')S(O)_2R'$, $S(O)_2R'$, $S(O)_2N(R')_2$, $C(O)R'$, $C_{1-6}$ alkoxy, $C_{1-6}$ haloalkoxy, cyano, azido, $C_{2-6}$ alkynyl, $C_{3-6}$ alkoxyalkyl, alkoxycarbonyl, alkoxycarbonylalkyl, $C_{1-6}$ alkyl, cycloalkyl, arylalkoxycarbonyl, carboxyl, haloalkyl, heterocyclylalkyl, and $C_{1-6}$ hydroxyalkyl; or is optionally substituted with aryl, substituted aryl, heteroaryl, or substituted heteroaryl, where substituents on the substituted aryl and substituted heteroaryl are selected from the group consisting of halogen, $CF_3$, hydroxy, $N(R')S(O)_2R'$, $S(O)_2R'$, $S(O)_2N(R')_2$, $C(O)R'$, $C_{1-6}$ alkoxy, cyano, azido, $C_{2-6}$ alkynyl, $C_{3-6}$ alkoxyalkyl, alkoxycarbonyl, alkoxycarbonylalkyl, and $C_{1-6}$ alkyl;

or $R^{12}$ and $R^{13}$ together with the nitrogen to which they are attached form a 3 to 4 membered ring optionally substituted with one or more substituents each independently selected from the group consisting of hydrogen, halogen (F, Cl, Br, I), $CF_3$, hydroxy, $N(R')S(O)_2R'$, $S(O)_2R'$, $S(O)_2N(R')_2$, $C_{1-6}$ alkoxy, cyano, azido, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, and $C_{1-6}$ hydroxyalkyl.

In a sixth embodiment, the compounds have the following formula:

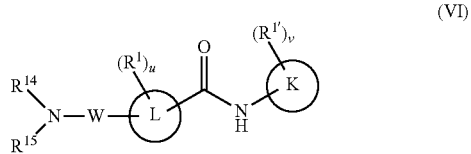

(VI)

or a pharmaceutically acceptable salt or prodrug thereof, wherein $R^1$ and $R^{1'}$ are as defined with respect to Formula I, u and v are independently 0, 1, 2, 3, 4 or 5;

K is a six-membered heteroaromatic ring containing one, two, or three nitrogen atoms, a five-membered heteroaromatic ring containing one, two, or three heteroatoms which are, independently, N, O, or S; a $C_{4-14}$ bicyclic ring, alkylheteroaryl, or alkylaryl;

L is a five-membered heteroaromatic ring containing one, two, or three heteroatoms which are, independently, N, O, or S, a six or seven-membered ring or a six or seven-membered bridged or spiro-fused ring containing zero, one, or two heteroatoms which are, independently, N, O, or S, a five-membered ring containing zero, one, or two heteroatoms which are, independently, N, O, or S; a four-membered ring containing zero, one, or two heteroatoms which are, independently, N, O, or S, or a $C_{4-14}$ bicyclic ring, W is

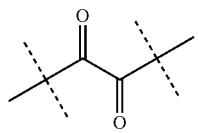

$R^{14}$ is H, $C_{1-6}$ alkyl, $C_{1-6}$ haloalkyl, $C_{2-6}$ alkenyl, or $C_{2-6}$ alkynyl, $R^{15}$ is $C_{1-6}$ alkyl, $C_{1-6}$ haloalkyl, $C_{2-8}$ alkoxyalkyl, a six-membered ring or a six-membered bridged or spiro-fused ring containing zero, one, or two heteroatoms which are, independently, N, O, or S, a seven-membered bridged or spiro-fused ring containing zero, one, or two heteroatoms which are, independently, N, O, or S, a five-membered ring containing zero, one, or two heteroatoms which are, independently, N, O, or S; a four-membered ring containing zero, one, or two heteroatoms which are, independently, N, O, or S;

$R^{15}$ is optionally substituted with one or more substituents which are, independently, halogen (F, Cl, Br, I), $SF_5$, $CF_3$, hydroxy, $N(R')S(O)_2R'$, $S(O)_2R'$, $S(O)_2N(R')_2$, $C_{1-6}$ alkoxy, $C_{1-6}$ haloalkoxy, cyano, azido, $C_{2-6}$ alkynyl, $C_{3-6}$ alkoxyalkyl, alkoxycarbonyl, alkoxycarbonylalkyl, $C_{1-6}$ alkyl, cycloalkyl, arylalkoxycarbonyl, carboxy, $C_{1-6}$ haloalkyl, heterocyclylalkyl, and $C_{1-6}$ hydroxyalkyl; or is substituted with aryl, substituted aryl, heteroaryl, or substituted heteroaryl, where substituents on the substituted aryl and substituted heteroaryl are selected from the group consisting of halogen, $SF_5$, $CF_3$, hydroxy, $N(R')S(O)_2R'$, $S(O)_2R'$, $S(O)_2N(R')_2$, $C(O)R'$, $C_{1-6}$ alkoxy, cyano, azido, $C_{2-6}$ alkynyl, $C_{3-6}$ alkoxyalkyl, alkoxycarbonyl, alkoxycarbonylalkyl, and $C_{1-6}$ alkyl, or $R^{14}$ and $R^{15}$ can come together with the nitrogen to which they are attached form a 6-10 membered bicyclic or bridged ring or a 3 to 8 saturated ring; such bicyclic, bridged and saturated ring moiety optionally containing one or more additional heteroatoms which are, independently, O, S or N, and optionally being substituted with one or more substituents each independently selected from the group consisting of halogen (including F, Cl, Br, and I), $CF_3$, hydroxy, $N(R')S(O)_2R'$, $S(O)_2R'$, $S(O)_2N(R')_2$, $C_{1-6}$ alkoxy, cyano, azido, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, and $C_{1-6}$ hydroxyalkyl.

In a seventh embodiment, the compounds have the following formula:

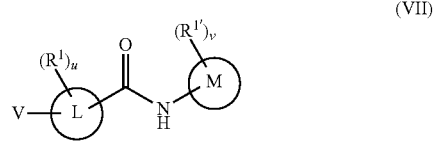

(VII)

or a pharmaceutically acceptable salt or prodrug thereof, wherein $R^1$ and $R^{1'}$ are as defined with respect to Formula I, u and v are independently 0, 1, 2, 3, 4 or 5;

M is phenyl, a six-membered heteroaromatic ring containing one, two, or three nitrogen atoms, a five-membered heteroaromatic ring containing one, two, or three heteroatoms which are, independently, N, O, or S, a $C_{4-14}$ bicyclic ring, alkylheteroaryl, or alkylaryl, N is phenyl, a six-membered heteroaromatic ring containing one, two, or three nitrogen atoms, a five-membered heteroaromatic ring containing one, two, or three heteroatoms independently selected from N, O, and S, a six or seven-membered ring or a six or seven-membered bridged or spiro-fused ring containing zero, one, or two heteroatoms which are, independently, N, O, or S, a five-membered ring containing zero, one, or two heteroatoms which are, independently, N, O, or S; a four-membered ring containing zero, one, or two heteroatoms which are, independently, N, O, or S; or a $C_{4-14}$ bicyclic ring, V is

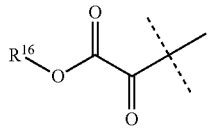 or 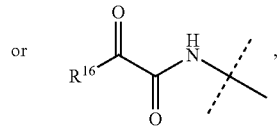, and

R¹⁶ is $C_{1-6}$ alkyl, $C_{1-6}$ haloalkyl, $C_{2-8}$ alkoxyalkyl, $C_{2-6}$ alkenyl, $C_{2-6}$ alkynyl, aryl, such as phenyl, heteroaryl, such as a six-membered heteroaromatic ring containing one, two, or three nitrogen atoms or a five-membered heteroaromatic ring containing one, two, or three heteroatoms which are, independently, N, O, or S; a six-membered ring or a six-membered bridged or spiro-fused ring containing zero, one, or two heteroatoms which are, independently, N, O, or S, a five-membered ring containing zero, one, or two heteroatoms which are, independently, N, O, or S; a four-membered ring containing zero, one, or two heteroatoms which are, independently, N, O, or S; alkylaryl, arylalkyl, alkylheteroaryl, or alkylaryl, wherein $R^{16}$ is optionally substituted with one or more substituents selected from the group consisting of halogen (including F, Cl, Br, and I), $SF_5$, $CF_3$, hydroxy, $N(R')S(O)_2R'$, $S(O)_2R'$, $S(O)_2N(R')_2$, $C_{1-6}$ alkoxy, $C_{1-6}$ haloalkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, $C_{1-6}$ hydroxyalkyl, aryl, substituted aryl, heteroaryl, and substituted heteroaryl, where substituents on the substituted aryl and substituted heteroaryl are selected from the group consisting of halogen, $SF_5$, $CF_3$, hydroxy, $N(R')S(O)_2R'$, $S(O)_2R'$, $S(O)_2N(R')_2$, $C(O)R'$, $C_{1-6}$ alkoxy, cyano, azido, $C_{2-6}$ alkynyl, $C_{3-6}$ alkoxyalkyl, alkoxycarbonyl, alkoxycarbonylalkyl, and $C_{1-6}$ alkyl.

Representative compounds falling within the scope of the invention include the following:

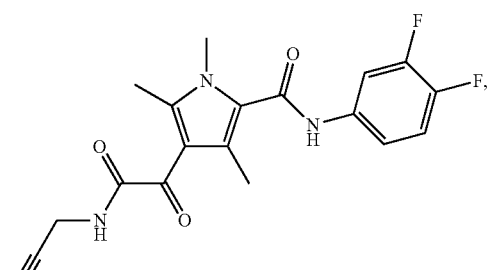

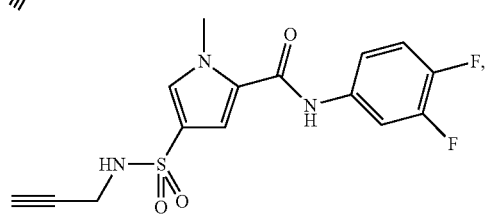

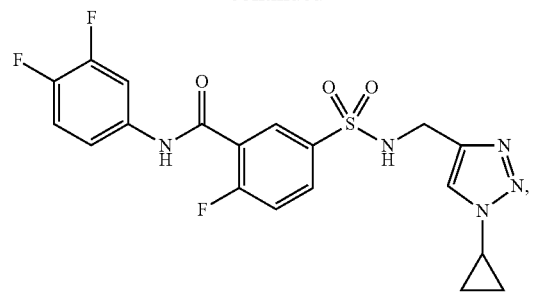

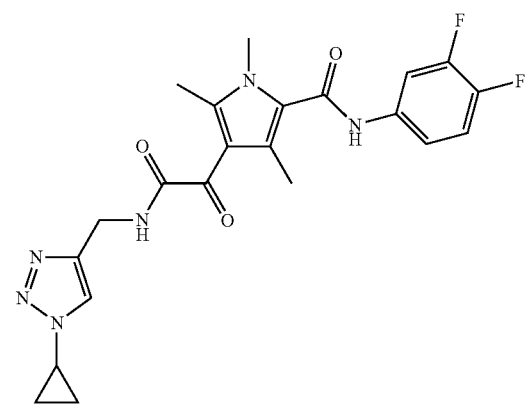

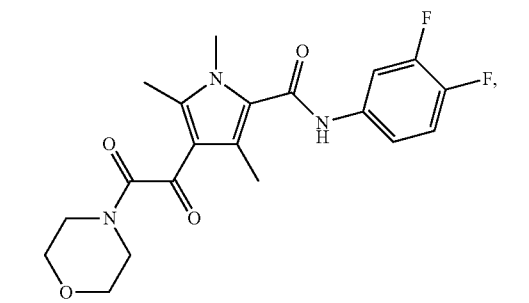

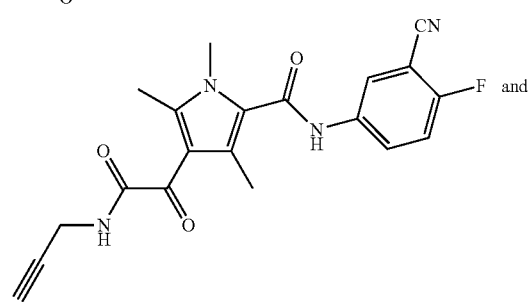

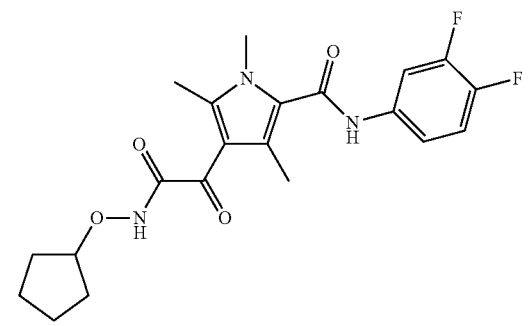

and pharmaceutically acceptable salts or prodrugs thereof.

Representative compounds also include:
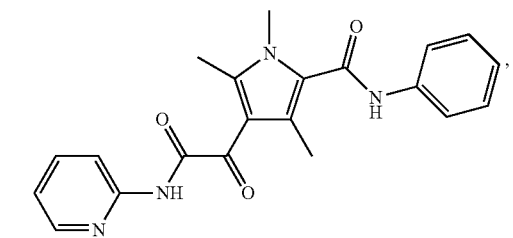
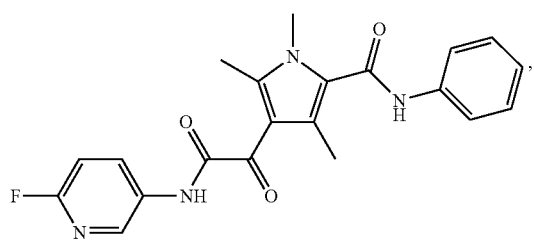
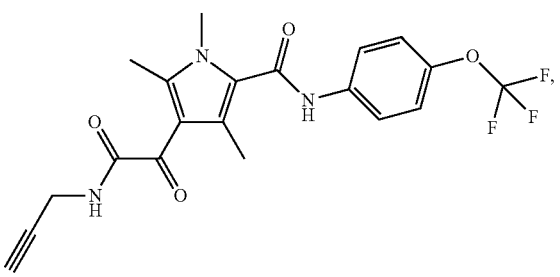
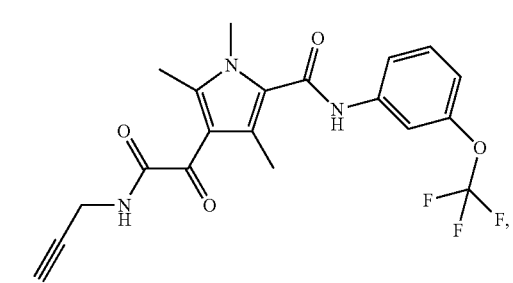
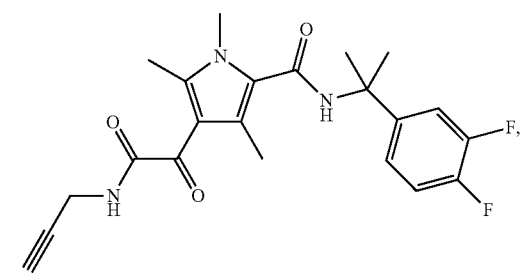
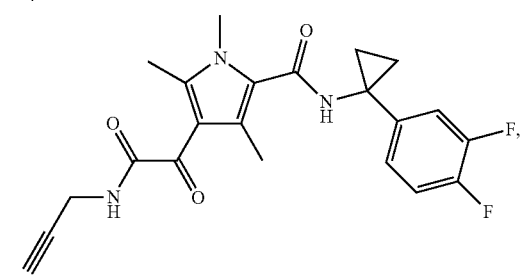
-continued
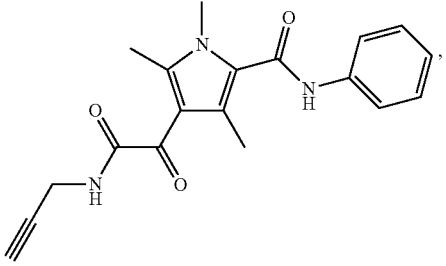
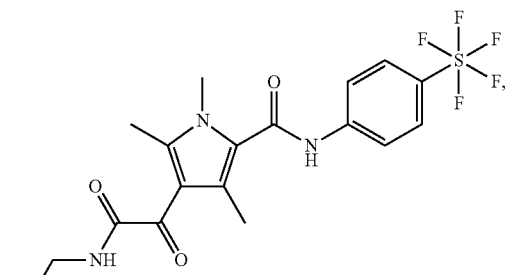
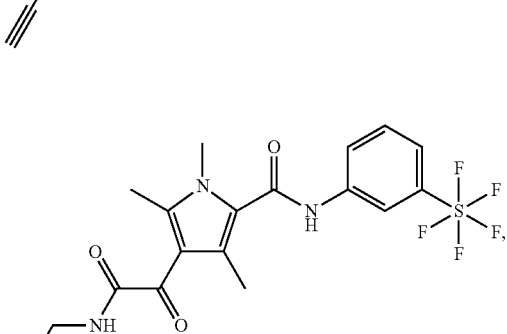
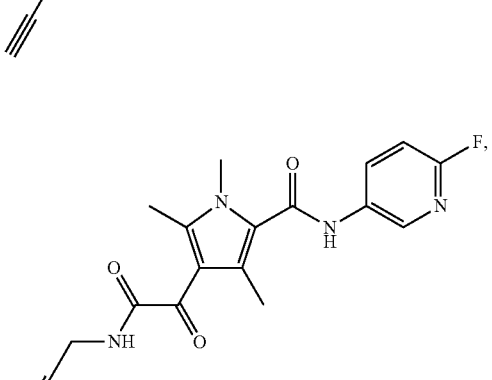
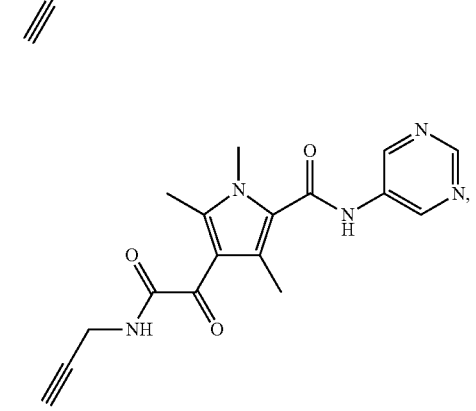

-continued
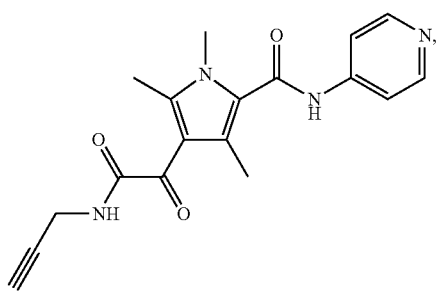
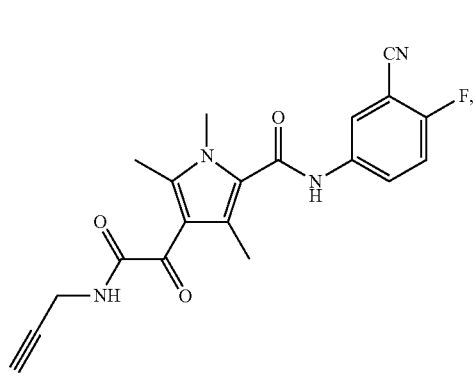
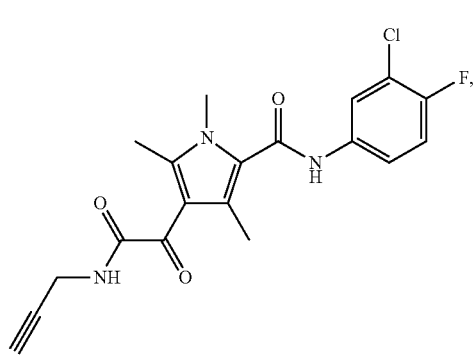
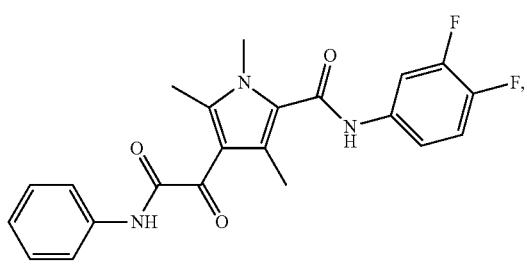
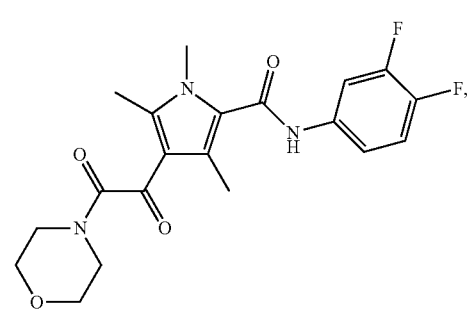
-continued
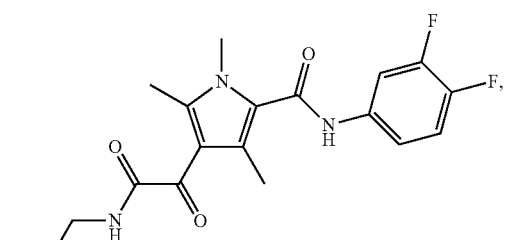
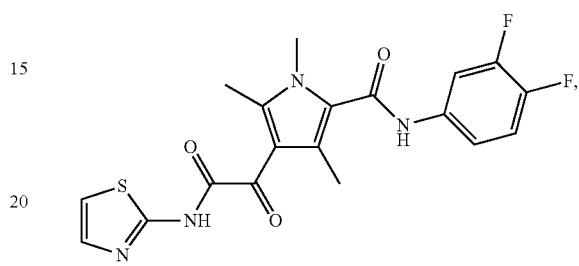
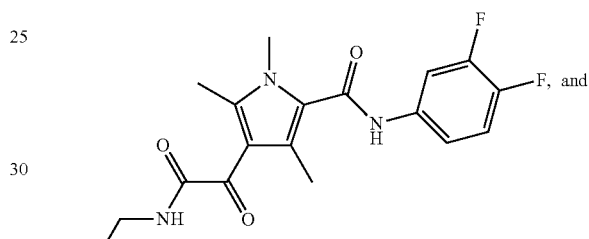
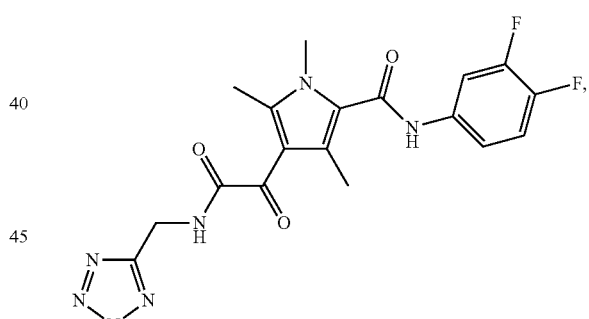
and pharmaceutically acceptable salts and prodrugs thereof.
Particularly preferred compounds include:
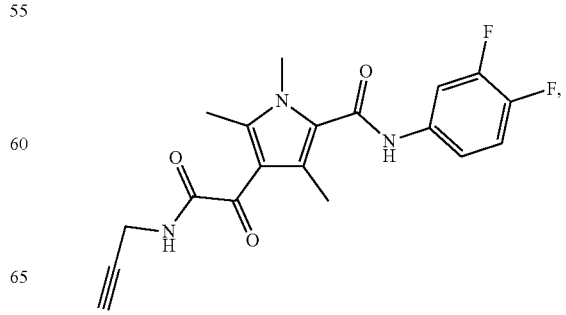

-continued

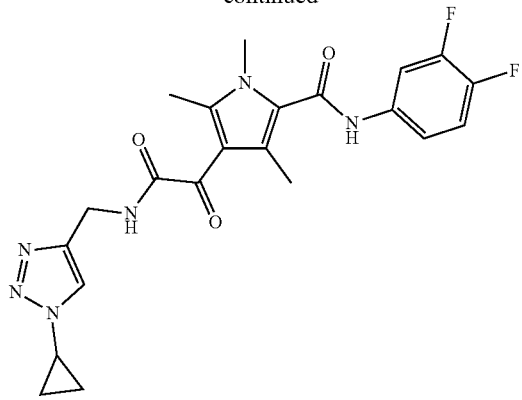

or a pharmaceutically acceptable salt or prodrug thereof.

A particularly preferred compound has the formula:

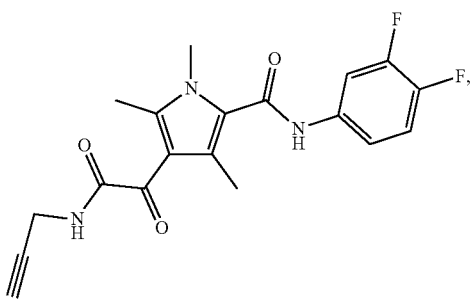 [SMILES: C#CCNC(=O)C(=O)c1c(C)c(C(=O)Nc2ccc(F)c(F)c2)n(C)c1C]

or a pharmaceutically acceptable salt thereof.

III Stereoisomerism and Polymorphism

The compounds described herein can have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism. The present invention encompasses racemic, optically-active, polymorphic, or stereoisomeric forms, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective compound, then derivatize the compound to form the compounds described herein, or purify the compound themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

IV. Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts can also be formed, including but not limited to, sulfate, nitrate, bicarbonate and carbonate salts. For certain transdermal applications, it can be preferred to use fatty acid salts of the compounds described herein. The fatty acid salts can help penetrate the stratum corneum. Examples of suitable salts include salts of the compounds with stearic acid, oleic acid, lineoleic acid, palmitic acid, caprylic acid, and capric acid.

Pharmaceutically acceptable salts can be obtained using standard procedures well known in the art, for example by reacting a sufficiently basic compound such as an amine with a suitable acid, affording a physiologically acceptable anion. In those cases where a compound includes multiple amine groups, the salts can be formed with any number of the amine groups. Alkali metal (e.g., sodium, potassium or lithium) or alkaline earth metal (e.g., calcium) salts of carboxylic acids can also be made.

A prodrug is a pharmacological substance that is administered in an inactive (or significantly less active) form and subsequently metabolized in vivo to an active metabolite. Getting more drug to the desired target at a lower dose is often the rationale behind the use of a prodrug and is generally attributed to better absorption, distribution, metabolism, and/or excretion (ADME) properties. Prodrugs are usually designed to improve oral bioavailability, with poor absorption from the gastrointestinal tract usually being the limiting factor. Additionally, the use of a prodrug strategy can increase the selectivity of the drug for its intended target thus reducing the potential for off target effects.

V. Isotopes

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. In other embodiments are examples of isotopes that are incorporated into the present compounds including isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^{2}H$ are incorporated, are useful in drug and/or substrate tissue distribution assays. Further, in some embodiments, substitution with isotopes such as deuterium, i.e., $^{2}H$, can affords certain therapeutic advantages resulting from greater metabolic stability, such as, for example, increased in vivo half-life or reduced dosage requirements.

VI. Methods of Treatment

The compounds described herein can be used to prevent, treat or cure hepatitis B virus (HBV) infections and West Nile virus infections.

Hosts, including but not limited to humans, suffering from one of these cancers, or infected with one of these viruses, such as HBV, or a gene fragment thereof, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, transdermally, subcutaneously, or topically, in liquid or solid form.

The compounds and compositions described herein can also be used to treat other viral diseases. For example, by curing, controlling, or eliminating HBV, HDV infection can also be suppressed or eliminated. Sheldon et al., "Does treatment of hepatitis B virus (HBV) infection reduce hepatitis delta virus (HDV) replication in HIV-HBV-HDV-coinfected patients?" Antivir Ther. 2008; 13(1):97-102).

Hepatitis delta virus (HDV) has a unique replication process that requires coinfection with hepatitis B virus (HBV). While treatment is believed to be currently limited to interferon therapy, patients undergoing successful anti-HBV therapy with the compounds described herein can indirectly benefit from suppression of HDV replication. A significant and sustained reduction in serum HDV RNA can be obtained by reducing the HBV covalently closed circular DNA (cccDNA). cccDNA in HBV is formed by conversion of capsid-associated relaxed circular DNA (rcDNA). Guo et al., "Characterization of the intracellular deproteinized relaxed circular DNA of hepatitis B virus: an intermediate of covalently closed circular DNA formation". J Virol. 81 (22): 12472-12484 (November 2007). Accordingly, inhibition of capsid formation using the compounds described herein can also suppress or eliminate HDV replication.

Further, there is a subset of HCV patients which have also been earlier infected with HBV, and the HBV is dormant at the time the HCV is being treated. in some of these patients, successful treatment of HCV (for example, with Harvoni/Sovaldi) can reactivate the dormant HBV infection. Co-administration of the compounds described herein, along with HCV treatment, can prevent the reactivation of the dormant HBV infection, or treat the reactivated HBV infection.

VII. Combination of Alternation Therapy

In one embodiment, the compounds of the invention can be employed together with at least one other antiviral agent, including, but not limited to, polymerase inhibitors, anti-HBV nucleosides and their prodrugs, viral entry inhibitor, viral maturation inhibitor, literature described capsid assembly modulator, IMPDH inhibitors, protease inhibitors, immune-based therapeutic agents, reverse transcriptase inhibitor, a TLR-agonist, and agents of distinct or unknown mechanism. They can also be used in conjunction with CRISPR/CAS9 approaches using AAV as the human delivery vector.

For example, when used to treat or prevent HBV infection, the active compound or its prodrug or pharmaceutically acceptable salt can be administered in combination or alternation with another anti-HBV agent including, but not limited to, those of the formula above. In general, in combination therapy, effective dosages of two or more agents are administered together, whereas during alternation therapy, an effective dosage of each agent is administered serially. The dosage will depend on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include those in the tables below.

| Hepatitis B Therapies | | |
|---|---|---|
| FAMILY/DRUG NAME | MECHANISM | COMPANY/ STATUS |
| Intron A (Interferon alfa-2b) | Immunomodulator | Merck, Whitehouse Station, NJ Approved |
| Pegasys (Peginterferon alfa-2a) | Immunomodulator | Genentech, South San Francisco, CA Approved |
| Epivir-HBV (Lamivudine) | Inhibits viral DNA polymerase | GlaxoSmithKline, Philadelphia, PA Approved |
| Hepsera (Adefovir Dipivoxil) | Inhibits viral DNA polymerase | Gilead Sciences, Foster City, CA Approved |
| Baraclude (Entecavir) | Inhibits viral DNA polymerase | Bristol-Myers Squibb, Princeton, NJ Approved |
| Tyzeka (Telbivudine) | Inhibits viral DNA polymerase | Novartis, Switzerland Approved |
| Viread (Tenofovir) | Inhibits viral DNA polymerase | Gilead Sciences, Foster City, CA Approved |
| Clevudine (L-FMAU) | Inhibits viral DNA polymerase | Bukwang, South Korea Eisai, Japan Approved S. Korea 2006 (Levovir) |
| Tenofovir alafenamide (TAF) | Prodrug of Tenofovir | Gilead Sciences, Foster City, CA Phase III |
| CMX157 | Prodrug of Tenofovir | ContraVir Pharmaceuticals, Edison, NJ Phase II |
| AGX-1009 | Prodrug of Tenofovir | Agenix, Australia Phase I, China |
| Myrcludex B | Entry Inhibitor | Hepatera, Russia with Myr-GmbH, Germany Phase II for HBV and HDV |
| ARC520 | RNAi gene silencer | Arrowhead Research, Pasadena, CA Phase II/III |
| NVR 3-778 | Capsid inhibitor | Novira Therapeutics, Doylestown, PA Phase IIa |
| Morphothiadine mesilate (GLS4) | Capsid inhibitor | Sunshine Lake Pharma of HEC, China Phase II |
| ISIS-HBVRx | Antisense drug | ISIS Pharma (w/ GSK), Carlsbad, CA Phase II |
| SB 9200 HBV | Small molecule nucleic acid hybrids or "SMNH" | Spring Bank Pharma, Milford, MA Phase II |
| Rep 2139-Ca | HBsAg release inhibitor | REPLICor Inc., Canada Phase II |
| Bay 41-4109 | Capsid Inhibitor | AiCuris, Germany Phase I |
| TKM-HBV | RNAi gene silencer | Tekmira, Canada Phase I |
| Alinia (Nitazoxanide) | Small molecule | Romark Labs, Tampa, FL Preclinical |
| CpAMS | HBV Core Protein | Assembly Biosciences, NY NY Preclinical |
| ALN-HBV | RNAi gene silencer | Alnylam, Cambridge, MA PreclinicaL |
| CPI-431-32 | Cyclophilin inhibitor | Ciclofilin Pharma, San Diego, CA Preclinical |
| Hepharna | RNAi gene silencing | Benitec, Australia Preclinical |
| OCB-030 | Cyclophilin inhibitor | Arbutus Biopharma (formerly Tekmira), Canada Preclinical |
| GS-9620 | TLR7 agonist | Gilead Sciences, Foster City, CA Phase II |
| RG7795 formerly ANA773) | TLR7 agonist | Roche, Switzerland Phase II |
| CYT107 (Interleukin-7) | Immunomodulator | Cytheris, France Phase I/IIa |
| NCT01641536 | Therapeutic vaccine | Ichor Medical Systems (w/Janssen), San Diego, CA Phase I |
| TG 1050 | Immunotherapeutic | Transgene, Shanghai Phase I |
| CYT-003 | TLR9 agonist | Arbutus Biopharma (formerly Tekmira), Canada Preclinical |
| ARB 1467 | TKM-HBV | Arbutus Biopharma (formerly Tekmira), Canada Preclinical |
| ARB-1468 | TKM-HBV | Airbutus Biopharma (formerly Tekmira), Canada Preclinical |

Additional Anti-HBV Treatments which can be Used in Combination or Alternation

In addition to the compounds described herein, which can function by inhibiting cccDNA, and the combination therapies described above, which combine the compounds described herein with approved anti-HBV drugs such as TAF, approaches like siRNA, shRNA, Talens, Crisper/Cas9, and mir (microRNA) compounds can also be used.

siRNA and shRNA Therapy siRNA therapy for treating HBV is described, for example, in Chen and Mahato, "siRNA Pool Targeting Different Sites of Human Hepatitis B Surface Antigen Efficiently Inhibits HBV Infection;" J Drug Target. 2008 February; 16(2): 140-148 and Morrissey et al., "Potent and persistent in vivo anti-HBV activity of chemically modified siRNAs," Nature Biotechnology 23, 1002-1007 (2005).

RNAi is a sequence-specific, post-transcriptional gene silencing mechanism, which is triggered by double-stranded synthetic siRNA or short hairpin RNA (shRNA) expressed intracellularly from a vector. HBV replication and expression can be inhibited by administration of synthetic siRNAs or endogenously expressed shRNAs. See, for example, Giladi et al., "Small interfering RNA inhibits hepatitis B virus replication in mice," Mol Ther. 2003; 8(5):769-76; McCaffrey et al., "Inhibition of hepatitis B virus in mice by RNA interference," Nat Biotechnol. 2003; 21(6):639-44; and Shlomai and Shaul, "Inhibition of hepatitis B virus expression and replication by RNA interference," Hepatology. 2003; 37(4):764-70). HBV gene silencing may depend, for example, on siRNA dosing and sequences, and targets for gene silencing include, for example, the inhibition of virus replication, and suppression of HBsAg expression.

In one embodiment, a combination of several siRNAs and/or shRNAs are used, targeting two or more of the HBV S, C, P and X genes. In this manner, multiple targets for inhibition of HBV replication and gene expression can be accessed.

Once an appropriate target has been identified, for example, the human hepatitis B virus surface antigen (HBsAg) (Gene Bank Accession #NM_U95551), siRNAs can be designed according to the guide provided by Ambion (http://www.ambion.com/techlib/misc/siRNA_finder.html) and Invitrogen (https://rnaidesigner.invitrogen.com/rnaiexpress/design.do). The sequence specificity of siRNAs can be checked by performing a BLAST search (www.ncbi.nlm.nih.gov).

Once siRNA sequences are identified, they can be converted into shRNAs. To express shRNA, control vectors can be constructed, for example, using psiSTRIKE™, which is a linearized plasmid and contains a U6 RNA polymerase promoter. These shRNAs contain two complementary oligonucleotides that can be annealed to form double-stranded DNA for ligation into psiSTRIKE™ vector corresponding sites, under a suitable promoter, such as the U6 promoter, using an appropriate ligase, such as T4 DNA ligase. Plasmids can be purified, for example, using the QIAGEN® Plasmid Mini Kit (QIAGEN, Valencia, Calif.).

Talens/CRISPR

As discussed above, chronic HBV viral infections often persist due to the presence of long-lived forms of viral DNA in infected cells. Current therapies can suppress viral replication, but have little or no effect on long-lived DNA forms, so viral replication resumes as soon as therapy is stopped.

In addition to targeting long-lived DNA forms using the capsid inhibitors described herein, targeted endonucleases, such as homing endonucleases, zinc-finger nucleases (ZFNs), transcription activator-like effector nucleases (TALENs), and the CRISPR (clustered regularly interspaced short palindromic repeats) system can be used. The use of TALENS to target HBV is described, for example, in Weber et al., "TALENs Targeting HBV: Designer Endonuclease Therapies for Viral Infections," Molecular Therapy (2013); 21 10, 1819-1820; http://www.nature.com/mt/journal/v21/n10/full/mt2013208a.html These nucleases function by specifically recognizing and cleaving selected DNA sequences, which results in gene disruption upon imprecise DNA repair. TALENs targeting of the hepatitis B virus (HBV) genome can result in TALEN-induced mutations in the long-lived HBV covalently closed circular DNA (cccDNA). Mutation and/or disruption of cccDNA prevents viral replication by blocking expression of functional viral proteins.

CRISPR

CRISPR, or clustered regularly interspaced short palindromic repeats, is another way to mutate HBV DNA, by providing targeted genome editing. In addition to the programmable editing tools, such as zinc finger nucleases and transcription activator-like effector nucleases (TALENs) described above, CRISPR (clustered regularly interspaced short palindromic repeats)/Cas9 technology also allows for genome editing, and allows for site-specific genomic targeting in HBV.

The type II CRISPR/Cas system is a prokaryotic adaptive immune response system that uses non-coding RNAs to guide the Cas9 nuclease to induce site-specific DNA cleavage. This DNA damage is repaired by cellular DNA repair mechanisms, either via the non-homologous end joining DNA repair pathway (NHEJ) or the homology directed repair (HDR) pathway.

The CRISPR/Cas9 system provides a simple, RNA-programmable method to generate gene knockouts (via insertion/deletion) or knockins (via HDR), and allows for site-specific genomic targeting in HBV. The type II CRISPR/Cas system is a prokaryotic adaptive immune response system that uses non-coding RNAs to guide the Cas9 nuclease to induce site-specific DNA cleavage.

To create gene disruptions, a single guide RNA (sgRNA) is generated to direct the Cas9 nuclease to a specific genomic location. Cas9-induced double strand breaks are repaired via the NHEJ DNA repair pathway. The repair is error prone, and thus insertions and deletions (INDELs) may be introduced that can disrupt gene function.

Thus, targeting hepatitis B virus cccDNA using a CRISPR/Cas9 nuclease can efficiently inhibits viral replication.

Mir/MicroRNA

MicroRNAs (miRNAs) are tiny noncoding RNAs that regulate gene expression primarily at the post-transcriptional level by binding to mRNAs. miRNAs contribute to a variety of physiological and pathological processes. A number of miRNAs have been found to play a pivotal role in the host-HBV interaction. HBV infection can change the cellular miRNA expression patterns, and different stages of HBV associated disease have displayed distinctive miRNA profiles. The differential expressed miRNAs are involved in the progression of HBV-related diseases. For instance, some miRNAs are involved in liver tumorigenesis and tumor metastasis. Circulating miRNA in serum or plasma can be a very useful biomarker for the diagnosis and prognosis of HBV-related diseases. In addition, miRNA-based therapy can be used to treat, prevent, or cure HBV-related diseases. See, for example, Ying-Feng Wei, "MicroRNAs may solve the mystery of chronic hepatitis B virus infection," World J Gastroenterol. 2013 Aug. 14; 19(30): 4867-4876. http://www.ncbi.nlm.nih.gov/pmc/articles/PMC3740416/

In the interaction between virus and host, miRNAs can be divided into cellular miRNAs and viral miRNAs. Cellular miRNAs' expression profiles change at the infected state, and abnormal miRNAs often closely relate to the viral life cycle as well as the host disorder. Viral miRNAs can evolve to regulate both viral and cellular gene expression.

Sometimes, viruses exploit cellular miRNAs to facilitate certain steps of their life cycle. For example, miR-122 serves an antiviral role in the HBV life cycle. MiR-122 overexpression inhibits HBV expression, whereas depletion of endogenous miR-122 results in increased HBV production in transfected cells. MiR-122 inhibitors cause an increase in cellular heme oxygenase-1, which can decrease HBV covalently closed circular DNA (cccDNA) levels by reducing the stability of the HBV core protein. MiR-122 expression in the liver can be significantly down-regulated in patients with HBV infection compared with healthy controls. MiR-122 is significantly up-regulated in HBV-infected patients, and can inhibit HBV replication in Huh7 and HepG2 cells. Cyclin G1 is a miR-122 target that specifically interacts with p53, resulting in the specific binding of p53 to the HBV enhancer elements and simultaneous abrogation of the p53-mediated inhibition of HBV transcription.

HBV is a noncytopathic virus that replicates preferentially in the hepatocytes. cccDNA serves as a template for transcription of all viral RNA that is synthetized after HBV DNA enters the hepatocyte nucleus. The HBV genome is 3.2 kb in length and contains four overlapping open reading frames. It can transcribe viral pregenomic RNA that reverses transcription to synthesize the viral DNA genome and encode the hepatitis B virus surface antigen (HBsAg), hepatitis B virus core protein, viral reverse DNA polymerase (Pol) and X protein.

Hsa-miR-125a-5p interferes with HBV translation and down-regulates the expression of the HBV surface antigen. Accordingly, cellular miRNAs can alter HBV gene expression by targeting to HBV transcripts.

Cellular miRNAs can affect viral translation and change viral replication. In addition to the instance of the miR-122 inhibition of HBV replication, there are other examples where host miRNAs alter HBV replication. MiR-141 suppresses HBV replication by reducing HBV promoter activities, by down-regulating peroxisome proliferator-activated receptor alpha. DNA hypermethylation may be closely related to the suppression of HBV cccDNA transcription, and miR-152 may be a factor involved in the regulation of the methylation of HBV cccDNA.

Accordingly, miRNAs can directly or indirectly alter HBV replication. The close relationship between miRNAs and HBV-related diseases offers an opportunity to use miR-NAs or antagomir in combination therapies to treat, cure, or prevent HBV.

VIII. Pharmaceutical Compositions

Hosts, including but not limited to humans, infected with HBV can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound will be in the range of between about 0.01 and about 10 mg/kg, more generally, between about 0.1 and 5 mg/kg, and, preferably, between about 0.5 and about 2 mg/kg, of body weight of the recipient per day. The effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to one containing 7 to 600 mg, preferably 70 to 600 mg of active ingredient per unit dosage form. An oral dosage of 1-400 mg is usually convenient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

A preferred mode of administration of the active compound is oral, although for certain patients a sterile injectable form can be given sc, ip or iv. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antiviral compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

Transdermal Formulations

In some embodiments, the compositions are present in the form of transdermal formulations, such as that used in the FDA-approved agonist rotigitine transdermal (Neupro patch). Another suitable formulation is described in U.S. Publication No. 20080050424, entitled "Transdermal Therapeutic System for Treating Parkinsonism." This formulation includes a silicone or acrylate-based adhesive, and can include an additive having increased solubility for the active substance, in an amount effective to increase dissolving capacity of the matrix for the active substance.

The transdermal formulations can be single-phase matrices that include a backing layer, an active substance-containing self-adhesive matrix, and a protective film to be removed prior to use. More complicated embodiments contain multiple-layer matrices that may also contain non-adhesive layers and control membranes. If a polyacrylate adhesive is used, it can be crosslinked with multivalent metal ions such as zinc, calcium, aluminum, or titanium ions, such as aluminum acetylacetonate and titanium acetylacetonate.

When silicone adhesives are used, they are typically polydimethylsiloxanes. However, other organic residues such as, for example, ethyl groups or phenyl groups may in principle be present instead of the methyl groups. Because the active compounds are amines, it may be advantageous to use amine-resistant adhesives. Representative amine-resistant adhesives are described, for example, in EP 0 180 377.

Representative acrylate-based polymer adhesives include acrylic acid, acrylamide, hexylacrylate, 2-ethylhexylacrylate, hydroxyethylacrylate, octylacrylate, butylacrylate, methylacrylate, glycidylacrylate, methacrylic acid, methacrylamide, hexylmethacrylate, 2-ethylhexylmethacrylate, octylmethacrylate, methylmethacrylate, glycidylmethacrylate, vinylacetate, vinylpyrrolidone, and combinations thereof.

The adhesive must have a suitable dissolving capacity for the active substance, and the active substance most be able to move within the matrix, and be able to cross through the contact surface to the skin. Those of skill in the art can readily formulate a transdermal formulation with appropriate transdermal transport of the active substance.

Certain pharmaceutically acceptable salts tend to be more preferred for use in transdermal formulations, because they can help the active substance pass the barrier of the stratum corneum. Examples include fatty acid salts, such as stearic acid and oleic acid salts. Oleate and stearate salts are relatively lipophilic, and can even act as a permeation enhancer in the skin.

Permeation enhancers can also be used. Representative permeation enhancers include fatty alcohols, fatty acids, fatty acid esters, fatty acid amides, glycerol or its fatty acid esters, N-methylpyrrolidone, terpenes such as limonene, alpha-pinene, alpha-terpineol, carvone, carveol, limonene oxide, pinene oxide, and 1,8-eucalyptol.

The patches can generally be prepared by dissolving or suspending the active agent in ethanol or in another suitable organic solvent, then adding the adhesive solution with stirring. Additional auxiliary substances can be added either to the adhesive solution, the active substance solution or to the active substance-containing adhesive solution. The solution can then be coated onto a suitable sheet, the solvents removed, a backing layer laminated onto the matrix layer, and patches punched out of the total laminate.

Nanoparticulate Compositions

The compounds described herein can also be administered in the form of nanoparticulate compositions.

In one embodiment, the controlled release nanoparticulate formulations comprise a nanoparticulate active agent to be administered and a rate-controlling polymer which functions to prolong the release of the agent following administration. In this embodiment, the compositions can release the active agent, following administration, for a time period ranging from about 2 to about 24 hours or up to 30 days or longer. Representative controlled release formulations including a nanoparticulate form of the active agent are described, for example, in U.S. Pat. No. 8,293,277.

Nanoparticulate compositions comprise particles of the active agents described herein, having a non-crosslinked surface stabilizer adsorbed onto, or associated with, their surface.

The average particle size of the nanoparticulates is typically less than about 800 nm, more typically less than about 600 nm, still more typically less than about 400 nm, less than about 300 nm, less than about 250 nm, less than about 100 nm, or less than about 50 nm. In one aspect of this embodiment, at least 50% of the particles of active agent have an average particle size of less than about 800, 600, 400, 300, 250, 100, or 50 nm, respectively, when measured by light scattering techniques.

A variety of surface stabilizers are typically used with nanoparticulate compositions to prevent the particles from clumping or aggregating. Representative surface stabilizers include, but are not limited to, gelatin, lecithin, dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol, polyvinylpyrrolidone, tyloxapol, poloxamers, poloxamines, poloxamine 908, dialkylesters of sodium sulfosuccinic acid, sodium lauryl sulfate, an alkyl aryl polyether sulfonate, a mixture of sucrose stearate and sucrose distearate, p-isononylphenoxypoly-(glycidol), SA9OHCO, decanoyl-N-methylglucamide, n-decyl-D-glucopyranoside, n-decyl-D-maltopyranoside, n-dodecyl-D-glucopyranoside, n-dodecyl-D-maltoside, heptanoyl-N-methylglucamide, n-heptyl-D-glucopyranoside, n-heptyl-D-thioglucoside, n-hexyl-D-glucopyranoside, nonanoyl-N-methylglucamide, n-nonyl-D-glucopyranoside, octanoyl-N-methylglucamide, n-octyl-D-glucopyranoside, and octyl-D-thioglucopyranoside. Lysozymes can also be used as surface stabilizers for nanoparticulate compositions. Certain nanoparticles such as poly(lactic-co-glycolic acid) (PLGA)-nanoparticles are known to target the liver when given by intravenous (IV) or subcutaneously (SQ).

Because HBV causes damage to, and are present in the liver, in one embodiment, the nanoparticles or other drug delivery vehicles are targeted to the liver. One such type of liver-targeted drug delivery vehicle is described in Park, et al., Mol Imaging February 2011; 10(1): 69-77, and uses Glypican-3 (GPC3) as a molecular target. Park taught using this target for hepatocellular carcinoma (HCC), a primary liver cancer frequently caused by chronic persistent hepatitis.

In one aspect of this embodiment, this drug delivery vehicle is also used to target therapeutics to the liver to treat viral infections. Further, since the compounds described herein have indirect anti-cancer uses, this type of system can target the compounds to the liver and treat liver cancers or reverse the cancer. GPC3 is a heparan sulfate proteoglycan that is not expressed in normal adult tissues, but significantly over-expressed in up to 80% of human HCC's. GPC3 can be targeted, for example, using antibody-mediated targeting and binding (See Hsu, et al., Cancer Res. 1997; 57:5179-84).

Another type of drug delivery system for targeting the liver is described in U.S. Pat. No. 7,304,045. The '045 patent discloses a dual-particle tumor or cancer targeting system that includes a first ligand-mediated targeting nanoparticle conjugated with galactosamine, with the ligand being on a target cell. The first nanoparticle includes poly(γ-glutamic acid)/poly(lactide) block copolymers and n antiviral compound, which in this case is a compound described herein, and in the '045 patent, was ganciclovir. A second nanoparticle includes poly(γ-glutamic acid)/poly(lactide) block copolymers, an endothelial cell-specific promoter, and a (herpes-simplex-virus)-(thymidine kinase) gene constructed plasmid, and provides enhanced permeability and retention-mediated targeting. The first and said second nanoparticles are mixed in a solution configured for delivering to the liver. When the disorder to be treated is a liver tumor or cancer, the delivery can be directly to, or adjacent to, the liver tumor or cancer.

Representative rate controlling polymers into which the nanoparticles can be formulated include chitosan, polyethylene oxide (PEO), polyvinyl acetate phthalate, gum arabic, agar, guar gum, cereal gums, dextran, casein, gelatin, pectin, carrageenan, waxes, shellac, hydrogenated vegetable oils, polyvinylpyrrolidone, hydroxypropyl cellulose (HPC), hydroxyethyl cellulose (HEC), hydroxypropyl methylcellulose (HPMC), sodium carboxymethylcellulose (CMC), poly (ethylene) oxide, alkyl cellulose, ethyl cellulose, methyl cellulose, carboxymethyl cellulose, hydrophilic cellulose derivatives, polyethylene glycol, polyvinylpyrrolidone, cellulose acetate, cellulose acetate butyrate, cellulose acetate phthalate, cellulose acetate trimellitate, polyvinyl acetate phthalate, hydroxypropylmethyl cellulose phthalate, hydroxypropylmethyl cellulose acetate succinate, polyvinyl acetaldiethylamino acetate, poly(alkylmethacrylate), poly (vinyl acetate), polymers derived from acrylic or methacrylic acid and their respective esters, and copolymers derived from acrylic or methacrylic acid and their respective esters.

Methods of making nanoparticulate compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Iododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly (ethylene Oxide) Polymers;" U.S. Pat. No. 5,585,108 for "Formulations of Oral Gastrointestinal Therapeutic Agents in Combination with Pharmaceutically Acceptable Clays;" U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive nanoparticulate compositions having cationic surface stabilizers;" U.S. Pat. No. 6,431,478 for "Small Scale Mill;" and U.S. Pat. No. 6,432,381 for "Methods for targeting drug delivery to the upper and/or lower gastrointestinal tract," all of which are specifically incorporated by reference. In addition, U.S. Patent Application No. 20020012675 A1, published on Jan. 31, 2002, for "Controlled Release Nanoparticulate Compositions," describes nanoparticulate compositions, and is specifically incorporated by reference.

The nanoparticle formulations including the compounds described herein, and also in the form of a prodrug or a salt, can be used to treat or prevent infections by hepatitis B virus.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

Controlled Release Formulations

In a preferred embodiment, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

The terms used in describing the invention are commonly used and known to those skilled in the art. As used herein, the following abbreviations have the indicated meanings:
ACN Acetonitrile
$Boc_2O$ Di-tert-butyl dicarbonate
CDI carbonyldiimidazole
DCC N,N'-dicyclohexylcarbodiimide
DCM dichloromethane
DIPEA diisopropyl ethyl amine (Hünig's base)
DMAP 4-Dimethylaminopyridine
DMF N,N-dimethylformamide
DMSO dimethylsulfoxide
EDC 1-ethyl-3-(3-dimethylaminopropyl)carbodiimide hydrochloride
EtOAc ethyl acetate
h hour
HATU 1-[Bis(dimethylamino)methylene]-1H-1,2,3-triazolo[4,5-b]pyridinium-3-oxide hexafluorophosphate
M molar
min minute
rt or RT room temperature
TFA trifluoroacetic acid
THF tetrahydrofuran
DMA Dimethylacetamide IX. General Methods for Preparing Active Compounds Methods for the facile preparation of active compounds are known in the art and result from the selective combination of known methods. The compounds disclosed herein can be prepared as described in detail below, or by other methods known to those skilled in the art. It will be understood by one of ordinary skill in the art that variations of detail can be made without departing from the spirit and in no way limiting the scope of the present invention.

The various reaction schemes are summarized below.
Scheme 1 is a non-limiting example of the synthesis of active compounds of the present invention, and in particular, a synthetic approach to compound A.
Scheme 2 is a non-limiting example of the synthesis of active compounds of the present invention, and in particular, an alternate synthetic approach to compound B.

Scheme 3 is a non-limiting example of the synthesis of active compounds of the present invention, and in particular, a synthetic approach to compound C.

Scheme 4 is a non-limiting example of the synthesis of active compounds of the present invention, and in particular, a synthetic approach to compound D.

Scheme 5 is a non-limiting example of the synthesis of active compounds of the present invention, and in particular, a synthetic approach to compound E.

Scheme 6 is a non-limiting example of the synthesis of active compounds of the present invention, and in particular, a synthetic approach to compound F and G.

Scheme 7 is a non-limiting example of the synthesis of active compounds of the present invention, and in particular, a synthetic approach to compound H.

Compounds of formula A can be prepared by first selective reaction of an aniline derivative with a carboxylic acid chloride of general formula I in the presence of an organic base such as $Et_3N$ or DIPEA. Intermediate III is then reacted with an amine of general formula IV, for example in an organic solvent like $CH_2Cl_2$, in the presence of an organic base such as $Et_3N$.

Scheme 1 A synthetic approach to compound A

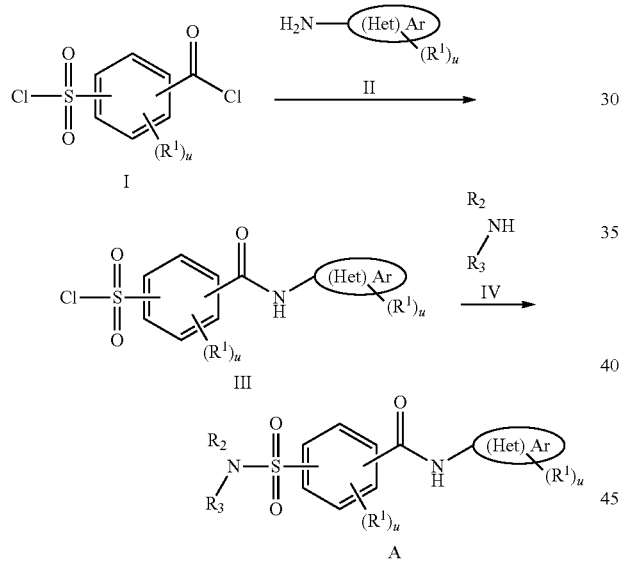

Compounds of formula B can be prepared by first selective reaction of an amine derivative with a carboxylic acid chloride of general formula V in the presence of an organic base such as $Et_3N$ or DIPEA. Intermediate VI is then reacted with an amine of general formula IV, for example in an organic solvent like $CH_2Cl_2$, in the presence of an organic base such as $Et_3N$.

Scheme 2 A synthetic approach to compound B

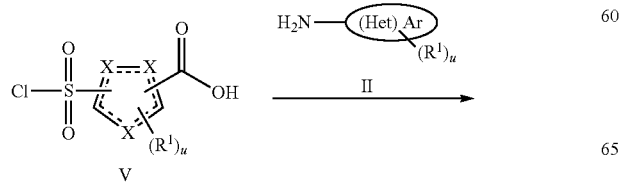

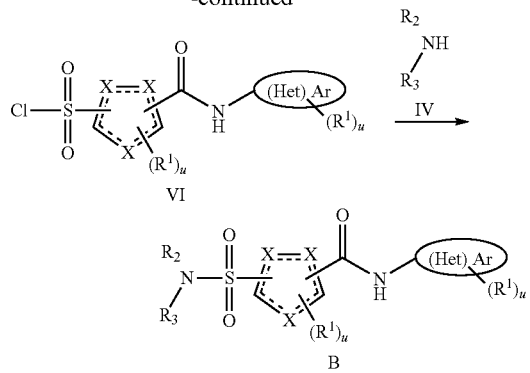

The synthesis of compounds of general formula C can be performed as outlined in Scheme 3. A carboxylic acid of general formula VII can be N-protected, for example, by treatment with $Boc_2O$ in the presence of a base such as $NaHCO_3$. Intermediate VIII can be coupled with an amine of general formula II using a peptide coupling reagent like, for example, EDC in the presence of an organic amine base such as DMAP. The resulting compound of general formula IX can then be deprotected, for example, in the presence of TFA when Boc was used as a protecting group and then reacted with a sulfonyl chloride of general formula X in the presence of an organic amine base such as $Et_3N$.

Scheme 3 A synthetic approach to compound C

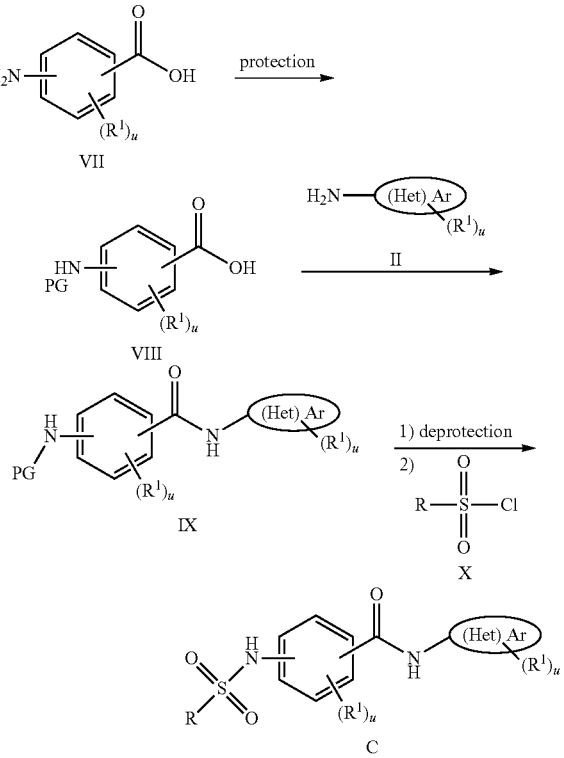

The synthesis of compounds of general formula D can be performed as outlined in Scheme 4. An ester of general formula XI can be reacted with an oxalyl chloride monoalkylester of general formula XII in the presence of a Lewis acid like, for example, $AlCl_3$ to give intermediate XIII.

Selective hydrolysis with an inorganic base like, for example, NaOH followed by the coupling of the resulting alpha keto acid XIV with an amine of general formula IV in the presence of a peptide coupling reagent like, for example, CDI provides compounds of general formula XV. Hydrolysis of the ester moiety with an inorganic base like, for example, NaOH followed by the coupling of the resulting carboxyl acid with an amine of general formula II in the presence of a peptide coupling reagent like, for example, HATU in the presence of an organic amine base such as DIPEA gives compounds of general formula D.

such as DIPEA. Intermediate XVIII can be reacted with an oxalyl chloride monoalkylester of general formula XII in the presence of a Lewis acid like, for example, AlCl₃ to give intermediate XIX. Selective hydrolysis with an inorganic base like, for example, NaOH followed by the coupling of the resulting alpha keto acid XX with an alcohol of general formula XXI in the presence of a peptide coupling reagent like, for example, DCC in the presence of an organic amine base such as DMAP provides compounds of general formula E.

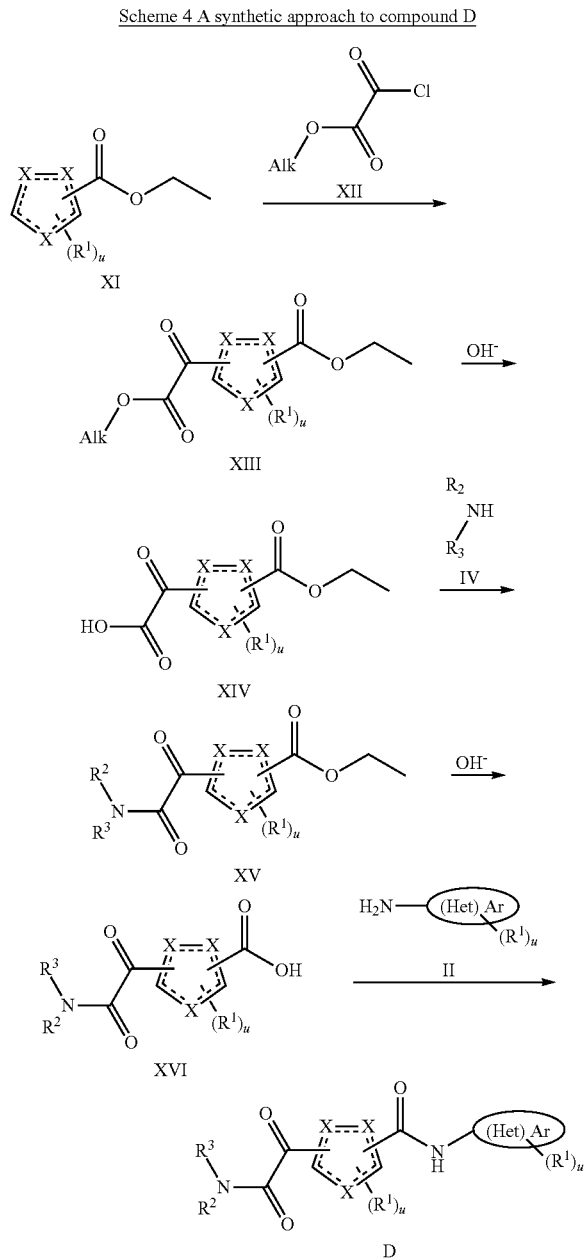

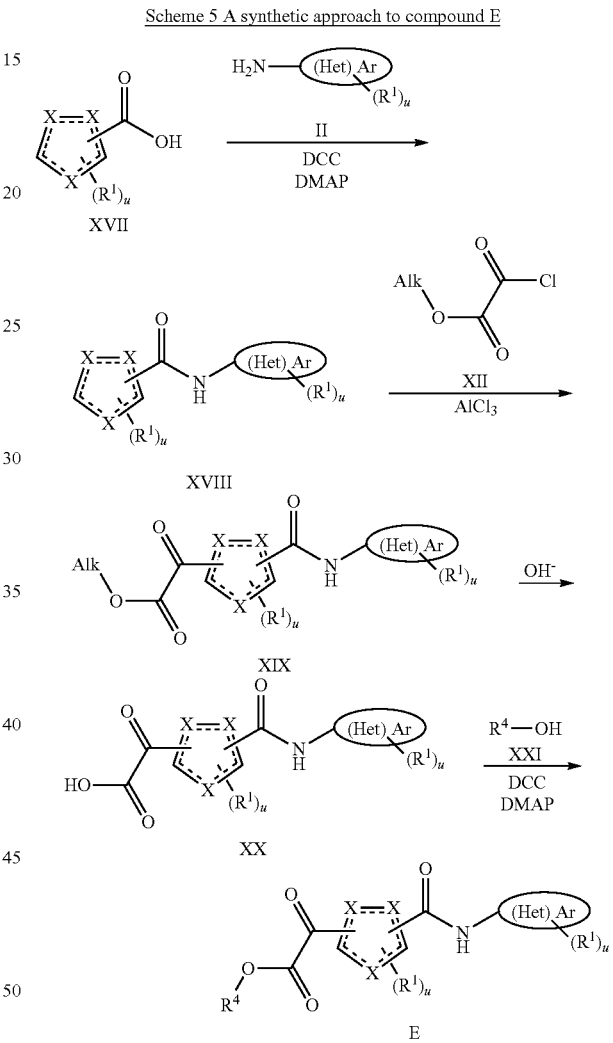

The synthesis of compounds of general formula E can be performed as outlined in Scheme 5. A carboxylic acid of general formula XVII can be coupled with an amine of general formula II using a peptide coupling reagent like, for example, HATU in the presence of an organic amine base The synthesis of compounds of general formula F and G can be performed as outlined in Scheme 6. A carboxylic acid of general formula XXII can be coupled with an amine of general formula II using a peptide coupling reagent like, for example, HATU in the presence of an organic amine base such as DIPEA. Reduction of compounds XXIII using, for example, Zn in the presence of formic acid leads to amino derivatives of general formula XXIV which can be either reacted with an oxoacetic acid derivative of general formula XXV in the presence of a peptide coupling reagent like, for example, DCC or with a sulfonyl chloride of general formula X in the presence of an organic amine base such as Et₃N to afford respectively compounds of general Formulas F and G.

Scheme 6 A synthetic approach to compounds F and G

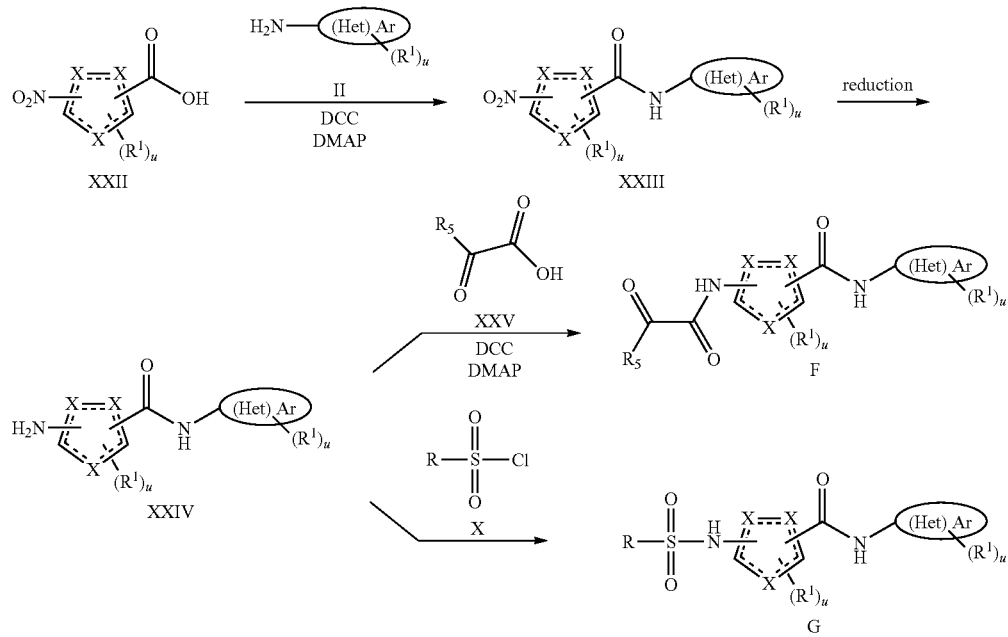

The synthesis of compounds of general formula H can be performed as outlined in Scheme 7. A bromo derivative of general formula XXVI can undergo a lithium-halogen exchange using an organolithium reagent such as, for example, n-BuLi and react with a dialkyloxalate like, for example, diethyl oxalate. The resulting compound can then be hydrolyzed to form the carboxylic acid of general formula XXVIII which can be coupled with an amine of general formula II using a peptide coupling reagent like, for example, HATU in the presence of an organic amine base such as DIPEA. Hydrolysis of compound XXIX with an inorganic base like, for example, NaOH followed by the coupling of the resulting alpha keto acid XXX with an amine of general formula IV in the presence of a peptide coupling reagent like, for example, CDI in the presence of an organic amine base such as DIPEA provides compounds of general formula H.

Scheme 7 A synthetic approach to compounds H

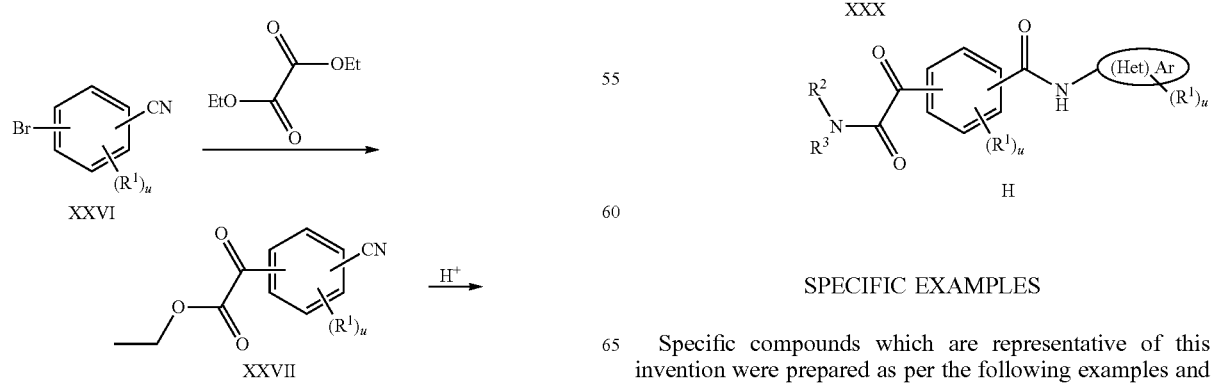

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The present compounds can also be used as intermediates in subsequent examples to produce additional compounds of the present invention. No attempt has necessarily been made to optimize the yields obtained in any of the reactions. One skilled in the art would know how to increase such yields through routine variations in reaction times, temperatures, solvents and/or reagents.

Anhydrous solvents were purchased from Aldrich Chemical Company, Inc. (Milwaukee, Wis.) and EMD Chemicals Inc. (Gibbstown, N.J.). Reagents were purchased from commercial sources. Unless noted otherwise, the materials used in the examples were obtained from readily available commercial suppliers or synthesized by standard methods known to one skilled in the art of chemical synthesis. $^1$H and $^{13}$C NMR spectra were taken on a Bruker Ascend™ 400 MHz Fourier transform spectrometer at room temperature and reported in ppm downfield from internal tetramethylsilane. Deuterium exchange, decoupling experiments or 2D-COSY were performed to confirm proton assignments. Signal multiplicities are represented by s (singlet), d (doublet), dd (doublet of doublets), t (triplet), q (quadruplet), br (broad), bs (broad singlet), m (multiplet). All J-values are in Hz. Mass spectra were determined on a Micromass Platform LC spectrometer using electrospray techniques. Analytic TLC were performed on Sigma-Aldrich® aluminum supported silica gel (25 μm) plates. Column chromatography was carried out on Silica Gel or via reverse-phase high performance liquid chromatography.

Example 1

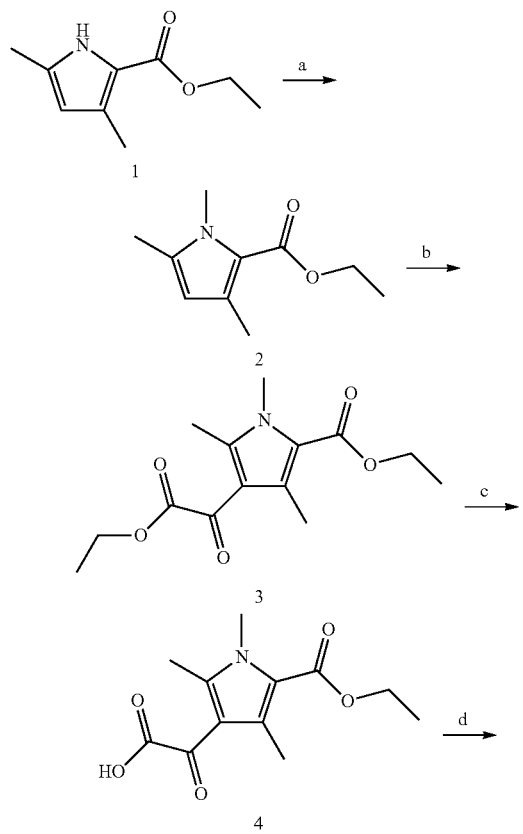

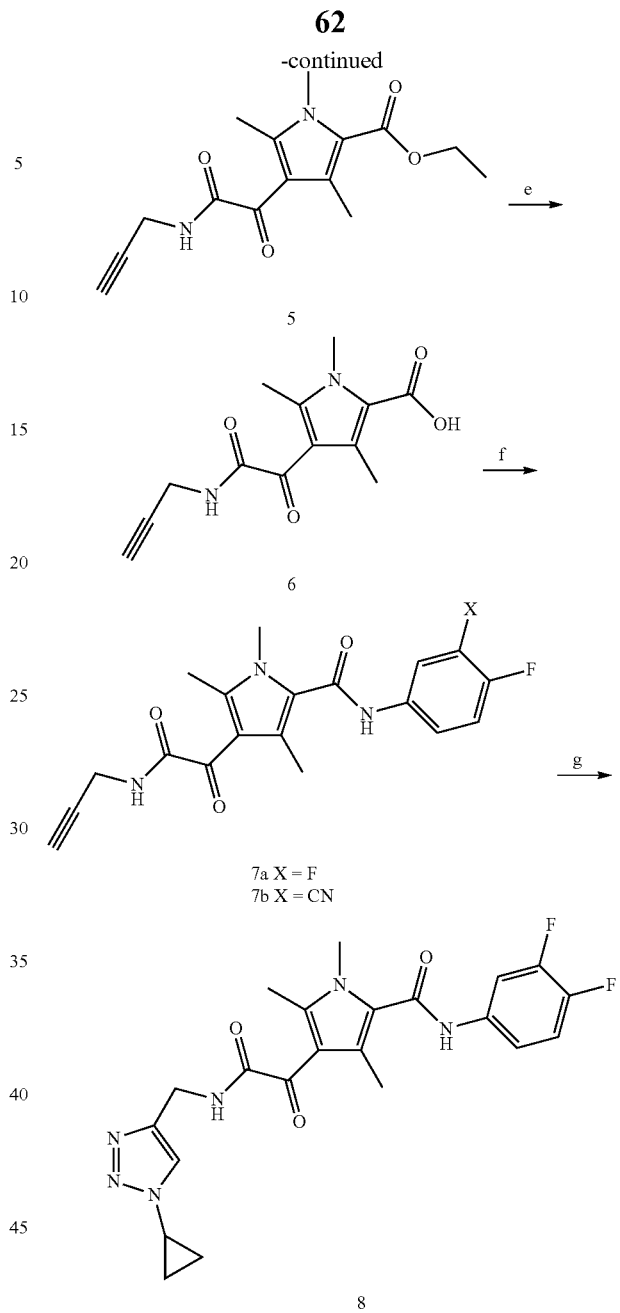

Reagents and conditions: a) MeI, KOH, DMSO; b) ClCOCOOEt, AlCl$_3$, CH$_2$Cl$_2$; c) NaOH 5%, MeOH, RT, 10 min; d) CDI, HCCCH$_2$NH$_2$, DMF, 3 h, RT; e) NaOH 5%, MeOH, 16 h, RT; f) 3,4-difluoroaniline, HATU, DIPEA, DMF, 16 h, RT; or SOCl$_2$, 3-cyano-4-fluoroaniline, DMA, reflux; g) i) bromocyclopropane, NaN$_3$, H$_2$O, 120° C., MW, 30 min; ii) CuSO$_4$, Na ascorbate, ACN, 80° C., MW, 30 min.

Ethyl 1,3,5-Trimethylpyrrole-2-carboxylate (2)

Ethyl 3,5-dimethylpyrrole-2-carboxylate (100.0 g, 0.59 mol) was added to a solution of potassium hydroxide (100.6 g, 1.79 mol) in dimethyl sulfoxide (1 L) and stirred for 30 min under nitrogen at 0° C. Methyl iodide (55.9 mL, 0.89 mol) was then added and the reaction mixture was allowed to warm up to room temperature and stirred for 4 hours. The reaction was then extracted with diethyl ether (3×1 L) and the combined organic layer were finally washed with water (2×150 mL), dried over Na$_2$SO$_4$ and concentrated in vacuo. The residue slowly crystallized to yield ethyl 1,3,5-trimethylpyrrole-2-carboxylate 2 (102.4 g, 0.56 mol, 94%) as a yellowish solid. $^1$H NMR (400 MHz, CDCl$_3$) δ: 1.32 (t, 3H), 2.20 (s, 3H), 2.30 (s, 3H), 3.75 (s, 3H), 4.22 (q, 2H), 5.75 (s, 1H). MS (ESI): m/z [M+H]$^+$ calcd for C$_9$H$_{14}$NO$_2$: 182.2, found: 182.3.

1,3,5-trimethyl-4-(2-oxo-2-(prop-2-yn-1-ylamino) acetyl)-1H-pyrrole-2-carboxylic acid (6)

To a solution of ethyl 1,3,5-trimethylpyrrole-2-carboxylate (10.0 g, 55.2 mmol) in CH$_2$Cl$_2$ (250 mL) at 0° C. was added dropwise a solution of ethyl 2-chloro-2-oxo-acetate (9.3 mL, 82.8 mmol) in CH$_2$Cl$_2$ (100 mL) followed by AlCl$_3$ (22.1 g, 165.7 mmol) portion wise. The reaction mixture was then stirred overnight at room temperature and then quenched with ice. After addition of water (300 mL), the mixture was filtered on celite and extracted with CH$_2$Cl$_2$ (3×100 mL). The combined organic layers were washed with a saturated solution of sodium carbonate (250 mL) and a saturated solution of ammonium chloride (250 mL), dried over Na$_2$SO$_4$ and concentrated in vacuo. To the resulting oil were added methanol (100 mL) and a 5% solution of sodium hydroxide (100 mL) and the mixture was stirred for 15 min at room temperature. After removal of the methanol under vacuum, the mixture was washed with ethyl acetate (2×100 mL), acidified with a 1N HCl solution (pH=1) and extracted with ethyl acetate (3×100 mL). The combined organic layers were dried over sodium sulfate and concentrated under vacuum. The resulting solid was washed with diethyl ether (100 mL) and hexanes (100 mL) to yield 2-(5-ethoxycarbonyl-1,3,5-trimethyl-pyrrol-3-yl)-2-oxo-acetic acid 4 (8.1 g, 32.0 mmol, 58%) as an off-white powder. To a solution of 2-(5-ethoxycarbonyl-1,3,5-trimethyl-pyrrol-3-yl)-2-oxo-acetic acid 4 (2.0 g, 7.9 mmol) in DMF (15 mL) and CH$_2$Cl$_2$ (10 mL) was added 1,1'-carbonyldiimidazole (1.92 g, 11.8 mmol) and propargylamine (0.607 mL, 9.5 mmol). After stirring for 2 h at room temperature, the reaction mixture was poured into a saturated solution of ammonium chloride and extracted with CH$_2$Cl$_2$ (3×100 mL).

The combined organic layers were dried over sodium sulfate and concentrated in vacuo to give 5 as a yellowish oil. To the crude ethyl 4-[2-(propargylamino)-2-oxo-acetyl]-1,3,5-trimethyl-pyrrole-2-carboxylate 5 dissolved in methanol (10 mL) and THF (10 mL) was added a 5% solution of sodium hydroxide (10 mL). The reaction mixture was stirred at room temperature overnight and after evaporation of the methanol and THF in vacuo, the aqueous solution was washed with ethyl acetate (2×50 mL), acidified with a 1N HCl solution (pH=1) and extracted with ethyl acetate (3×50 mL). The combined organic layers were dried over sodium sulfate and concentrated in vacuo. The resulting solid was washed with diethyl ether (50 mL) and hexanes (50 mL) to yield 4-[2-(propargylamino)-2-oxo-acetyl]-1,3,5-trimethyl-pyrrol-2-carboxylic acid 6 (1.8 g, 6.9 mmol, 87%) as a white powder. $^1$H NMR (400 MHz, DMSO-d6) δ 12.77 (s, 1H), 9.14 (t, J=5.7 Hz, 1H), 3.99 (dd, J=5.7, 2.6 Hz, 2H), 3.75 (s, 3H), 3.18 (t, J=2.4 Hz, 1H), 2.37 (s, 6H). $^{13}$C NMR (101 MHz, DMSO) δ 188.0, 167.2, 163.0, 142.8, 129.7, 121.8, 117.5, 80.5, 73.8, 33.3, 28.1, 12.3, 12.0. HRMS (ESI): m/z [M+H]$^+$ calcd for C$_{13}$H$_{15}$N$_2$O$_4$: 263.1032, found: 263.1025.

4-[(Propargylamino)(oxo)acetyl]-N-(3,4-difluorophenyl)-1,3,5-trimethyl-1H-pyrrole-2-carboxamide (7a)

To a solution of 4-[2-(propargylamino)-2-oxo-acetyl]-1,3,5-trimethyl-pyrrol-2-carboxylic acid 6 (750 mg, 2.7 mmol), 3,4-difluoroaniline (410 mg, 3.2 mmol) and DIPEA (746 µL, 4.3 mmol) in DMF (15 mL) was added HATU (1.63 g, 4.3 mmol) at room temperature. The mixture was stirred at 50° C. for 3 h. In order to reach completion, more 3,4-difluoroaniline (410 mg, 3.2 mmol) was added and the mixture was further stirred overnight at 65° C. The reaction mixture was then poured into a saturated solution of ammonium chloride and extracted with ethyl acetate (3×50 mL).

The combined organic layers were dried over sodium sulfate and concentrated in vacuo. The residue was purified by flash chromatography (Hexanes:EtOAc=6:4 v/v) to give compound 7a as a white powder (47%, 503 mg, 1.4 mmol). $^1$H NMR (400 MHz, Acetone-d$_6$) δ 9.49 (s, 1H), 8.22-8.07 (m, 1H), 8.07-7.95 (m, 1H), 7.59-7.43 (m, 1H), 7.33 (q, J=9.4 Hz, 1H), 4.21-4.07 (m, 2H), 3.69 (s, 3H), 2.73 (s, 1H), 2.43 (s, 3H), 2.29 (s, 3H). $^{13}$C NMR (101 MHz, Acetone) δ 188.9, 167.9, 162.1, 152.7, 152.6, 150.3, 150.2, 149.3, 149.2, 146.9, 146.8, 142.8, 137.9, 137.9, 128.5, 124.6, 119.1, 118.9, 118.8, 117.5, 117.5, 117.4, 117.4, 110.7, 110.5, 81.4, 73.2, 33.2, 29.7, 12.8, 12.7. $^{19}$F NMR (377 MHz, Acetone-d6) δ −139.8--140.0 (m), −147.1--147.2 (m). HRMS (ESI): m/z [M+H]$^+$ calcd for C$_{19}$H$_{18}$F$_2$N$_3$O$_3$: 374.1316, found: 374.1309.

4-(2-(((1-cyclopropyl-1H-1,2,3-triazol-4-yl)methyl) amino)-2-oxoacetyl)-N-(3,4-difluorophenyl)-1,3,5-trimethyl-1H-pyrrole-2-carboxamide (8)

A solution of bromocyclopropane (0.4 mL, 3.3 mmol) and sodium azide (430 mg, 6.6 mmol) in water (1 mL) was heated under microwave irradiation for 30 minutes at 120° C. A solution of compound 7 (0.05 g, 0.1 mmol) in acetonitrile (1 mL) was then added, followed by sodium ascorbate (10 mg, 0.05 mmol) and copper sulfate (20 mg, 0.12 mmol). The mixture was heated for 30 minutes at 80° C. under microwave irradiation and then poured into a saturated solution of ammonium chloride (50 mL). After extraction with ethyl acetate (3×50 mL), the combined organic layers were dried over sodium sulfate and concentrated in vacuo. The resulting mixture was purified by flash chromatography (Hexanes/Ethyl acetate=6:4 v/v), to give compound 8 as a white powder (61%, 31 mg, 0.06 mmol). $^1$H NMR (400 MHz, Acetone-d$_6$) δ 9.50 (s, 1H), 8.29-8.18 (m, 1H), 8.06-7.94 (m, 1H), 7.87 (s, 1H), 7.57-7.48 (m, 1H), 7.39-7.28 (m, 1H), 6.16-5.98 (m, 1H), 5.31-5.20 (m, 1H), 5.09-5.00 (m, 2H), 4.58 (d, J=5.9 Hz, 2H), 3.67 (d, J=1.4 Hz, 3H), 2.38 (d, J=1.3 Hz, 3H), 2.24 (d, J=1.3 Hz, 3H). $^{13}$C NMR (101 MHz, Acetone) δ 187.4, 166.3, 160.3, 150.9, 150.8, 148.5, 148.4, 147.5, 147.4, 145.1, 144.9, 144.4, 144.4, 140.9, 136.2, 136.1, 136.1, 136.0, 132.7, 126.6, 122.9, 122.5, 118.3, 117.3, 117.1, 117.1, 115.7, 115.7, 115.7, 115.7, 108.9, 108.7, 51.9, 34.4, 31.4, 11.1, 11.0. $^{19}$F NMR (377 MHz, Acetone-d6) δ −139.8--140.1 (m), −147.0--147.2 (m). HRMS (ESI): m/z [M+H]$^+$ calcd for C$_{22}$H$_{23}$F$_2$N$_6$O$_3$: 457.1800, found: 457.1790.

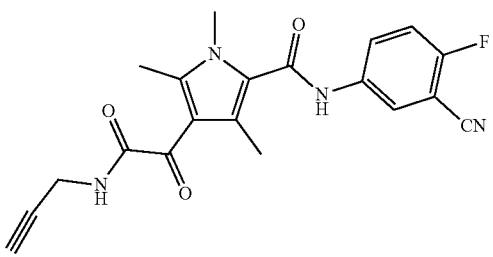 [SMILES: C#CCNC(=O)C(=O)c1c(C)c(C(=O)Nc2ccc(F)c(C#N)c2)n(C)c1C]

N-(3-cyano-4-fluorophenyl)-1,3,5-trimethyl-4-(2-oxo-2-(prop-2-yn-1-ylamino)acetyl)-1H-pyrrole-2-carboxamide (7b)

To a solution of 4-[2-(propargylamino)-2-oxo-acetyl]-1,3,5-trimethyl-pyrrol-2-carboxylic acid 6 (0.1 g, 0.38 mmol) in toluene (5 mL) was added 0.1 mL of SOCl$_2$ at room temperature and the mixture was refluxed for 1.5 h. After removal of SOCl$_2$ in vacuo, the residual oil was solubilized in DMA (5 mL) and 3-cyano-4-fluoroaniline (0.1 g, 0.7 mmol) was added. The mixture was stirred at 100° C. for 3 h and then cooled down to room temperature. The solution was then poured into a saturated solution of ammonium chloride (50 mL) and extracted with EtOAc (3×25 mL). The combined organic layers were dried over sodium sulfate and concentrated in vacuo.

The resulting residue was purified by flash chromatography (Hexanes/EtOAc=6:4 v/v) to yield N-(3-cyano-4-fluorophenyl)-1,3,5-trimethyl-4-(2-oxo-2-(prop-2-yn-1-ylamino)acetyl)-1H-pyrrole-2-carboxamide 7b (48%, 0.7 g, 0.2 mmol). $^1$H NMR (400 MHz, Acetone-d$_6$) δ 9.61 (s, 1H), 8.37-8.27 (m, 1H), 8.15 (s, 1H), 8.13-8.04 (m, 1H), 7.45 (t, J=9.1 Hz, 1H), 4.21-4.06 (m, 2H), 3.70 (s, 3H), 2.77-2.70 (m, 1H), 2.43 (s, 3H), 2.30 (s, 3H). $^{13}$C NMR (101 MHz, Acetone-d$_6$) δ 188.9, 167.8, 162.3, 160.7 (d, J=252.7 Hz) 143.0, 138.0 (d, J=3.1 Hz), 128.4 (d, J=8.1 Hz), 128.2, 125.5, 125.0, 118.9, 118.6 (d, J=20.9 Hz), 115.3, 102.6 (d, J=16.5 Hz), 81.4, 73.3, 33.3, 29.7, 12.9, 12.8. $^{19}$F NMR (377 MHz, Acetone-d$_6$) δ −115.9 (dd, J=9.6, 4.7 Hz). LCMS (ESI): m/z [M+H]$^+$ calcd for C$_{20}$H$_{19}$FN$_4$O$_3$: 381.1, found: 381.3.

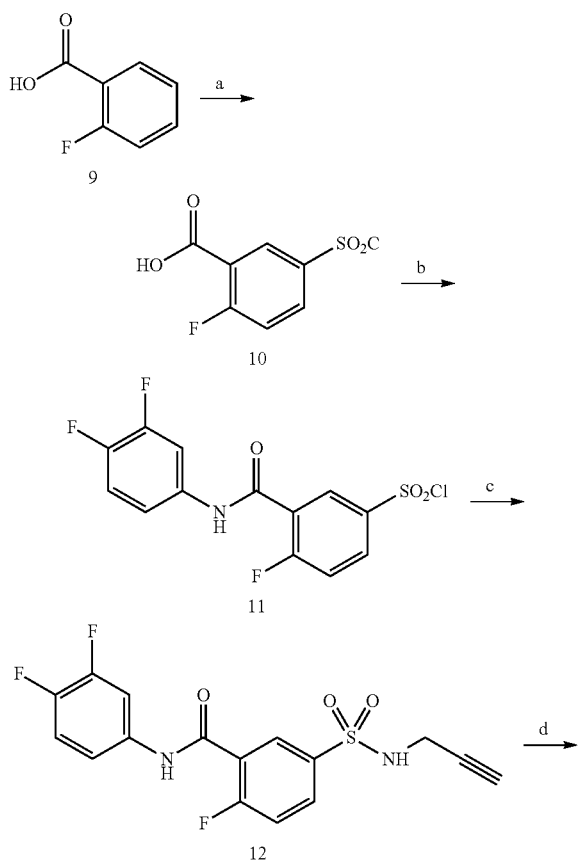

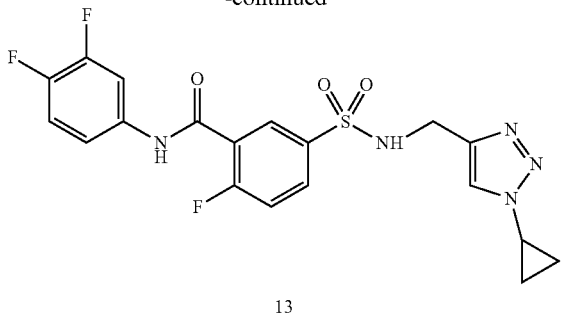

13

Reagents and conditions: a) HSO$_3$Cl, 0° C., 1 h; b) i) SOCl$_2$, 80° C., 1.5 h; ii) 3,4-difluoroaniline toluene, 100° C., 4 h; c) Propargylamine, Et$_3$N, DMF, RT, overnight; d) i) bromocyclopropane, NaN$_3$, H$_2$O, 120° C., MW, 30 min; ii) CuSO$_4$, sodium ascorbate, CH$_3$CN, 80° C., MW, 30 min.

5-(N-((1-Cyclopropyl-1H-1,2,3-triazol-4-yl)methyl)sulfamoyl)-N-(3,4-difluorophenyl)-2-fluorobenzamide (13)

2-fluorobenzoic acid 9 (10.0 g, 71.4 mmol) was added to chlorosulfonic acid (50 mL) at 0° C. and the mixture was stirred at 0° C. for 1 h. The reaction mixture was then slowly poured onto ice. The precipitate formed was filtered, rinsed off with water (3×100 mL) and dried under vacuum overnight to yield 5-(chlorosulfonyl)-2-fluorobenzoic acid 10 as a brownish solid (10.5 g, 44.0 mmol). 5-(chlorosulfonyl)-2-fluorobenzoic acid 10 (10.0 g, 41.9 mmol) was added to 60 mL of SOCl$_2$ at room temperature and the mixture was refluxed for 1.5 h. After removal of SOCl$_2$ in vacuo, the residual oil was solubilized in toluene (150 mL) and 3,4-difluoroaniline (6.5 g, 50.3 mmol) was added. The mixture was stirred at 100° C. for 4 h and then cooled down to room temperature. The solution was then poured into a saturated solution of ammonium chloride (200 mL) and extracted with EtOAc (3×200 mL). The combined organic layers were dried over sodium sulfate and concentrated in vacuo. The resulting residue was purified by flash chromatography (Hexanes/EtOAc=6:4 v/v) to yield 3-((3,4-difluorophenyl)carbamoyl)-4-fluorobenzene-1-sulfonylchloride 11 (92%, 13.51 g, 38.6 mmol). To a solution of 3-((3,4-difluorophenyl)carbamoyl)-4-fluorobenzene-1-sulfonyl chloride 11 (10.0 g, 28.6 mmol) in CH$_2$Cl$_2$ (200 mL) at 0° C. were added propargylamine hydrochloride (3.1 g, 34.3 mmol) and Et$_3$N (7.8 mL, 57.2 mmol). The reaction mixture was stirred overnight at room temperature and then poured into a saturated solution of ammonium chloride (250 mL). After extraction with CH$_2$Cl$_2$ (3×100 mL), the combined organic layers were dried over sodium sulfate and finally concentrated in vacuo. The resulting solid was washed with diethyl ether (50 mL) and hexanes (50 mL) to yield N-(3,4-difluorophenyl)-2-fluoro-5-(N-(prop-2-yn-1-yl)sulfamoyl)benzamide 12 (74%, 7.8 g, 21.1 mmol) as a white powder. A solution of bromocyclopropane (0.6 mL, 4.9 mmol) and sodium azide (483 mg, 7.4 mmol) in water (1 mL) was heated under microwave irradiation for 30 minutes at 120° C. To this solution were added a solution of compound 12 (0.1 g, 0.3 mmol) in acetonitrile (1 mL), sodium ascorbate (10 mg, 0.05 mmol) and copper sulfate (20 mg, 0.12 mmol).

The reaction mixture was then heated for 30 minutes at 80° C. under microwave irradiation before being poured into a saturated solution of ammonium chloride (50 mL). After extraction with EtOAc (3×50 mL), the combined organic layers were dried over sodium sulfate and concentrated in vacuo. The resulting residue was purified by flash chromatography (Hexanes:EtOAc=6:4 v/v) giving compound 13 as a white powder (19%, 23 mg, 0.05 mmol). $^1$H NMR (400 MHz, Acetone-d6) δ 9.92 (s, 1H), 8.25 (dd, J=6.6, 2.5 Hz, 1H), 8.06-7.95 (m, 2H), 7.77 (s, 1H), 7.58-7.52 (m, 1H), 7.48 (dd, J=10.1, 8.7 Hz, 1H), 7.37 (dt, J=10.6, 9.0 Hz, 1H), 7.21 (brs, 1H), 6.11-5.94 (m, 1H), 5.32-5.16 (m, 1H), 4.99 (dt, J=6.0, 1.5 Hz, 2H), 4.32 (s, 2H). $^{13}$C NMR (101 MHz, Acetone-d$_6$) δ 188.9, 167.9, 162.1, 150.2, 149.2 (d, J=12.9 Hz), 146.8 (d, J=13.0 Hz), 142.8, 137.9 (d, J=5.9 Hz), 128.5, 124.6, 120.4-118.2 (m), 117.5 (dd, J=6.0, 3.6 Hz), 110.6 (d, J=22.1 Hz), 81.5, 73.3, 33.2, 29.7, 12.8 (d, J=9.6 Hz). $^{19}$F NMR (377 MHz, Acetone-d6) δ −110.6 (s), −139.6--139.7 (m), −146.1--146.3 (m). HRMS (ESI): m/z [M+H]$^+$ calcd for $C_{19}H_{17}F_3N_5O_3S$: 452.1004, found: 452.0999.

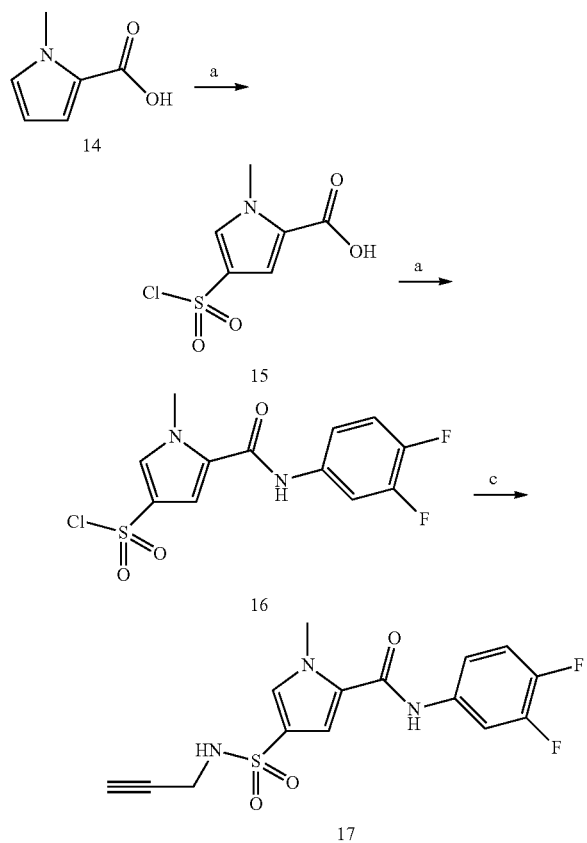

Reagents and conditions: a) HSO$_3$Cl, 0° C., 1 h; b) i) SOCl$_2$, 100° C., 1.5 h; ii) 3,4-difluoroaniline toluene, RT, 48 h; c) Propargylamine, DIPEA, DMF, RT, overnight.

N-(3,4-Difluorophenyl)-1-methyl-4-(N-(prop-2-yn-1-yl)sulfamoyl)-1H-pyrrole-2-carboxamide (17)

1-methyl-1H-pyrrole-2-carboxylic acid (10.0 g, 80 mmol) was added to chlorosulfonic acid (50 mL) at 0° C. and the resulting solution was stirred at 0° C. for 1 h. The reaction mixture was then slowly poured onto ice. The precipitate formed was then filtered, rinsed with water (3×100 mL) and dried under vacuum overnight to yield 4-(chlorosulfonyl)-1-methyl-1H-pyrrole-2-carboxylic acid 15 as a brownish solid (10.7 g, 47.8 mmol). 4-(chlorosulfonyl)-1-methyl-1H-pyrrole-2-carboxylic acid 15 (1.0 g, 4.4 mmol) was added to SOCl$_2$ at room temperature and the mixture was heated at 100° C. for 1.5 h. After removal of thionyl chloride in vacuo, the residual oil was solubilized in toluene (50 mL) and 3,4-difluoroaniline was added (650 mg, 5.0 mmol).

The solution was stirred for 48 h at room temperature before being poured into a saturated solution of ammonium chloride (50 mL). This solution was extracted with ethyl acetate (3×50 mL) and the combined organic layers were dried over sodium sulfate. After concentration in vacuo, the resulting residue was purified by flash chromatography (Hexanes:EtOAc=7:3 v/v) to yield 5-((3,4-difluorophenyl)carbamoyl)-1-methyl-1H-pyrrole-3-sulfonyl chloride 16 (775 mg, 2.3 mmol). To a solution of 5-((3,4-difluorophenyl)carbamoyl)-1-methyl-1H-pyrrole-3-sulfonyl chloride 16 (100 mg, 0.3 mmol) in DMF (5 mL) were added propargylamine hydrochloride (33 mg, 0.4 mmol) and DIPEA (78 μL, 0.5 mmol). The reaction mixture was stirred overnight at room temperature, poured into a saturated solution of ammonium chloride (50 mL) and extracted with ethyl acetate (3×50 mL). The combined organic layers were dried over sodium sulfate and concentrated in vacuo.

The resulting residue was purified by flash chromatography (Hexanes:EtOAc=7:3 v/v) to yield N-(3,4-difluorophenyl)-1-methyl-4-(N-(prop-2-yn-1-yl)sulfamoyl)-1H-pyrrole-2-carboxamide 17 (77%, 81 mg, 0.2 mmol). $^1$H NMR (400 MHz, Acetone-d$_6$) δ 9.56 (s, 1H), 8.05-7.87 (m, 1H), 7.62-7.48 (m, 2H), 7.38-7.25 (m, 1H), 7.22 (d, J=1.9 Hz, 1H), 6.57 (s, 1H), 4.03 (s, 3H), 3.79 (s, 2H), 2.70 (t, J=2.5 Hz, 1H). $^{13}$C NMR (101 MHz, Acetone-d$_6$) δ 160.9, 152.6 (d, J=13.0 Hz), 150.1 (d, J=13.2 Hz), 149.1 (d, J=12.7 Hz), 146.7 (d, J=12.8 Hz), 137.9 (dd, J=9.1, 3.0 Hz), 132.2, 128.4, 123.7, 119.7-118.4 (m), 117.8 (dd, J=5.9, 3.5 Hz), 114.0, 110.8 (d, J=22.1 Hz), 80.8, 74.5, 38.5, 34.2. $^{19}$F NMR (377 MHz, Acetone-d$_6$) δ −138.4--138.7 (m), −145.4--146.1 (m). HRMS (ESI): m/z [M+H]$^+$ calcd for $C_{15}H_{14}F_2N_3O_3S$: 354.0724, found: 354.0717.

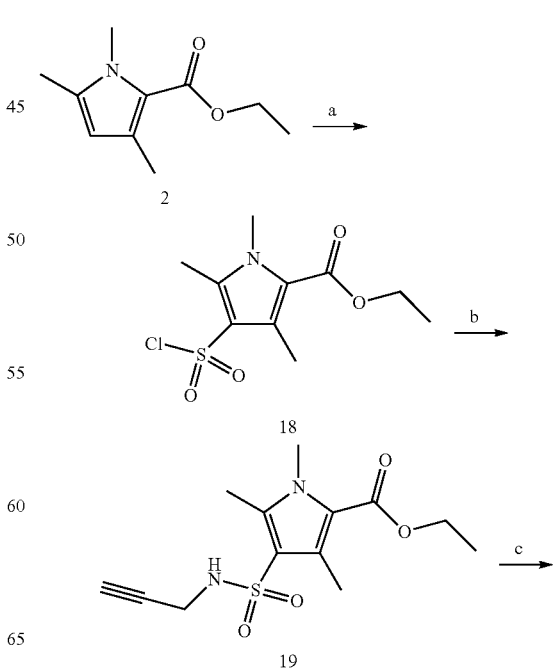

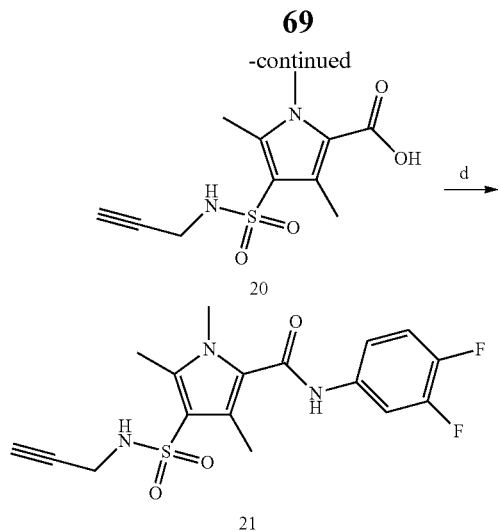

Reagents and conditions: a) HSO₃Cl, 0° C. to RT, 4 h; b) HCCCH₂NH₂, Et₃N, DMF, RT, 2 h; c) NaOH 5%, MeOH, 16 h, RT to 60° C., 18 h; d) 3,4-difluoroaniline, HATU, DIPEA, DMF, 50° C., 16 h.

1,3,5-trimethyl-4-(2-oxo-2-(prop-2-yn-1-ylamino)acetyl)-1H-pyrrole-2-carboxylic acid (20)

Ethyl 1,3,5-trimethylpyrrole-2-carboxylate 2 (2.0 g, 11.0 mmol) was added to chlorosulfonic acid (10 mL) at 0° C. and the mixture was stirred at 0° C. for 1 h then 3 h at room temperature. The reaction mixture was then slowly poured onto ice. The mixture was basified with a 5% solution of sodium hydroxide (pH>7) and extracted with ethyl acetate (3×100 mL). The organic layers were combined, dried over Na₂SO₄ and concentrated in vacuo to yield 18 a crude dark brown solid (69%, 2.1 g, 7.5 mmol). To the crude ethyl 4-(chlorosulfonyl)-1,3,5-trimethyl-1H-pyrrole-2-carboxylate intermediate 18 solubilized in DMF (10 mL) were added propargylamine (0.72 mL, 11.3 mmol) and triethylamine (3.1 mL, 22.5 mmol). The mixture was stirred at room temperature for 2 h and poured into a saturated solution of ammonium chloride (50 mL). After extraction with EtOAc (3×50 mL), the combined organic layers were dried over sodium sulfate and concentrated in vacuo. The resulting oil was diluted in methanol (5 mL) and a 5% solution of sodium hydroxide (15 mL) was added. The mixture was stirred overnight at 60° C. After removal of the methanol in vacuo, the mixture was washed with ethyl acetate (2×50 mL), acidified with a 1N HCl solution (pH=1) and extracted with ethyl acetate (3×50 mL). The combined organic layers were dried over sodium sulfate and concentrated in vacuo. The resulting solid was washed with diethyl ether (20 mL) and hexanes (20 mL) to yield 1,3,5-trimethyl-4-(2-oxo-2-(prop-2-yn-1-ylamino)acetyl)-1H-pyrrole-2-carboxylic acid 20 (28%, 0.8 g, 0.3 mmol) as an off-white powder. ¹H NMR (400 MHz, DMSO-d₆) δ 12.70 (s, 1H), 7.64 (t, J=5.9 Hz, 1H), 3.73 (s, 3H), 3.58 (dd, J=6.0, 2.6 Hz, 2H), 3.04 (t, J=2.5 Hz, 1H), 2.43 (s, 3H), 2.41 (s, 3H). ¹³C NMR (101 MHz, DMSO-d₆) δ 163.0, 138.9, 127.6, 120.8, 118.1, 80.1, 74.3, 33.4, 31.8, 12.0, 11.5.

N-(3,4-difluorophenyl)-1,3,5-trimethyl-4-(2-oxo-2-(prop-2-yn-1-ylamino)acetyl)-1H-pyrrole-2-carboxamide (21)

To a solution of 1,3,5-trimethyl-4-(2-oxo-2-(prop-2-yn-1-ylamino)acetyl)-1H-pyrrole-2-carboxylic acid 20 (0.1 g, 0.3 mmol), 3,4-difluoroaniline (96 mg, 7.4 mmol) and DIPEA (746 µL, 1.1 mmol) in DMF (15 mL) was added HATU (0.211 g, 0.5 mmol) at room temperature. The mixture was stirred at 50° C. overnight. The reaction mixture was then poured into a saturated solution of ammonium chloride (50 mL) and extracted with ethyl acetate (3×50 mL). The combined organic layers were dried over sodium sulfate, and concentrated in vacuo. The residue was purified by flash chromatography (Hexanes:EtOAc=6:4 v/v) to give compound 21 as a white powder (36%, 51 mg, 0.1 mmol). ¹H NMR (400 MHz, Acetone-d₆) δ 9.44 (s, 1H), 8.24-7.80 (m, 1H), 7.74-7.44 (m, 1H), 7.40-7.22 (m, 1H), 6.51 (d, J=6.3 Hz, 1H), 3.77-3.70 (m, 2H), 3.68 (s, 3H), 2.68-2.60 (m, 1H), 2.51 (s, 3H), 2.37 (s, 3H). ¹³C NMR (101 MHz, Acetone-d₆) δ 160.2, 150.9 (d, J=13.1 Hz), 148.4 (d, J=13.0 Hz), 147.5 (d, J=12.9 Hz), 145.1 (d, J=12.6 Hz), 137.1, 126.1, 120.7, 117.2 (d, J=18.1 Hz), 117.0, 115.8 (d, J=3.9 Hz), 108.9 (d, J=22.2 Hz), 79.1, 72.3, 31.7, 10.4, (d, J=32.3 Hz). ¹⁹F NMR (377 MHz, Acetone-d₆) δ −139.8--139.9 (m), −147.0-−147.1 (m). HRMS (ESI): m/z [M+H]⁺ calcd for C₁₇H₁₈F₂N₃O₃S: 382.1037, found: 382.1027.

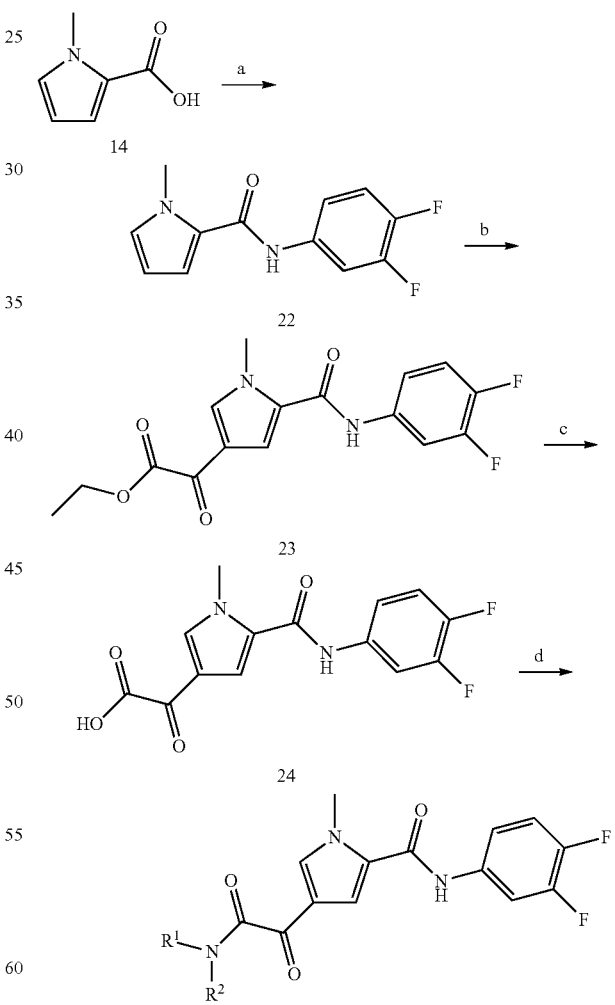

Reagents and conditions: a) HATU 3,4-difluoroaniline, DIPEA, DMF, 65° C., overnight; b) ethyl chlorooxoacetate, AlCl₃, CH₂Cl₂, 0° C. to RT, overnight; c) i) NaOH 5%, MeOH, RT, 15 min; ii) HCl, 1N; d) CDI, R¹R²NH, DMF, CH₂Cl₂, RT, 2 h.

2-(5-((3,4-difluorophenyl)carbamoyl)-1-methyl-1H-pyrrol-3-yl)-2-oxoacetic acid (24)

To a solution of 1-methyl-1H-pyrrole-2-carboxylic acid (4 g, 32 mmol), 3,4-difluoroaniline (6.2 g, 48 mmol) and DIPEA (13 mL, 96 mmol) in DMF (150 mL) was added HATU (18.2 g, 48 mmol) at room temperature. The mixture was heated at 65° C. overnight and poured into a saturated solution of ammonium chloride. After extraction with ethyl acetate (3×50 mL), the combined organic layers were dried over sodium sulfate and concentrated in vacuo. The resulting mixture was purified by flash chromatography (hexanes:EtOAc=6:4 v/v), to give compound 22 as a white powder (82%, 6.2 g, 26.2 mmol).

To a solution of N-(3,4-difluorophenyl)-1-methyl-1H-pyrrole-2-carboxamide 22 (3 g, 12.7 mmol) in $CH_2Cl_2$ (150 mL) was added dropwise, at 0° C., a solution of ethyl 2-chloro-2-oxo-acetate (2.12 mL, 19.1 mmol) in $CH_2Cl_2$ (20 mL), followed by $AlCl_3$ (5.1 g, 38.1 mmol) portion wise. The resulting mixture was stirred overnight at room temperature and then poured onto crushed ice. After addition of water (300 mL), the mixture was filtered on Celite and the aqueous layer was extracted with $CH_2Cl_2$ (3×100 mL). The combined organic layers were washed with a saturated solution of sodium carbonate (100 mL), a saturated solution of ammonium chloride (100 mL), dried over $Na_2SO_4$ and concentrated in vacuo. The resulting oil was diluted in methanol/THF (v/v=1/2, 30 mL) and a 5% solution of sodium hydroxide (30 mL) was added. After being stirred for 15 min at room temperature, the mixture was concentrated in vacuo. The mixture was washed with ethyl acetate (2×50 mL), acidified with a 1N HCl solution (pH=1) and extracted with ethyl acetate (3×50 mL). The combined organic layers were dried over sodium sulfate, and concentrated in vacuo. The resulting solid was washed with diethyl ether (20 mL) and hexanes (20 mL) to yield 2-(5-((3,4-difluorophenyl)carbamoyl)-1-methyl-1H-pyrrol-3-yl)-2-oxoacetic acid 24 (3.48 g, 11.3 mmol) as an off-white powder. $^1H$ NMR (400 MHz, DMSO-$d_6$) δ 10.28 (s, 1H), 8.02 (d, J=1.9 Hz, 1H), 7.94-7.81 (m, 1H), 7.60 (d, J=1.9 Hz, 1H), 7.56-7.47 (m, 1H), 7.44-7.24 (m, 1H), 3.96 (s, 3H). $^{13}C$ NMR (101 MHz, DMSO-$d_6$) δ 181.1, 165.3, 159.5, 150.5 (d, J=13.1 Hz), 148.0 (d, J=13.1 Hz), 147.0 (d, J=12.5 Hz), 144.6 (d, J=12.6 Hz), 136.6, 136.4 (dd, J=9.2, 2.8 Hz), 127.9, 119.0, 117.7 (d, J=17.7 Hz), 116.8 (dd, J=5.8, 3.2 Hz), 114.9, 109.4 (d, J=21.7 Hz), 37.7. $^{19}F$ NMR (377 MHz, DMSO-$d_6$) δ −138.0--138.2 (m), −145.5--145.6 (m).

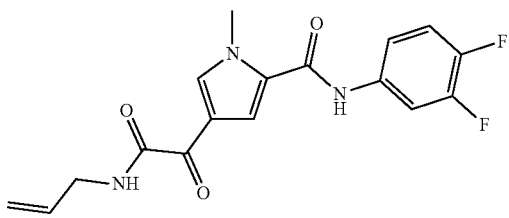 [SMILES: C=CCNC(=O)C(=O)c1cc(C(=O)Nc2ccc(F)c(F)c2)n(C)c1]

4-(2-(allylamino)-2-oxoacetyl)-N-(3,4-difluorophenyl)-1-methyl-1H-pyrrole-2-carboxamide (25)

To a solution of 2-(5-((3,4-difluorophenyecarbamoyl)-1-methyl-1H-pyrrol-3-yl)-2-oxoacetic acid 24 (0.1 g, 0.3 mmol) in DMF (4 mL) and $CH_2Cl_2$ (5 mL) were added 1,1'-carbonyldiimidazole (79 mg, 0.05 mmol) and allylamine (29 μL, 0.4 mmol) at room temperature. The mixture was stirred for 2 h at room temperature and poured into a saturated solution of ammonium chloride. After extraction with $CH_2Cl_2$ (3×20 mL), the combined organic layers were dried over sodium sulfate and concentrated in vacuo. The resulting residue was purified by flash chromatography (Hexanes:EtOAc=7:3 v/v) to afford 4-(2-(allylamino)-2-oxoacetyl)-N-(3,4-difluorophenyl)-1-methyl-1H-pyrrole-2-carboxamide 25 as an off-white powder (81%, 91 mg, 0.2 mmol). $^1H$ NMR (400 MHz, Acetone-$d_6$) δ 9.60 (s, 1H), 8.23 (s, 1H), 8.14 (s, 1H), 8.04-7.90 (m, 1H), 7.58 (s, 1H), 7.57-7.49 (m, 1H), 7.30 (q, J=9.6 Hz, 1H), 6.25-5.68 (m, 1H), 5.22 (d, J=16.8 Hz, 1H), 5.11 (dt, J=10.3, 1.4 Hz, 1H), 4.06 (s, 3H), 3.99-3.92 (m, 2H). $^{13}C$ NMR (101 MHz, Acetone-$d_6$) δ 182.7, 163.7, 161.1, 152.6 (d, J=13.1 Hz), 150.2 (d, J=12.9 Hz), 149.1 (d, J=12.8 Hz), 146.7 (d, J=12.9 Hz), 138.9, 137.9, 136.2, 129.0, 120.9, 118.8 (d, J=18.0 Hz), 117.9-117.4 (m), 117.0, 116.6, 110.7 (d, J=22.1 Hz), 42.9, 38.7. $^{19}F$ NMR (377 MHz, Acetone-$d_6$) δ −138.5--138.8 (m), −145.9--146.2 (m). HRMS (ESI): m/z [M+H]+ calcd for $C_{17}H_{16}F_2N_3O_3$: 348.1260, found: 348.1158.

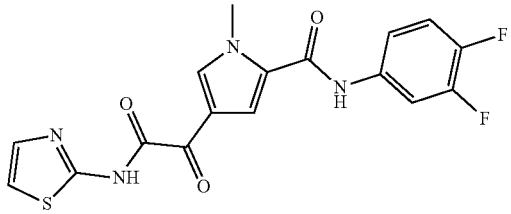 [SMILES: Cn1cc(C(=O)C(=O)Nc2nccs2)cc1C(=O)Nc1ccc(F)c(F)c1]

N-(3,4-difluorophenyl)-1-methyl-4-(2-oxo-2-(thiazol-2-ylamino)acetyl)-1H-pyrrole-2-carboxamide (26)

To a solution of 2-(5-((3,4-difluorophenyecarbamoyl)-1-methyl-1H-pyrrol-3-yl)-2-oxoacetic acid 24 (0.1 g, 0.3 mmol) in DMF (4 mL) and $CH_2Cl_2$ (5 mL) were added 1,1'-carbonyldiimidazole (79 mg, 0.05 mmol) and thiazole-2-amine (33 mg, 0.4 mmol) at room temperature. The mixture was stirred for 2 h at room temperature and poured into a saturated solution of ammonium chloride. After extraction with $CH_2Cl_2$ (3×20 mL), the combined organic layers were dried over sodium sulfate and concentrated in vacuo. The resulting residue was purified by flash chromatography (Hexanes:EtOAc=7:3 v/v) to afford N-(3,4-difluorophenyl)-1-methyl-4-(2-oxo-2-(thiazol-2-ylamino)acetyl)-1H-pyrrole-2-carboxamide 26 as an brownish powder (79%, 101 mg, 0.2 mmol). $^1H$ NMR (400 MHz, DMSO-$d_6$) δ 12.74 (s, 1H), 10.33 (s, 1H), 8.20 (s, 1H), 7.94-7.83 (m, 1H), 7.69 (s, 1H), 7.60 (d, J=3.6 Hz, 1H), 7.56-7.49 (m, 1H), 7.48-7.38 (m, 1H), 3.98 (s, 3H). $^{13}C$ NMR (101 MHz, DMSO-$d_6$) δ 180.6, 162.5, 159.5, 150.5 (d, J=12.9 Hz), 148.1 (d, J=12.5 Hz), 138.6, 137.2, 136.4 (d, J=12.0 Hz), 127.9, 118.7, 117.8 (d, J=17.6 Hz), 116.8, 109.5 (d, J=21.7 Hz), 60.2, 37.8, 17.9 (d, J=672.1 Hz). $^{19}F$ NMR (377 MHz, DMSO-$d_6$) δ −137.3--137.4 (m), −144.5--144.7 (m). HRMS (ESI): m/z [M+H]+ calcd for $C_{17}H_{13}F_2N_4O_3S$: 391.0676, found: 391.0669.

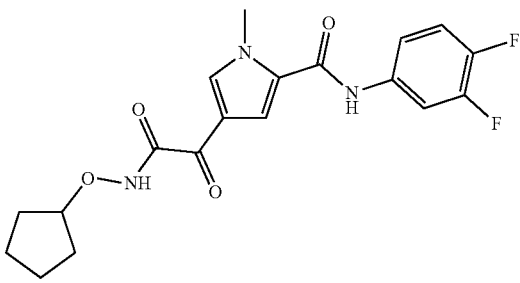 [SMILES: Cn1cc(C(=O)C(=O)NOC2CCCC2)cc1C(=O)Nc1ccc(F)c(F)c1]

4-(2-((cyclopentyloxy)amino)-2-oxoacetyl)-N-(3,4-difluorophenyl)-1-methyl-1H-pyrrole-2-carboxamide (27)

To a solution of 2-(5-((3 difluorophenyl)carbamoyl)-1-methyl-1H-pyrrol-3-yl)-2-oxoacetic acid 24 (0.1 g, 0.3 mmol) in DMF (4 mL) and $CH_2Cl_2$ (5 mL) were added 1,1'-carbonyldiimidazole (79 mg, 0.05 mmol) and O-cyclopentylhydroxylamine hydrochloride (44 mg, 0.4 mmol) at room temperature. The mixture was stirred for 2 h at room temperature and poured into a saturated solution of ammonium chloride. After extraction with $CH_2Cl_2$ (3×20 mL), the combined organic layers were dried over sodium sulfate and concentrated in vacuo. The resulting residue was purified by flash chromatography (Hexane:EtOAc=7:3 v/v) to give 4-(2-((cyclopentyloxy)amino)-2-oxoacetyl)-N-(3,4-difluorophenyl)-1-methyl-1H-pyrrole-2-carboxamide 27 as a brownish powder (26%, 33 mg, 0.1 mmol). $^1$H NMR (400 MHz, Acetone-$d_6$) δ 10.83 (s, 1H), 9.63 (s, 1H), 8.14 (d, J=1.7 Hz, 1H), 8.03-7.90 (m, 1H), 7.65-7.46 (m, 2H), 7.40-7.20 (m, 1H), 4.69-4.57 (m, 1H), 4.06 (s, 3H), 1.95-1.85 (m, 2H), 1.79-1.65 (m, 4H), 1.57 (s, 2H). $^{13}$C NMR (101 MHz, Acetone-$d_6$) δ 181.0, 161.2 (d, J=178.9 Hz), 159.7, 159.3, 150.8 (d, J=13.2 Hz), 148.3 (d, J=13.2 Hz), 147.3 (d, J=12.8 Hz), 144.9 (d, J=12.7 Hz), 136.8, 136.2 (dd, J=9.1, 3.0 Hz), 127.4, 119.2, 117.0 (d, J=18.0 Hz), 116.5-115.7 (m), 114.5, 109.1 (d, J=22.2 Hz), 87.4, 87.0, 37.0, 30.9, 23.4. $^{19}$F NMR (377 MHz, Acetone-$d_6$) δ -138.6--138.7 (m), -146.0--146.1 (m). HRMS (ESI): m/z [M+H]$^+$ calcd for $C_{19}H_{20}F_2N_3O_4$: 392.1422, found: 392.1415.

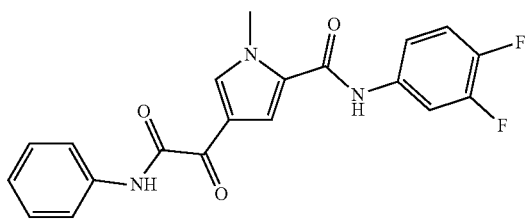 [SMILES: Cn1cc(C(=O)C(=O)Nc2ccccc2)cc1C(=O)Nc1ccc(F)c(F)c1]

N-(3,4-difluorophenyl)-1-methyl-4-(2-oxo-2-(phenylamino)acetyl)-1H-pyrrole-2-carboxamide (28)

To a solution of 2-(5-((3,4-difluorophenyecarbamoyl)-1-methyl-1H-pyrrol-3-yl)-2-oxoacetic acid 24 (0.1 g, 0.3 mmol) in DMF (4 mL) and $CH_2Cl_2$ (5 mL) were added 1,1'-carbonyldiimidazole (79 mg, 0.05 mmol) and aniline (35 μL, 0.4 mmol) at room temperature. The mixture was stirred for 2 h at room temperature and poured into a saturated solution of ammonium chloride. After extraction with $CH_2Cl_2$ (3×20 mL), the combined organic layers were dried over sodium sulfate and concentrated in vacuo. The resulting residue was purified by flash chromatography (Hexanes:EtOAc=7:3 v/v) to afford N-(3,4-difluorophenyl)-1-methyl-4-(2-oxo-2-(phenylamino)acetyl)-1H-pyrrole-2-carboxamide 28 as a white powder (32%, 40 mg, 0.1 mmol). $^1$H NMR (400 MHz, Acetone-$d_6$) δ 9.79 (s, 1H), 9.64 (s, 1H), 8.30 (s, 1H), 8.04-7.94 (m, 1H), 7.93 (s, 1H), 7.91 (s, 1H), 7.63 (d, J=1.8 Hz, 1H), 7.60-7.52 (m, 1H), 7.44-7.37 (m, 2H), 7.36-7.27 (m, 1H), 7.22-7.14 (m, 1H), 4.10 (s, 3H). $^{13}$C NMR (101 MHz, Acetone-$d_6$) δ 182.4, 162.0, 161.1, 152.6 (d, J=13.0 Hz), 150.2 (d, J=13.2 Hz), 149.1 (d, J=12.5 Hz), 146.7 (d, J=12.8 Hz), 139.7, 139.1, 138.0 (dd, J=9.2, 2.9 Hz), 130.6, 129.2, 126.3, 121.8, 120.5, 118.9 (d, J=17.9 Hz), 117.8 (dd, J=5.9, 3.5 Hz), 116.7, 110.9 (d, J=22.3 Hz), 38.8. $^{19}$F NMR (377 MHz, Acetone-$d_6$) δ -138.6--138.9 (m), -146.1--146.2 (m). HRMS (ESI): m/z [M+H]$^+$ calcd for $C_{20}H_{16}F_2N_3O_3$: 384.116, found: 384.1153.

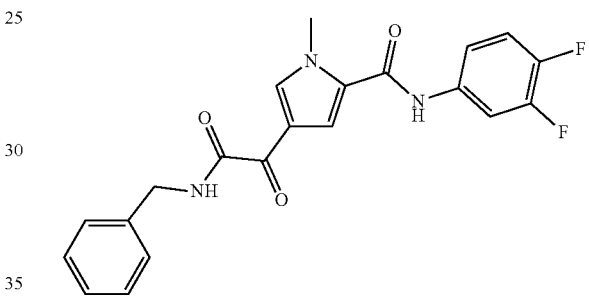

N-(3,4-difluorophenyl)-1-methyl-4-(2-oxo-2-(phenylamino)acetyl)-1H-pyrrole-2-carboxamide (29)

To a solution of 2-(5-((3,4-difluorophenyl)carbamoyl)-1-methyl-H-pyrrol-3-yl)-2-oxoacetic acid 24 (0.1 g, 0.3 mmol), in DMF (4 mL) and $CH_2Cl_2$ (5 mL) were added 1,1'-carbonyldiimidazole (79 mg, 0.05 mmol) and benzylamine (42 μL, 0.4 mmol) at room temperature. The mixture was stirred for 2 h at room temperature and poured into a saturated solution of ammonium chloride. After extraction with $CH_2Cl_2$ (3×20 mL), the combined organic layers were dried over sodium sulfate and concentrated in vacuo. The resulting residue was purified by flash chromatography (Hexane:EtOAc=7:3 v/v) to afford N-(3,4-difluorophenyl)-1-methyl-4-(2-oxo-2-(phenylamino)acetyl)-1H-pyrrole-2-carboxamide 29 as a white powder (99%, 126 mg, 0.2 mmol). $^{13}$C NMR (101 MHz, Acetone-$d_6$) δ 182.7, 163.9, 161.1, 159.9, 152.6 (d, J=13.0 Hz), 150.1 (d, J=13.3 Hz), 149.1 (d, J=12.7 Hz), 146.7 (d, J=12.8 Hz), 142.8, 140.7, 139.0, 138.0 (d, J=12.1 Hz), 130.2, 130.0, 129.4, 129.0, 128.9, 128.4, 120.9, 118.8 (d, J=18.3 Hz), 118.3-117.5 (m), 116.7, 110.8 (d, J=22.2 Hz), 45.3, 44.3, 38.8. $^{19}$F NMR (377 MHz, Acetone-$d_6$) δ -138.7--138.8 (m), -146.1--146.4 (m). HRMS (ESI): m/z [M+H]$^+$ calcd for $C_{21}H_{18}F_2N_3O_3$: 398.1316, found: 398.1312.

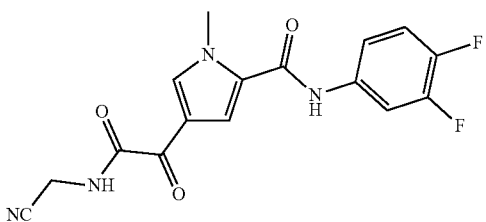 [SMILES: Cn1cc(C(=O)C(=O)NCC#N)cc1C(=O)Nc1ccc(F)c(F)c1]

4-(2-((cyanomethyl)amino)-2-oxoacetyl)-N-(3,4-difluorophenyl)-1-methyl-1H-pyrrole-2-carboxamide (30)

To a solution of 2-(5-((3,4-difluorophenyl)carbamoyl)-1-methyl-H-pyrrol-3-yl)-2-oxoacetic acid 24 (0.1 g, 0.3 mmol), in DMF (4 mL) and $CH_2Cl_2$ (5 mL) were added 1,1'-carbonyldiimidazole (79 mg, 0.05 mmol) and 2-aminoacetonitrile hydrochloride (36 mg, 0.4 mmol) at room temperature. The mixture was stirred for 2 h at room temperature and poured into a saturated solution of ammonium chloride. After extraction with $CH_2Cl_2$ (3×20 mL), the combined organic layers were dried over sodium sulfate and concentrated in vacuo. The resulting residue was purified by flash chromatography (Hexanes:EtOAc=7:3 v/v) to afford 4-(2-((cyanomethyl)amino)-2-oxoacetyl)-N-(3,4-difluorophenyl)-1-methyl-1H-pyrrole-2-carboxamide 30 as a brownish powder (30%, 34 mg, 0.1 mmol). $^1$H NMR (400 MHz, Acetone-$d_6$) δ 9.43 (s, 1H), 8.07 (s, 1H), 8.06-7.71 (m, 1H), 7.54-7.40 (m, 1H), 7.37-7.12 (m, 1H), 6.93 (s, 1H), 6.88-6.84 (m, 1H), 3.93 (s, 3H), 3.66-3.43 (m, 1H), 1.99-1.93 (m, 3H), 1.79-1.68 (m, 2H), 1.67-1.55 (m, 2H). $^{13}$C NMR (101 MHz, Acetone-$d_6$) δ 181.1, 164.1, 161.1, 139.0, 129.3, 120.5, 118.9 (d, J=17.6 Hz), 118.0, 117.8 (dd, J=6.0, 3.2 Hz), 116.6, 110.9 (d, J=22.1 Hz), 38.8, 28.8. $^{19}$F NMR (377 MHz, Acetone-$d_6$) δ −138.7--138.8 (m), −145.9--146.2 (m). HRMS (ESI): m/z [M+H]$^+$ calcd for $C_{17}H_{20}F_2N_3O_3S$: 384.1193, found: 384.1186.

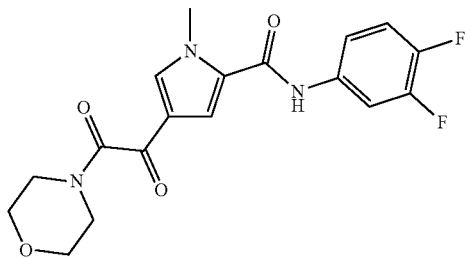 [SMILES: Cn1cc(C(=O)C(=O)N2CCOCC2)cc1C(=O)Nc1ccc(F)c(F)c1]

N-(3,4-difluorophenyl)-1-methyl-4-(2-morpholino-2-oxoacetyl)-1H-pyrrole-2-carboxamide (31)

To a solution of 2-(5-((3,4-difluorophenyl)carbamoyl)-1-methyl-1H-pyrrol-3-yl)-2-oxoacetic acid 24 (0.1 g, 0.3 mmol), in DMF (4 mL) and $CH_2Cl_2$ (5 mL) were added 1,1'-carbonyldiimidazole (79 mg, 0.05 mmol) and morpholine (34 μL, 0.4 mmol) at room temperature. The mixture was stirred for 2 h at room temperature and poured into a saturated solution of ammonium chloride. After extraction with $CH_2Cl_2$ (3×20 mL), the combined organic layers were dried over sodium sulfate and concentrated in vacuo. The resulting residue was purified by flash chromatography (Hexanes:EtOAc=7:3 v/v) to afford N-(3,4-difluorophenyl)-1-methyl-4-(2-morpholino-2-oxoacetyl)-1H-pyrrole-2-carboxamide 31 as a white powder (80%, 97 mg, 0.2 mmol). $^1$H NMR (400 MHz, DMSO-$d_6$) δ 10.28 (s, 1H), 8.19-7.80 (m, 2H), 7.57-7.47 (m, 2H), 7.46-7.36 (m, 1H), 3.95 (s, 3H), 3.81-3.67 (m, 2H), 3.64-3.59 (m, 2H), 3.58-3.49 (m, 2H), 3.34-3.25 (m, 2H). $^{13}$C NMR (101 MHz, DMSO-$d_6$) δ 185.9, 165.8, 159.5, 150.5 (d, J=13.1 Hz), 148.1 (d, J=13.2 Hz), 147.1 (d, J=12.8 Hz), 144.7 (d, J=12.8 Hz), 136.4 (dd, J=9.1, 3.0 Hz), 135.9, 128.1, 119.8, 117.8 (d, J=17.7 Hz), 117.2-116.3 (m), 114.0, 109.5 (d, J=21.7 Hz), 66.5 (d, J=30.5 Hz), 46.3, 41.5, 37.8. $^{19}$F NMR (377 MHz, DMSO-$d_6$) δ −137.2--137.4 (m), −144.5--144.6 (m). HRMS (ESI): m/z [M+H]$^+$ calcd for $C_{18}H_{18}F_2N_3O_4$: 378.1265, found: 378.1257.

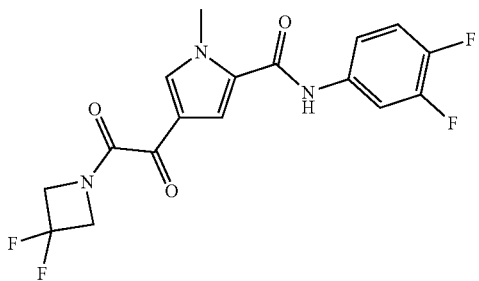 [SMILES: Cn1cc(C(=O)C(=O)N2CC(F)(F)C2)cc1C(=O)Nc1ccc(F)c(F)c1]

4-(2-(3,3-difluoroazetidin-1-yl)-2-oxoacetyl)-N-(3,4-difluorophenyl)-1-methyl-1H-pyrrole-2-carboxamide (32)

To a solution of 2-(5-((3,4-difluorophenyl)carbamoyl)-1-methyl-H-pyrrol-3-yl)-2-oxoacetic acid 24 (0.1 g, 0.3 mmol), in DMF (4 mL) and $CH_2Cl_2$ (5 mL) were added 1,1'-carbonyldiimidazole (79 mg, 0.05 mmol) and 3,3-difluoroazetidine hydrochloride (50 mg, 0.4 mmol) at room temperature. The mixture was stirred for 2 h at room temperature and poured into a saturated solution of ammonium chloride. After extraction with $CH_2Cl_2$ (3×20 mL), the combined organic layers were dried over sodium sulfate and concentrated in vacuo. The resulting residue was purified by flash chromatography (Hexanes:EtOAc=7:3 v/v) to afford 4-(2-(3,3-difluoroazetidin-1-yl)-2-oxoacetyl)-N-(3,4-difluorophenyl)-1-methyl-1H-pyrrole-2-carboxamide 32 as a white powder (48%, 60 mg, 0.1 mmol). $^1$H NMR (400 MHz, Acetone-$d_6$) δ 9.60 (s, 1H), 8.06 (d, J=1.7 Hz, 1H), 8.01-7.86 (m, 1H), 7.70-7.47 (m, 2H), 7.34-7.26 (m, 1H), 4.98-4.79 (m, 2H), 4.65-4.31 (m, 2H), 4.05 (s, 3H). $^{13}$C NMR (101 MHz, Acetone-$d_6$) δ 182.6, 163.7, 161.1, 152.6 (d, J=13.1 Hz), 150.2 (d, J=13.6 Hz), 149.1 (d, J=12.8 Hz), 146.7 (d, J=13.1 Hz), 138.4, 138.2-137.6 (m), 129.2, 121.4, 121.0, 118.9 (d, J=17.9 Hz), 118.3, 118.0-117.5 (m), 116.2, 115.6, 110.8 (d, J=22.2 Hz), 65.8 (t, J=28.6 Hz), 61.9 (t, J=28.7 Hz), 38.8. $^{19}$F NMR (377 MHz, Acetone-$d_6$) δ −102.1 (p, J=12.3 Hz), −138.7--138.8 (m), −146.0--146.2 (m). HRMS (ESI): m/z [M+H]$^+$ calcd for $C_{17}H_{14}F_4N_3O_3$: 384.0971, found: 384.0964.

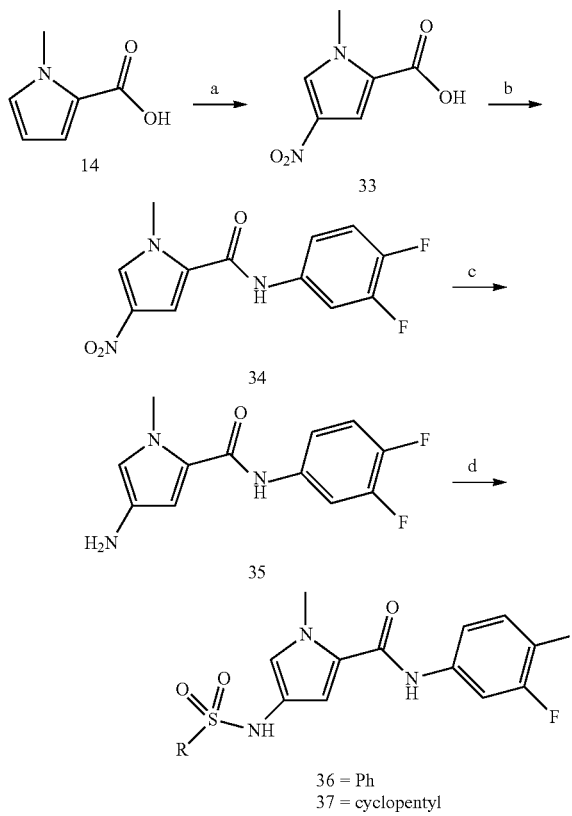

Reagents and conditions: a) HNO₃, Ac₂O, -25° C. to RT, 2 h; b) HATU, DIPEA, 3,4-difluoroaniline, DMF, 50° C., overnight; c) Zn, HCOOH, MeOH, RT, 10 min; d) RSO₂Cl, Et₃N, DMF, RT, overnight.

N-(3,4-difluorophenyl)-1-methyl-4-(phenylsulfonamido)-1H-pyrrole-2-carboxamide (36)

To a solution of 1-methyl-1H-pyrrole-2-carboxylic acid 14 (4 g, 32 mmol) in acetic anhydride (40 mL) was added nitric acid 70% (3.2 mL) at −25° C. The reaction was allowed to warm up to room temperature and was stirred for 2 h. After addition of water (200 mL) at −25° C., the mixture was extracted with ethyl acetate (3×50 mL).

The combined organic layers were washed with a saturated solution of sodium carbonate (3×100 mL), dried over sodium sulfate, and concentrated in vacuo. The residue was purified by flash chromatography (Hexanes:EtOAc=4:6 v/v) to give compound 33 as a dark oil (14%, 770 mg, 4.5 mmol). To a solution of 1-methyl-4-nitro-1H-pyrrole-2-carboxylic acid 33 (0.77 g, 4.5 mmol), 3,4-difluoroaniline (1.16 g, 9.0 mmol) and DIPEA (1.85 mL, 13.6 mmol) in DMF (20 mL) was added HATU (1.89 g, 5.0 mmol) at room temperature. The reaction mixture was stirred at 50° C. overnight and then poured into a saturated solution of ammonium chloride (50 mL). After extraction with ethyl acetate (3×50 mL), the combined organic layers were dried over sodium sulfate and concentrated in vacuo. The residue was purified by flash chromatography (Hexanes:EtOAc=7:3 v/v) to give N-(3,4-difluorophenyl)-1-methyl-4-nitro-1H-pyrrole-2-carboxamide 34 (64%, 820 mg, 2.9 mmol). To a suspension of N-(3,4-difluorophenyl)-1-methyl-4-nitro-1H-pyrrole-2-carboxamide 34 (250 mg, 0.9 mmol) in methanol (20 mL) and formic acid (0.5 mL, 13.3 mmol) was added Zn dust (250 mg, 3.8 mmol). The mixture was stirred for 10 minutes at room temperature and filtered on Celite. The solution was extracted with HCl 1N (3×50 mL) and washed with ethyl acetate (2×50 mL). The aqueous layer was then basified using a 5% solution of sodium hydroxide (pH>8) and extracted with ethyl acetate (3×50 mL).

The combined organic layers were dried over sodium sulfate and concentrated in vacuo to give 4-amino-N-(3,4-difluorophenyl)-1-methyl-1H-pyrrole-2-carboxamide 35 as a brown/yellowish solid (68%, 153 mg, 0.6 mmol). To a solution of 4-amino-N-(3,4-difluorophenyl)-1-methyl-H-pyrrole-2-carboxamide 35 (25 mg, 0.1 mmol) in DMF (3 mL) were added benzenesulfonylchloride (14 μL, 0.1 mmol) and Et₃N (20 μL, 0.2 mmol). The reaction mixture was stirred overnight at room temperature and then poured into a saturated solution of ammonium chloride (20 mL). After extraction with EtOAc (3×20 mL), the combined organic layers were dried over sodium sulfate and concentrated in vacuo. The residue was purified by flash chromatography (Hexanes:EtOAc=1:1 v/v) to give compound 36 (51%, 20 mg, 0.05 mmol). $^1$H NMR (400 MHz, Acetone-$d_6$) δ 9.37 (s, 1H), 8.53 (s, 1H), 8.05-7.85 (m, 1H), 7.81-7.71 (m, 2H), 7.68-7.58 (m, 1H), 7.58-7.51 (m, 2H), 7.45-7.41 (m, 1H), 7.35-7.17 (m, 1H), 6.77 (d, J=2.0 Hz, 1H), 6.72 (d, J=2.0 Hz, 1H), 3.86 (s, 3H). $^{13}$C NMR (101 MHz, Acetone-$d_6$) δ 161.3, 141.9, 134.3, 130.6, 128.8, 125.6, 124.2, 121.9, 118.7 (d, J=17.9 Hz), 118.1-117.4 (m), 110.7 (d, J=22.1 Hz), 110.2, 38.0. $^{19}$F NMR (377 MHz, Acetone-$d_6$) δ −140.2--−140.4 (m), −147.9--−148.1 (m). HRMS (ESI): m/z [M+H]⁺ calcd for $C_{18}H_{16}F_2N_3O_3S$: 392.0880, found: 392.0872.

4-(cyclopentanesulfonamido)-N-(3,4-difluorophenyl)-1-methyl-1H-pyrrole-2-carboxamide (37)

To a solution of 4-amino-N-(3,4-difluorophenyl)-1-methyl-1H-pyrrole-2-carboxamide 35 (50 mg, 0.2 mmol) in DMF (5 mL) were added cyclopentylsulfonylchloride (51 μL, 0.4 mmol) and Et₃N (40 μL, 0.3 mmol). The reaction mixture was stirred overnight at room temperature and then poured into a saturated solution of ammonium chloride (30 mL). After extraction with EtOAc (3×30 mL), the combined organic layers were dried over sodium sulfate and concentrated in vacuo. The residue was purified by flash chromatography (Hexanes:EtOAc=1:1 v/v) to give compound 37 (56%, 43 mg, 0.1 mmol). $^1$H NMR (400 MHz, Acetone-$d_6$) δ 9.43 (s, 1H), 8.07 (s, 1H), 8.06-7.71 (m, 1H), 7.54-7.40 (m, 1H), 7.37-7.12 (m, 1H), 6.93 (s, 1H), 6.88-6.84 (m, 1H), 3.93 (s, 3H), 3.66-3.43 (m, 1H), 1.99-1.93 (m, 3H), 1.79-1.68 (m, 2H), 1.67-1.55 (m, 2H). $^{19}$F NMR (377 MHz, Acetone-$d_6$) δ −140.2--−140.4 (m), −148.0--−148.1 (m). HRMS (ESI): m/z [M+H]⁺ calcd for $C_{17}H_{20}F_2N_3O_3S$: 384.1193, found: 384.1186.

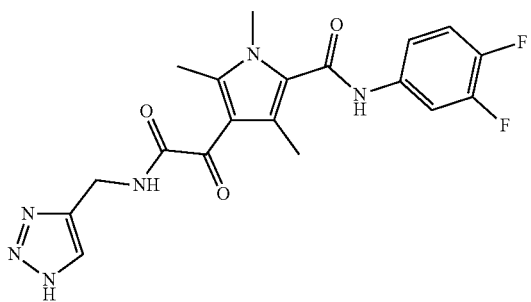 [SMILES: Cc1c(C(=O)C(=O)NCc2c[nH]nn2)c(C)n(C)c1C(=O)Nc1ccc(F)c(F)c1]

4-(2-(((1H-1,2,3-triazol-4-yl)methyl)amino)-2-oxoacetyl)-N-(3,4-difluorophenyl)-1,3,5-trimethyl-1H-pyrrole-2-carboxamide (38)

To a solution of 7a in an ACN/H$_2$O mixture (2 mL, 1:1) were added sodium azide (26 mg, 0.4 mmol), CuSO$_4$.5H$_2$O (5 mg) and sodium ascorbate (12 mg). The reaction mixture was heated at 150° C. under microwave irradiation for 1 h. The solution was diluted with EtOAc and washed with water. The organic layer was dried over MgSO$_4$ and concentrated in vacuo. The residue was purified by silica gel column chromatography using DCM/MeOH (95:5) to afford 38 in 41% yield (23 mg). HRMS (ESI): m/z [M+H]$^+$ calcd for C$_{19}$H$_{19}$F$_2$N$_6$O$_3$: 417.1487, found: 417.1476.

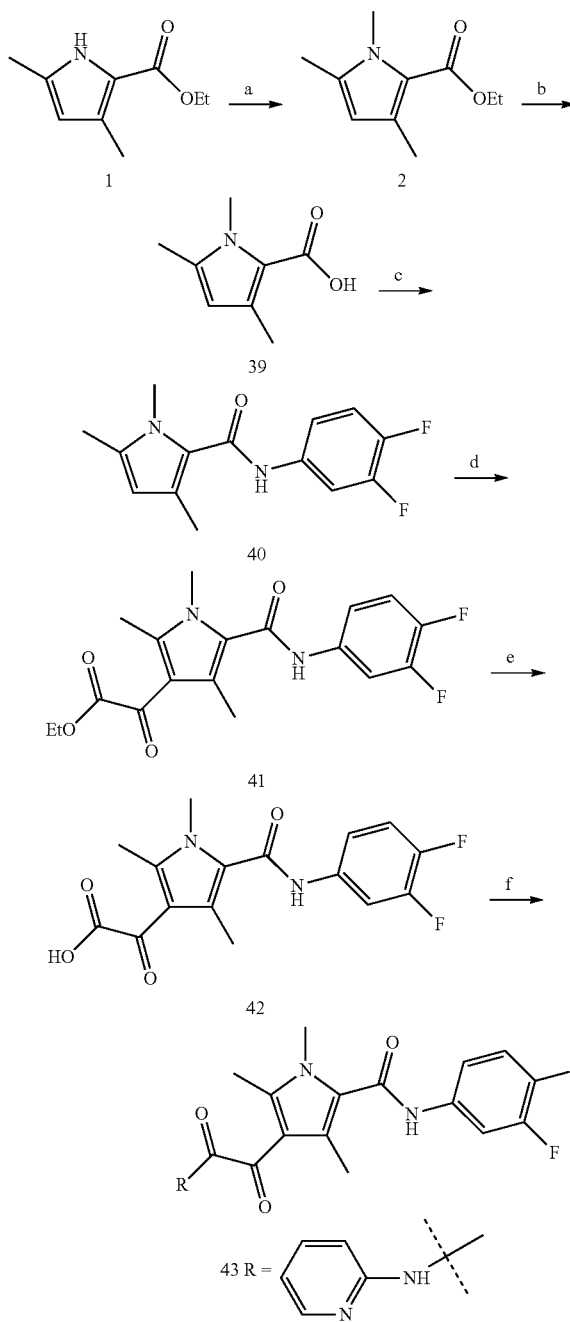

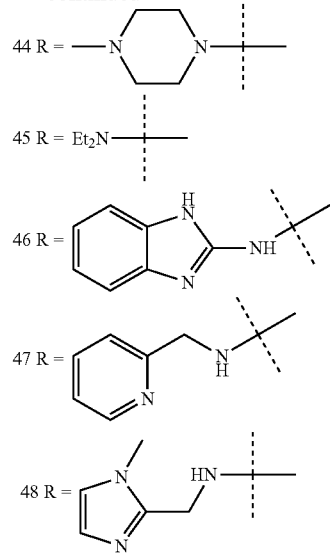

Reagents and conditions: a) MeI, KOH, DMSO; b) NaOH, EtOH, 100° C., 6 h; c) 3,4-difluoroaniline, HATU, DIPEA, DMF, 60° C.; d) ethyl oxalyl chloride, AlCl$_3$, DCM, 0° C. to rt, 16 h; e) NaOH, EtOH, rt, 1 h; f) amine, CDI, DMF DCM, rt, 1 h.

1,3,5-Trimethyl-1H-pyrrole-2-carboxylic acid (39)

To a solution of 2 (3 g, 72 mmol) in EtOH (100 mL) was added NaOH 20% (70 mL). The reaction was heated at 100° C. for 6 h. EtOH was evaporated under vacuum and the mixture was washed with DCM (3×30 mL). The aqueous layer was carefully acidified to pH 3-4 with 1M HCl. The mixture was extracted with DCM (3×30 mL). Combined organic layers were dried over MgSO$_4$ and concentrated in vacuo. The resulting solid was washed with cold Et$_2$O to afford 39 in 61% yield (6.7 g) as a pink solid. $^1$H NMR (400 MHz, DMSO-d$_6$) δ 11.88 (s, 1H), 5.75 (s, 1H), 3.68 (s, 3H), 2.19 (s, 3H), 2.15 (s, 3H). MS (ESI): m/z [M+H]$^+$ calcd for C$_8$H$_{12}$NO$_2$: 154.1, found: 154.5.

N-(3,4-difluorophenyl)-1,3,5-trimethyl-1H-pyrrole-2-carboxamide (40)

To a solution of 39 (2.9 g, 18.9 mmol) in DMF (20 mL) were added 3,4-difluoroaniline (4.5 mL, 22.7 mmol), HATU (8.6 g, 22.7 mmol) and DIPEA (6.6 mL, 37.8 mmol) at 0° C. The mixture was heated at 60° C. for 2 days. The reaction mixture was then diluted with EtOAC and washed with 1M HCl, water and brine. The organic layers was dried over MgSO$_4$ and concentrated in vacuo. The residue was purified by silica gel column chromatography using hexanes/EtOAc (8:2) to afford 40 in 37% yield (1.85 g). $^1$H NMR (400 MHz, Chloroform-d) δ 7.76-7.65 (m, 1H), 7.19-7.07 (m, 2H), 5.80 (s, 1H), 3.77 (s, 3H), 2.38 (s, 3H), 2.24 (s, 3H). MS (ESI): m/z [M+H]$^+$ calcd for C$_{14}$H$_{14}$F$_2$N$_2$O: 264.1, found: 265.5.

2-(5-((3,4-Difluorophenyl)carbamoyl)-1,2,4-trimethyl-1H-pyrrol-3-yl)-2-oxoacetic acid (42)

To a solution of 40 (860 mg, 3.26 mmol) in DCM (30 mL) were added ethyl oxalylchloride (980 μL, 8.80 mmol) and AlCl$_3$ (1.08 g, 8.15 mmol) at 0° C. The mixture was stirred at room temperature for 16 h and poured into crushed ice. The mixture was extracted with DCM and combined organic layers were filtered on Celite. The filtrate was concentrated and the resulting residue was used in the next step without further purification. To a solution of crude 41 in EtOH was added NaOH 10% (25 mL). The mixture was stirred for 1 h at room temperature. EtOH was evaporated under vacuum and the mixture was extracted with EtOAc (3×10 mL). The aqueous layer was acidified with 1M HCl. The mixture was extracted with EtOAc (3×10 mL). Combined organic layers were dried over MgSO$_4$ and concentrated in vacuo. The resulting solid was washed with Et$_2$O to afford 42 in 59% yield (646 mg) over two steps. $^1$H NMR (400 MHz, DMSO-d$_6$) δ 14.13 (s, 1H), 10.46 (s, 1H), 8.04-7.71 (m, 1H), 7.59-7.28 (m, 2H), 3.60 (s, 3H), 2.46 (s, 3H), 2.26 (s, 3H). MS (ESI): m/z [M+H]$^+$ calcd for C$_{16}$H$_{15}$F$_2$N$_2$O$_4$: 337.1, found: 337.5.

General Procedure for the Synthesis of 43-48

To a solution of 42 (40 mg, 0.119 mmol) in a DMF/DCM mixture (2 mL, 1:1) was added CDI (29 mg, 0.178 mmol) at room temperature. After 15 min, the amine (0.178 mmol) was added and the mixture was stirred for 1 h. The reaction mixture was diluted with EtOAc and washed with H$_2$O (3×5 mL). The organic layer was dried over MgSO$_4$ and concentrated in vacuo. The residue was purified by silica gel column chromatography using DCM/MeOH (98:2) to afford compounds 43-48.

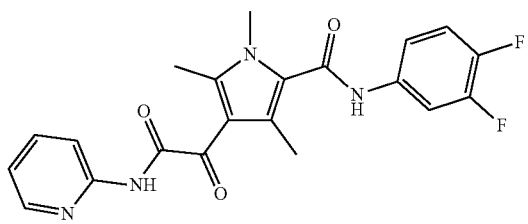 [SMILES: Cc1c(C(=O)C(=O)Nc2ccccn2)c(C)n(C)c1C(=O)Nc1ccc(F)c(F)c1]

N-(3,4-difluorophenyl)-1,3,5-trimethyl-4-(2-oxo-2-(pyridin-2-ylamino)acetyl)-1H-pyrrole-2-carboxamide (43)

Yield: 69%. $^1$H NMR (400 MHz, Chloroform-d) δ 9.33 (s, 1H), 8.45-8.38 (m, 1H), 8.30 (d, J=8.3 Hz, 1H), 7.85-7.67 (m, 2H), 7.49 (s, 1H), 7.22-7.12 (m, 3H), 3.75 (s, 3H), 2.45 (s, 3H), 2.44 (s, 3H). HRMS (ESI): m/z [M+H]$^+$ calcd for C$_{21}$H$_{19}$F$_2$N$_4$O$_3$: 413.1425, found: 413.1416.

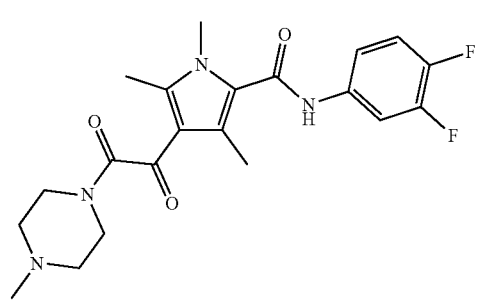 [SMILES: Cc1c(C(=O)C(=O)N2CCN(C)CC2)c(C)n(C)c1C(=O)Nc1ccc(F)c(F)c1]

N-(3,4-difluorophenyl)-1,3,5-trimethyl-4-(2-(4-methylpiperazin-1-yl)-2-oxoacetyl)-1H-pyrrole-2-carboxamide (44)

Yield: 74%. $^1$H NMR (400 MHz, Chloroform-d) δ 8.98 (s, 1H), 7.80-7.69 (m, 1H), 7.43-7.32 (m, 1H), 7.13 (dt, J=10.0, 8.8 Hz, 1H), 3.72-3.67 (m, 2H), 3.66 (s, 3H), 3.32 (dd, J=5.9, 4.1 Hz, 2H), 2.46 (t, J=5.2 Hz, 2H), 2.42 (s, 3H), 2.35 (t, J=5.1 Hz, 2H), 2.31 (s, 3H), 2.30 (s, 3H). HRMS (ESI): m/z [M+H]$^+$ calcd for C$_{21}$H$_{25}$F$_2$N$_4$O$_3$: 419.1895, found: 419.1886.

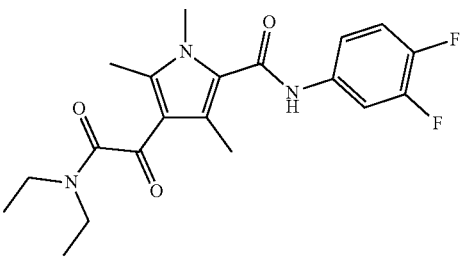 [SMILES: CCN(CC)C(=O)C(=O)c1c(C)c(C(=O)Nc2ccc(F)c(F)c2)n(C)c1C]

4-(2-(diethylamino)-2-oxoacetyl)-N-(3,4-difluorophenyl)-1,3,5-trimethyl-1H-pyrrole-2-carboxamide (45)

Yield: 71%. $^1$H NMR (400 MHz, Chloroform-d) δ 9.07 (s, 1H), 7.87-7.73 (m, 1H), 7.45-7.36 (m, 1H), 7.13 (dt, J=10.0, 8.8 Hz, 1H), 3.66 (s, 3H), 3.48 (q, J=7.1 Hz, 2H), 3.22 (q, J=7.0 Hz, 2H), 2.42 (s, 3H), 2.31 (s, 3H), 1.21 (t, J=7.1 Hz, 3H), 1.14 (t, J=7.0 Hz, 3H). HRMS (ESI): m/z [M+H]$^+$ calcd for C$_{20}$H$_{24}$F$_2$N$_3$O$_3$: 392.1786, found: 392.1776.

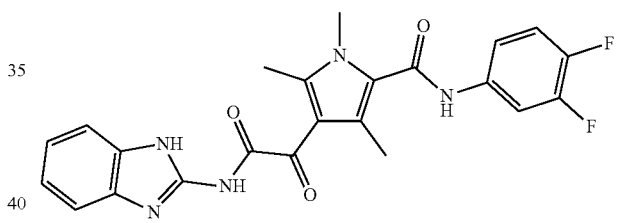

4-(2-((1H-benzo[d]imidazol-2-yl)amino)-2-oxoacetyl)-N-(3,4-difluorophenyl)-1,3,5-trimethyl-1H-pyrrole-2-carboxamide (46)

Yield: 46%. $^1$H NMR (400 MHz, DMSO-d$_6$) δ 12.42 (s, 2H), 10.45 (s, 1H), 8.03-7.76 (m, 1H), 7.56-7.38 (m, 4H), 7.18 (dd, J=5.9, 3.2 Hz, 2H), 3.61 (s, 3H), 2.45 (s, 3H), 2.27 (s, 3H). HRMS (ESI): m/z [M+H]$^+$ calcd for C$_{23}$H$_2$F$_2$NO$_3$: 452.1534, found: 452.1525.

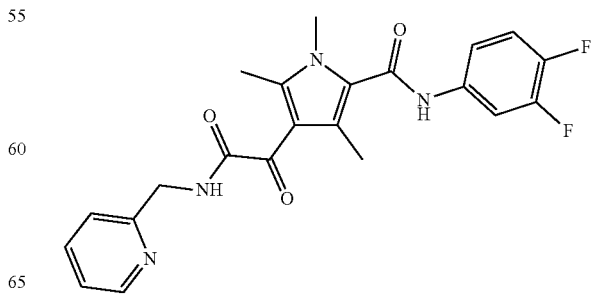

N-(3,4-difluorophenyl)-1,3,5-trimethyl-4-(2-oxo-2-((pyridin-2-ylmethyl)amino)acetyl)-1H-pyrrole-2-carboxamide (47)

Yield: 55%. ¹H NMR (400 MHz, DMSO-d₆) δ 10.42 (s, 1H), 9.28 (t, J=6.1 Hz, 1H), 8.53 (d, J=4.8 Hz, 1H), 7.94-7.77 (m, 2H), 7.46-7.41 (m, 2H), 7.38 (d, J=8.0 Hz, 1H), 7.34-7.26 (m, 1H), 4.50 (d, J=5.9 Hz, 2H), 3.59 (s, 3H), 2.38 (s, 3H), 2.21 (s, 3H). HRMS (ESI): m/z [M+H]⁺ calcd for $C_{22}H_2F_2N_4O_3$: 427.1582, found: 427.1572.

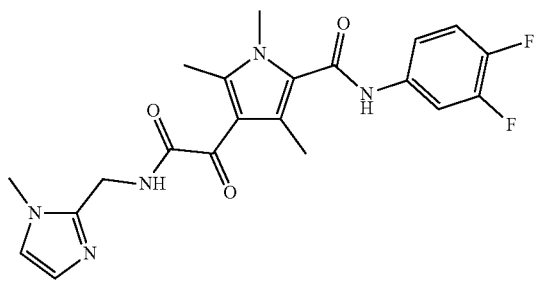 [SMILES: Cc1c(C(=O)C(=O)NCc2nccn2C)c(C)n(C)c1C(=O)Nc1ccc(F)c(F)c1]

N-(3,4-difluorophenyl)-1,3,5-trimethyl-4-(2-(((1-methyl-1H-imidazol-2-yl)methyl)amino)-2-oxoacetyl)-1H-pyrrole-2-carboxamide (48)

Yield: 63%. ¹H NMR (400 MHz, Chloroform-d) δ 8.48 (s, 2H), 7.77-7.66 (m, 1H), 7.26-7.20 (m, 1H), 7.13 (dt, J=9.9, 8.7 Hz, 1H), 6.93 (d, J=1.3 Hz, 1H), 6.85 (d, J=1.3 Hz, 1H), 4.53 (d, J=5.7 Hz, 2H), 3.72 (s, 3H), 3.64 (s, 3H), 2.30 (s, 3H), 2.24 (s, 3H). HRMS (ESI): m/z [M+H]⁺ calcd for $C_{21}H_{22}F_2N_5O_3$: 430.1691, found: 430.1681.

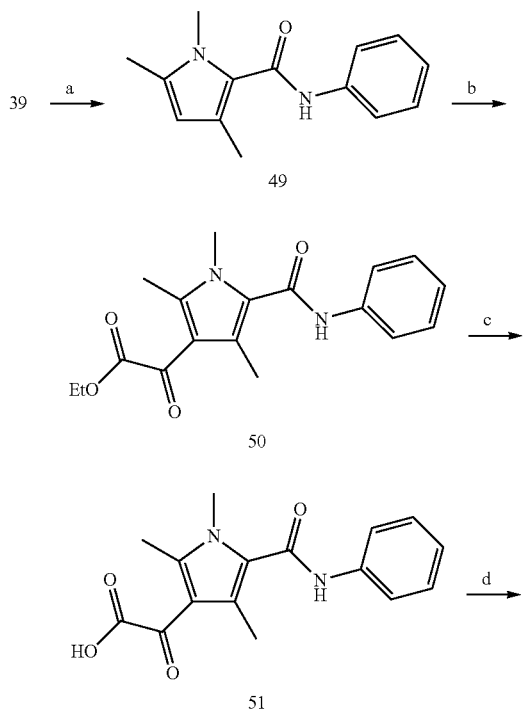

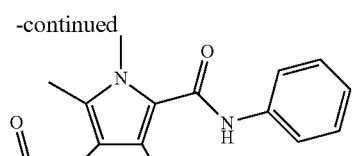

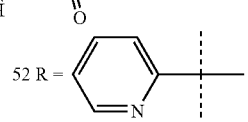

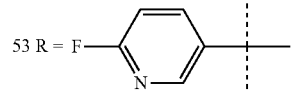

a) aniline, HATU, DIPEA, DMF, 60° C., 16 h; b) ethyl oxalyl chloride, AlCl₃, DCM, 0° C. to rt, 16 h; c) NaOH, EtOH, rt, 1 h; d) amine, HATU, DIPEA, DMF, rt, 2 h.

1,3,5-trimethyl-N-phenyl-1H-pyrrole-2-carboxamide (49)

To a solution of 39 (2.0 g, 13 mmol) in DMF (50 mL) were added aniline (2.4 mL, 26 mmol), HATU (5.93 g, 15.6 mmol) and DIPEA (4.5 mL, 26 mmol) at 0° C. The mixture was heated at 60° C. for 2 days. The reaction mixture was then diluted with EtOAc and washed with 1M HCl, water and brine. The organic layers was dried over MgSO₄ and concentrated in vacuo. The residue was purified by silica gel column chromatography using hexanes/EtOAc (8:2) to afford 49 in 58% yield (1.72 g). ¹H NMR (400 MHz, DMSO-d₆) δ 9.60 (s, 1H), 7.68 (d, J=8.0 Hz, 2H), 7.31 (t, J=7.7 Hz, 2H), 7.04 (t, J=7.4 Hz, 1H), 5.73 (s, 1H), 3.57 (s, 3H), 2.17 (s, 6H). MS (ESI): m/z [M+H]⁺ calcd for $C_{14}H_{17}N_2O$: 229.1, found: 229.5.

2-oxo-2-(1,2,4-trimethyl-5-(phenylcarbamoyl)-1H-pyrrol-3-yl)acetic acid (51)

To a solution of 49 (695 mg, 3.05 mmol) in DCM (30 mL) were added ethyl oxalylchloride (916 μL, 8.23 mmol) and AlCl₃ (1.01 g, 7.62 mmol) at 0° C. The mixture was stirred at room temperature for 16 h and poured into crushed ice. The mixture was extracted with DCM and combined organic layers were filtered on Celite. The filtrate was concentrated and the resulting residue was used in the next step without further purification. To a solution of crude 50 in EtOH was added NaOH 10% (30 mL). The mixture was stirred for 1 h at room temperature. EtOH was evaporated under vacuum and the mixture was washed with EtOAc (3×10 mL). The aqueous layer was acidified with 1M HCl. The mixture was extracted with EtOAc (3×10 mL). Combined organic layers were dried over MgSO₄ and concentrated in vacuo. The resulting solid was washed with Et₂O to afford 51 in 70% yield (642 mg) over two steps. ¹H NMR (400 MHz, DMSO-d₆) δ 14.18 (s, 1H), 10.26 (s, 1H), 7.71 (d, J=8.0 Hz, 2H), 7.35 (t, J=7.8 Hz, 2H), 7.10 (td, J=7.4, 1.1 Hz, 1H), 3.61 (s, 3H), 2.46 (s, 3H), 2.26 (s, 3H). MS (ESI): m/z [M+H]⁺ calcd for $C_{16}H_{17}N_2O_4$: 301.1, found: 301.5.

General Procedure for the Synthesis of Compounds 52 and 53

To a solution of 51 (50 mg, 0.17 mmol) in DMF (2 mL) were added amine (0.25 mmol), HATU (76 mg, 0.20 mmol) and DIPEA (58 μL, 0.33 mmol) at 0° C. The mixture was stirred at room temperature for 2 h. The solution was then diluted with EtOAc and washed with water and brine. The organic layers was dried over MgSO$_4$ and concentrated in vacuo. The residue was purified by silica gel column chromatography using DCM/MeOH (98:2) to afford to afford the desired compounds 52 and 53.

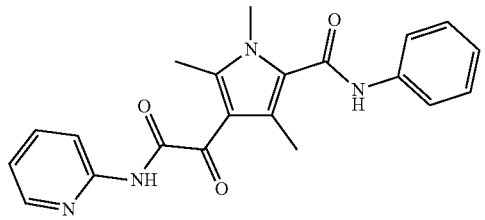 [SMILES: Cc1c(C(=O)C(=O)Nc2ccccn2)c(C)n(C)c1C(=O)Nc1ccccc1]

1,3,5-trimethyl-4-(2-oxo-2-(pyridin-2-ylamino) acetyl)-N-phenyl-1H-pyrrole-2-carboxamide (52)

Yield: 75%. $^1$H NMR (400 MHz, Chloroform-d) δ 9.47 (s, 1H), 8.43-8.35 (m, 1H), 8.30 (d, J=8.3 Hz, 1H), 7.86-7.74 (m, 1H), 7.68-7.57 (m, 3H), 7.46-7.34 (m, 1H), 7.22-7.10 (m, 2H), 3.73 (s, 3H), 2.44 (s, 3H), 2.43 (s, 3H). MS (ESI): m/z [M+H]$^+$ calcd for C$_{21}$H$_{21}$N$_4$O$_3$: 377.2, found: 377.4.

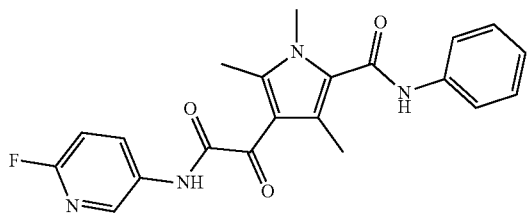 [SMILES: Cc1c(C(=O)C(=O)Nc2ccc(F)nc2)c(C)n(C)c1C(=O)Nc1ccccc1]

4-(2-((5-fluoropyridin-2-yl)amino)-2-oxoacetyl)-1,3,5-trimethyl-N-phenyl-1H-pyrrole-2-carboxamide (53)

Yield: 68%. $^1$H NMR (400 MHz, DMSO-d$_6$) δ 11.16 (s, 1H), 10.26 (s, 1H), 8.61-8.47 (m, 1H), 8.40-8.19 (m, 1H), 7.76-7.66 (m, 2H), 7.34 (dd, J=8.5, 7.4 Hz, 2H), 7.25 (dd, J=8.8, 3.2 Hz, 1H), 7.15-7.04 (m, 1H), 3.62 (s, 3H), 2.44 (s, 3H), 2.26 (s, 3H). MS (ESI): m/z [M+H]$^+$ calcd for C$_{21}$H$_{20}$FN$_4$O$_3$: 395.2, found: 395.5.

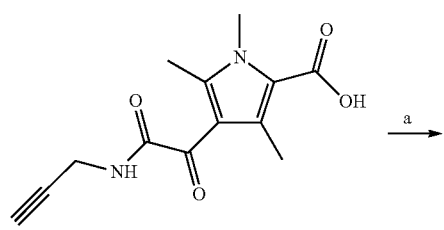

6 a →

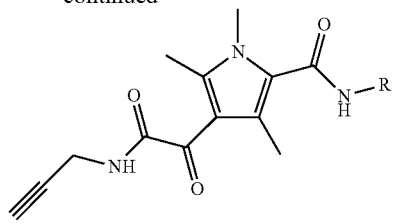

54-66

Reagents and conditions: a) amine, HATU, DIPEA, DMF, 16 h, rt; or i) SOCl$_2$, toluene, 110° C., 1 h, ii) amine, DMA, 0° C., 2 h.

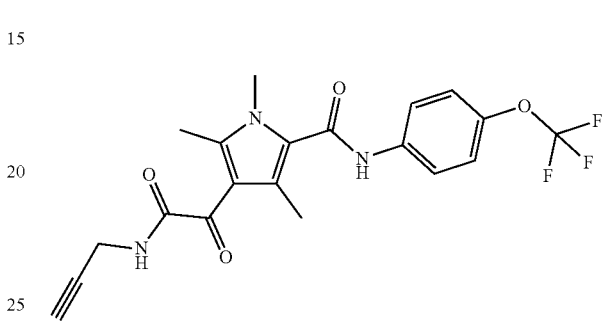

1,3,5-trimethyl-4-(2-oxo-2-(prop-2-yn-1-ylamino) acetyl)-N-(4-(trifluoromethoxy)phenyl)-1H-pyrrole-2-carboxamide (54)

To a solution of 4-[2-(propargylamino)-2-oxo-acetyl]-1,3,5-trimethyl-pyrrol-2-carboxylic acid 6 (250 mg, 1.0 mmol), 4-(trifluoromethoxy)aniline (227 mg, 1.3 mmol) and DIPEA (330 μL, 2.0 mmol) in pyridine (10 mL) was added HATU (0.65 g, 1.8 mmol) at room temperature. The mixture was stirred at 65° C. for 18 h. The reaction mixture was then poured into a saturated solution of ammonium chloride and extracted with ethyl acetate (3×50 mL). The combined organic layers were dried over sodium sulfate and concentrated in vacuo. The residue was purified by flash chromatography (Hexanes:EtOAc=6:4 v/v) to give compound 54 as a white powder (35%, 141 mg, 0.3 mmol). $^1$H NMR (400 MHz, Acetone-d$_6$) δ 9.51 (s, 1H), 8.17 (s, 1H), 7.95 (d, J=9.1 Hz, 2H), 7.36 (d, J=8.1 Hz, 2H), 4.17 (dd, J=5.9, 2.6 Hz, 2H), 3.70 (s, 3H), 2.75 (t, J=2.5 Hz, 1H), 2.45 (s, 3H), 2.31 (s, 3H). MS (ESI): m/z [M+H]$^+$ calcd for C$_{20}$H$_{19}$F$_3$N$_3$O$_4$: 422.4, found: 422.4.

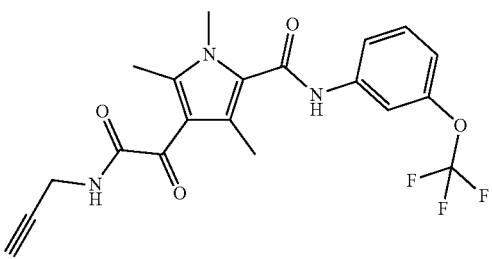 [SMILES: C#CCNC(=O)C(=O)c1c(C)c(C(=O)Nc2cccc(OC(F)(F)F)c2)n(C)c1C]

1,3,5-trimethyl-4-(2-oxo-2-(prop-2-yn-1-ylamino) acetyl)-N-(3-(trifluoromethoxy)phenyl)-1H-pyrrole-2-carboxamide (55)

To a solution of 4-[2-(propargylamino)-2-oxo-acetyl]-1,3,5-trimethyl-pyrrol-2-carboxylic acid 6 (250 mg, 1.0 mmol), 3-(trifluoromethoxy)aniline (227 mg, 1.3 mmol) and DIPEA (330 μL, 2.0 mmol) in pyridine (10 mL) was added HATU (0.65 g, 1.8 mmol) at room temperature. The mixture was stirred at 65° C. for 18 h. The reaction mixture was then poured into a saturated solution of ammonium chloride and extracted with ethyl acetate (3×50 mL). The combined organic layers were dried over sodium sulfate and concentrated in vacuo. The residue was purified by flash chromatography (Hexanes:EtOAc=6:4 v/v) to give compound 55 as a white powder (34%, 135 mg, 0.3 mmol). $^1$H NMR (400 MHz, Acetone-d$_6$) δ 9.57 (s, 1H), 8.18 (s, 1H), 8.02 (s, 1H), 7.81-7.67 (m, 1H), 7.50 (t, J=8.2 Hz, 1H), 7.16-7.06 (m, 1H), 4.17 (dd, J=5.8, 2.6 Hz, 2H), 3.71 (s, 3H), 2.75 (t, J=2.5 Hz, 1H), 2.45 (s, 3H), 2.32 (s, 3H). MS (ESI): m/z [M+H]$^+$ calcd for C$_{20}$H$_{19}$F$_3$N$_3$O$_4$: 422.4, found: 422.4.

1-(3,4-difluorophenyl)cyclopropanamine (50 mg, 0.3 mmol) and DIPEA (100 μL, 0.6 mmol) in DMF (5 mL) was added HATU (0.163 g, 0.4 mmol) at room temperature. The mixture was stirred at 65° C. for 18 h. The reaction mixture was then poured into a saturated solution of ammonium chloride and extracted with ethyl acetate (3×50 mL). The combined organic layers were dried over sodium sulfate and concentrated in vacuo. The residue was purified by flash chromatography (Hexanes:EtOAc=6:4 v/v) to give compound 57 (46%, 55 mg, 0.1 mmol). $^1$H NMR (400 MHz, Acetone-d$_6$) δ 8.11 (s, 1H), 8.06 (s, 1H), 7.35-7.28 (m, 1H), 7.27-7.17 (m, 2H), 4.13 (dd, J=5.8, 2.5 Hz, 2H), 3.60 (s, 3H), 2.72 (t, J=2.6 Hz, 1H), 2.38 (s, 3H), 2.23 (s, 3H), 1.41-1.30 (m, 4H). MS (ESI): m/z [M+H]$^+$ calcd for C$_{22}$H$_{22}$F$_2$N$_3$O$_3$: 414.4, found: 414.5.

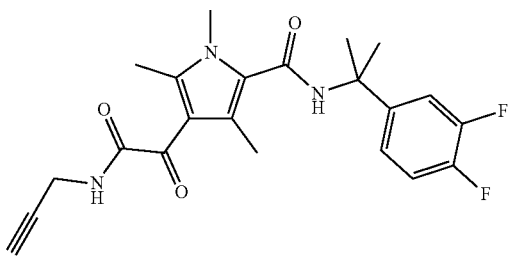 [SMILES: C#CCNC(=O)C(=O)c1c(C)c(C(=O)NC(C)(C)c2ccc(F)c(F)c2)n(C)c1C]

N-(2-(3,4-difluorophenyl)propan-2-yl)-1,3,5-trimethyl-4-(2-oxo-2-(prop-2-yn-1-ylamino)acetyl)-1H-pyrrole-2-carboxamide (56)

To a solution of 4-[2-(propargylamino)-2-oxo-acetyl]-1,3,5-trimethyl-pyrrol-2-carboxylic acid 6 (100 mg, 0.4 mmol), 2-(3,4-difluorophenyl)propan-2-amine (65 mg, 0.4 mmol) and DIPEA (132 μL, 0.8 mmol) in DMF (5 mL) was added HATU (0.218 g, 0.6 mmol) at room temperature. The mixture was stirred at 65° C. for 18 h. The reaction mixture was then poured into a saturated solution of ammonium chloride and extracted with ethyl acetate (3×50 mL). The combined organic layers were dried over sodium sulfate and concentrated in vacuo. The residue was purified by flash chromatography (Hexanes:EtOAc=6:4 v/v) to give compound 56 (38%, 61 mg, 0.1 mmol). $^1$H NMR (400 MHz, Acetone-d$_6$) δ 8.11 (s, 1H), 7.59 (s, 1H), 7.47-7.38 (m, 1H), 7.37-7.31 (m, 1H), 7.26 (dt, J=10.5, 8.5 Hz, 1H), 4.14 (dd, J=5.8, 2.5 Hz, 2H), 3.53 (s, 3H), 2.72 (t, J=2.6 Hz, 1H), 2.37 (s, 3H), 2.30 (s, 3H), 1.77 (s, 6H). MS (ESI): m/z [M+H]$^+$ calcd for C$_{22}$H$_{24}$F$_2$N$_3$O$_3$: 416.4, found: 416.5.

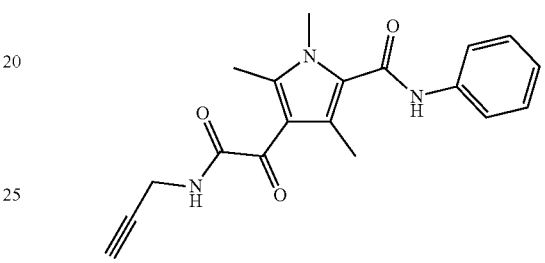

1,3,5-trimethyl-4-(2-oxo-2-(prop-2-yn-1-ylamino)acetyl)-N-phenyl-1H-pyrrole-2-carboxamide (58)

To a solution of 4-[2-(propargylamino)-2-oxo-acetyl]-1,3,5-trimethyl-pyrrol-2-carboxylic acid 6 (100 mg, 0.4 mmol), aniline (53 mg, 0.6 mmol) and DIPEA (100 μL, 0.6 mmol) in DMF (5 mL) was added HATU (0.163 g, 0.4 mmol) at room temperature. The mixture was stirred at 65° C. for 18 h. The reaction mixture was then poured into a saturated solution of ammonium chloride and extracted with ethyl acetate (3×50 mL). The combined organic layers were dried over sodium sulfate and concentrated in vacuo. The residue was purified by flash chromatography (DCM: MeOH=98:2 v/v) to give compound 58 as a yellowish powder (66%, 82 mg, 0.2 mmol). $^1$H NMR (400 MHz, Acetone-d$_6$) δ 9.32 (s, 1H), 8.18 (s, 1H), 7.88-7.79 (m, 2H), 7.44-7.32 (m, 1H), 7.20-7.08 (m, 1H), 4.16 (dd, J=5.9, 2.5 Hz, 2H), 3.69 (s, 3H), 2.75 (t, J=2.5 Hz, 1H), 2.44 (s, 3H), 2.31 (s, 3H). MS (ESI): m/z [M+H]$^+$ calcd for C$_{19}$H$_{20}$N$_3$O$_3$: 338.4, found: 338.5.

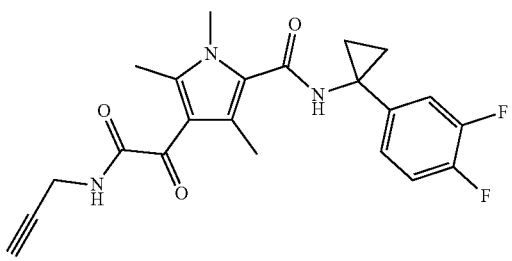 [SMILES: C#CCNC(=O)C(=O)c1c(C)c(C(=O)NC2(c3ccc(F)c(F)c3)CC2)n(C)c1C]

N-(1-(3,4-difluorophenyl)cyclopropyl)-1,3,5-trimethyl-4-(2-oxo-2-(prop-2-yn-1-ylamino)acetyl)-1H-pyrrole-2-carboxamide (57)

To a solution of 4-[2-(propargylamino)-2-oxo-acetyl]-1,3,5-trimethyl-pyrrol-2-carboxylic acid 6 (75 mg, 0.3 mmol),

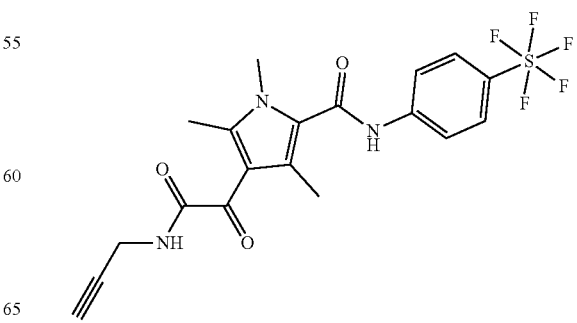

1,3,5-trimethyl-4-(2-oxo-2-prop-2-yn-1-ylamino)acetyl)-N-(4-(pentafluorosulfanyl)phenyl)-1H-pyrrole-2-carboxamide (59)

A solution of 4-[2-(propargylamino)-2-oxo-acetyl]-1,3,5-trimethyl-pyrrol-2-carboxylic acid 6 (100 mg, 0.4 mmol) and thionyl chloride (210 µL, 2.7 mmol) in toluene (5 mL) was heated to reflux for 1 h. The resulting solution was concentrated in vacuo, solubilized in N,N-dimethylacetamide (5 mL), and added to a solution of 4-pentafluorosulfanylaniline (167 mg, 0.8 mmol) in N,N-dimethylacetamide (5 mL) at 0° C. The mixture was stirred at 0° C. for 2 h, poured into a solution of hydrochloric acid 1N (50 mL), and extracted with ethyl acetate (3×50 mL). The combined organic layers were dried over sodium sulfate and concentrated in vacuo. The residue was purified by flash chromatography (Hexanes:EtOAc=6:4 v/v) to give compound 59 as a white powder (47%, 83 mg, 0.2 mmol). $^1$H NMR (400 MHz, Acetone-$d_6$) δ 9.72 (s, 1H), 8.19 (s, 1H), 8.03 (d, J=8.8 Hz, 2H), 7.88 (d, J=9.3 Hz, 2H), 4.16 (dd, J=5.9, 2.6 Hz, 2H), 3.71 (s, 3H), 2.75 (t, J=2.5 Hz, 1H), 2.45 (s, 3H), 2.32 (s, 3H). MS (ESI): m/z [M+H]$^+$ calcd for $C_{20}H_{19}F_3N_3O_4$: 464.4, found: 464.4.

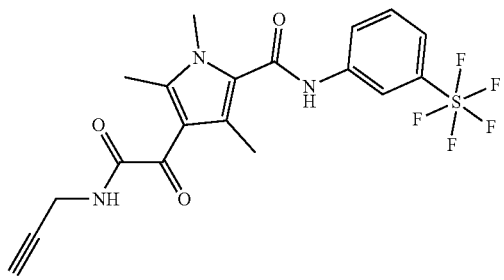 [SMILES: C#CCNC(=O)C(=O)c1c(C)c(C(=O)Nc2cccc(S(F)(F)(F)(F)F)c2)n(C)c1C]

1,3,5-trimethyl-4-(2-oxo-2-(prop-2-yn-1-ylamino)acetyl)-N-(3-(pentafluorosulfanyl)phenyl)-1H-pyrrole-2-carboxamide (60)

A solution of 4-[2-(propargylamino)-2-oxo-acetyl]-1,3,5-trimethyl-pyrrol-2-carboxylic acid 6 (100 mg, 0.4 mmol) and thionyl chloride (210 µL, 2.7 mmol) in toluene (5 mL) was heated to reflux for 1 h. The resulting solution was concentrated in vacuo, solubilized in N,N-dimethylacetamide (5 mL), and added to a solution of 3-pentafluorosulfanylaniline (167 mg, 0.8 mmol) in N,N-dimethylacetamide (5 mL) at 0° C. The mixture was stirred at 0° C. for 2 h, poured into a solution of hydrochloric acid 1N (50 mL), and extracted with ethyl acetate (3×50 mL). The combined organic layers were dried over sodium sulfate and concentrated in vacuo. The residue was purified by flash chromatography (Hexanes:EtOAc=6:4 v/v) to give compound 60 as a white powder (40%, 71 mg, 0.1 mmol). $^1$H NMR (400 MHz, Acetone-$d_6$) δ 9.68 (s, 1H), 8.54 (s, 1H), 8.20 (s, 1H), 8.00 (m, 1H), 7.63 (m, 1H), 4.16 (dd, J=5.9, 2.6 Hz, 2H), 3.71 (s, 3H), 2.75 (t, J=2.5 Hz, 1H), 2.45 (s, 3H), 2.33 (s, 3H). MS (ESI): m/z [M+H]$^+$ calcd for $C_{19}H_{19}F_5N_3O_3S$: 464.4, found: 464.4.

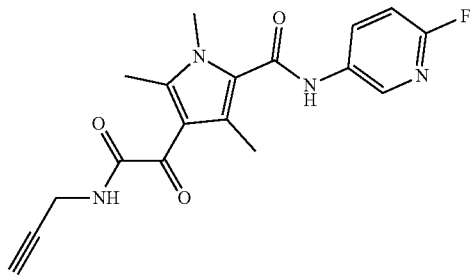 [SMILES: C#CCNC(=O)C(=O)c1c(C)c(C(=O)Nc2ccc(F)nc2)n(C)c1C]

N-(6-fluoropyridin-3-yl)-1,3,5-trimethyl-4-(2-oxo-2-(prop-2-yn-1-ylamino)acetyl)-1H-pyrrole-2-carboxamide (61)

A solution of 4-[2-(propargylamino)-2-oxo-acetyl]-1,3,5-trimethyl-pyrrol-2-carboxylic acid 6 (100 mg, 0.4 mmol) and thionyl chloride (210 µL, 2.7 mmol) in toluene (5 mL) was heated to reflux for 1 h. The resulting solution was concentrated in vacuo, solubilized in N,N-dimethylacetamide (5 mL), and added to a solution of 6-fluoropyridin-3-amine (85 mg, 0.8 mmol) in N,N-dimethylacetamide (5 mL) at 0° C. The mixture was stirred at 0° C. for 2 h, poured into a saturated solution of ammonium chloride (50 mL), and extracted with ethyl acetate (3×50 mL). The combined organic layers were dried over sodium sulfate and concentrated in vacuo. The residue was purified by flash chromatography (Hexanes:EtOAc=6:4 v/v) to give compound 61 as a white powder (68%, 92 mg, 0.2 mmol). $^1$H NMR (400 MHz, Acetone-$d_6$) δ 9.56 (s, 1H), 8.62 (s, 1H), 8.47-8.36 (m, 1H), 8.18 (s, 1H), 7.14 (dd, J=8.9, 3.4 Hz, 1H), 4.24-4.15 (m, 2H), 3.72 (s, 3H), 2.78-2.74 (m, 1H), 2.46 (s, 3H), 2.34 (s, 3H). MS (ESI): m/z [M+H]$^+$ calcd for $C_{18}H_{18}FN_4O_3$: 357.4, found: 357.4.

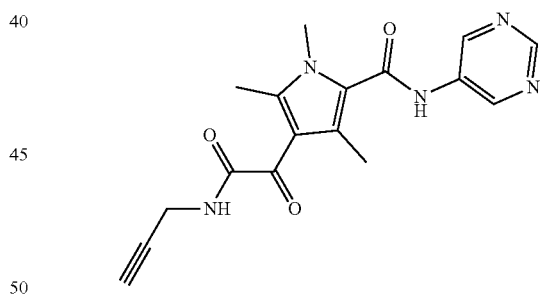

1,3,5-trimethyl-4-(2-oxo-2-(prop-2-yn-1-ylamino)acetyl)-N-(pyrimidin-5-yl)-1H-pyrrole-2-carboxamide (62)

A solution of 4-[2-(propargylamino)-2-oxo-acetyl]-1,3,5-trimethyl-pyrrol-2-carboxylic acid 6 (100 mg, 0.4 mmol) and thionyl chloride (210 µL, 2.7 mmol) in toluene (5 mL) was heated to reflux for 1 h. The resulting solution was concentrated in vacuo, solubilized in N,N-dimethylacetamide (5 mL), and added to a solution of pyrimidin-5-amine (73 mg, 0.8 mmol) in N,N-dimethylacetamide (5 mL) at 0° C. The mixture was stirred at 0° C. for 2 h, poured into a saturated solution of ammonium chloride (50 mL), and extracted with ethyl acetate (3×50 mL). The combined organic layers were dried over sodium sulfate and concentrated in vacuo. The residue was purified by flash chromatography (Hexanes:EtOAc=6:4 v/v) to give compound 62 as a white powder (31%, 40 mg, 0.1 mmol). $^1$H NMR (400 MHz, Acetone-d$_6$) δ 9.61 (s, 1H), 9.21 (s, 2H), 8.93 (s, 1H), 8.19 (s, 1H), 4.19 (dd, J=5.8, 2.6 Hz, 2H), 3.75 (s, 3H), 2.77 (t, J=2.6 Hz, 1H), 2.47 (s, 3H), 2.37 (s, 3H). MS (ESI): m/z [M+H]$^+$ calcd for C$_{17}$H$_{18}$N$_5$O$_3$: 340.4, found: 340.5.

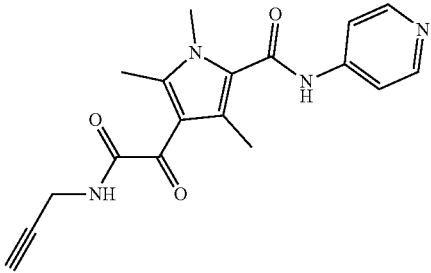 [SMILES: C#CCNC(=O)C(=O)c1c(C)c(C(=O)Nc2ccncc2)n(C)c1C]

1,3,5-trimethyl-4-(2-oxo-2-(prop-2-yn-1-ylamino)acetyl)-N-(pyridin-4-yl)-1H-pyrrole-2-carboxamide (63)

A solution of 4-[2-(propargylamino)-2-oxo-acetyl]-1,3,5-trimethyl-pyrrol-2-carboxylic acid 6 (100 mg, 0.4 mmol) and thionyl chloride (210 μL, 2.7 mmol) in toluene (5 mL) was heated to reflux for 1 h. The resulting solution was concentrated in vacuo, solubilized in N,N-dimethylacetamide (5 mL), and added to a solution of 4-aminopyridine (53 mg, 0.6 mmol) in N,N-dimethylacetamide (5 mL) at 0° C. The mixture was stirred at 0° C. for 2 h, poured into a saturated solution of ammonium chloride (50 mL), and extracted with ethyl acetate (3×50 mL). The combined organic layers were dried over sodium sulfate and concentrated in vacuo. The residue was purified by flash chromatography (DCM:MeOH=98:2 v/v) to give compound 63 (71%, 92 mg, 0.3 mmol). $^1$H NMR (400 MHz, Acetone-d$_6$) δ 9.60 (s, 1H), 8.49 (d, J=6.5 Hz, 2H), 8.19 (s, 1H), 7.75 (d, J=6.5 Hz, 2H), 4.15 (dd, J=5.7, 2.5 Hz, 2H), 3.70 (s, 3H), 2.74 (t, J=2.6 Hz, 1H), 2.44 (s, 3H), 2.30 (s, 3H). MS (ESI): m/z [M+H]$^+$ calcd for C$_{18}$H$_{19}$N$_4$O$_3$: 339.4, found: 339.5.

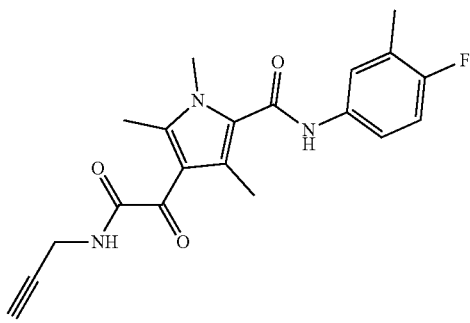 [SMILES: C#CCNC(=O)C(=O)c1c(C)c(C(=O)Nc2ccc(F)c(C)c2)n(C)c1C]

N-(4-fluoro-3-methylphenyl)-1,3,5-trimethyl-4-(2-oxo-2-(prop-2-yn-1-ylamino)acetyl)-1H-pyrrole-2-carboxamide (64)

A solution of 4-[2-(propargylamino)-2-oxo-acetyl]-1,3,5-trimethyl-pyrrol-2-carboxylic acid 6 (100 mg, 0.4 mmol) and thionyl chloride (210 μL, 2.7 mmol) in toluene (5 mL) was refluxed for 1 h. The resulting solution was concentrated in vacuo, solubilized in N,N-dimethylacetamide (5 mL), and added to a solution of 4-fluoro-3-methylaniline (71 mg, 0.6 mmol) in N,N-dimethylacetamide (5 mL) at 0° C. The mixture was stirred at 0° C. for 2 h, poured into a saturated solution of ammonium chloride (50 mL), and extracted with ethyl acetate (3×50 mL). The combined organic layers were dried over sodium sulfate and concentrated in vacuo. The residue was purified by flash chromatography (Hexanes:EtOAc=6:4 v/v) to give compound 64 as a white solid (67%, 95 mg, 0.2 mmol). $^1$H NMR (400 MHz, Acetone-d$_6$) δ 9.25 (s, 1H), 8.14 (s, 1H), 7.72 (dd, J=6.9, 2.5 Hz, 1H), 7.68-7.59 (m, 1H), 7.05 (t, J=9.2 Hz, 1H), 4.15 (dd, J=5.9, 2.6 Hz, 2H), 3.68 (s, 3H), 2.73 (t, J=2.6 Hz, 1H), 2.42 (s, 3H), 2.28 (s, 3H), 2.27 (d, J=2.0 Hz, 3H). MS (ESI): m/z [M+H]$^+$ calcd for C$_{20}$H$_2$FN$_3$O$_3$: 370.4, found: 370.5.

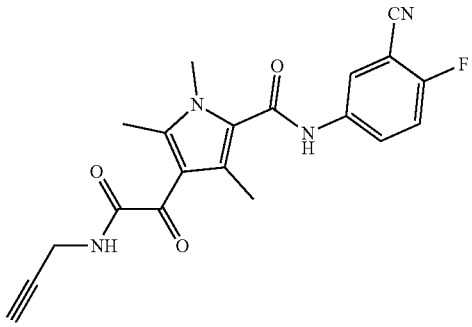 [SMILES: C#CCNC(=O)C(=O)c1c(C)c(C(=O)Nc2ccc(F)c(C#N)c2)n(C)c1C]

N-(3-cyano-4-fluorophenyl)-1,3,5-trimethyl-4-(2-oxo-2-(prop-2-yn-1-ylamino)acetyl)-1H-pyrrole-2-carboxamide (65)

A solution of 4-[2-(propargylamino)-2-oxo-acetyl]-1,3,5-trimethyl-pyrrol-2-carboxylic acid 6 (100 mg, 0.4 mmol) and thionyl chloride (210 μL, 2.7 mmol) in toluene (5 mL) was refluxed for 1 h. The resulting solution was concentrated in vacuo, solubilized in N,N-dimethylacetamide (5 mL), and added to a solution of 5-amino-2-fluorobenzonitrile (78 mg, 0.6 mmol) in N,N-dimethylacetamide (5 mL) at 0° C. The mixture was stirred at 0° C. for 2 h, poured into a saturated solution of ammonium chloride (50 mL), and extracted with ethyl acetate (3×50 mL). The combined organic layers were dried over sodium sulfate and concentrated in vacuo. The residue was purified by flash chromatography (Hexanes:EtOAc=6:4 v/v) to give compound 65 as a white solid (42%, 61 mg, 0.2 mmol). $^1$H NMR (400 MHz, Acetone-d$_6$) δ 9.61 (s, 1H), 8.32 (dd, J=5.7, 2.7 Hz, 1H), 8.16 (s, 1H), 8.13-8.07 (m, 1H), 7.46 (t, J=9.1 Hz, 1H), 4.15 (dd, J=5.8, 2.5 Hz, 2H), 3.70 (s, 3H), 2.74 (t, J=2.5 Hz, 1H), 2.44 (s, 3H), 2.30 (s, 3H). MS (ESI): m/z [M+H]$^+$ calcd for C$_{20}$H$_{18}$FN$_4$O$_3$: 381.4, found: 381.3.

93

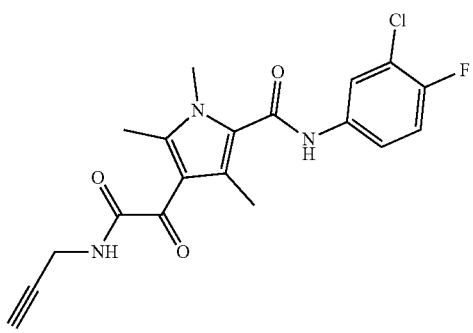 [SMILES: C#CCNC(=O)C(=O)c1c(C)c(C(=O)Nc2ccc(F)c(Cl)c2)n(C)c1C]

N-(3-chloro-4-fluorophenyl)-1,3,5-trimethyl-4-(2-oxo-2-(prop-2-yn-1-ylamino)acetyl)-1H-pyrrole-2-carboxamide (66)

A solution of 4-[2-(propargylamino)-2-oxo-acetyl]-1,3,5-trimethyl-pyrrol-2-carboxylic acid 6 (100 mg, 0.4 mmol) and thionyl chloride (210 μL, 2.7 mmol) in toluene (5 mL) was refluxed for 1 h. The resulting solution was concentrated in vacuo, solubilized in N,N-dimethylacetamide (5 mL), and added to a solution of 3-chloro-4-fluoroaniline (83 mg, 0.6 mmol) in N,N-dimethylacetamide (5 mL) at 0° C. The mixture was stirred at 0° C. for 2 h, poured into a saturated solution of ammonium chloride (50 mL), and extracted with ethyl acetate (3×50 mL). The combined organic layers were dried over sodium sulfate and concentrated in vacuo. The residue was purified by flash chromatography (Hexanes:EtOAc=6:4 v/v) to give compound 66 as a white solid (20%, 30 mg, 0.1 mmol). $^1$H NMR (400 MHz, Acetone-d$_6$) δ 9.45 (s, 1H), 8.29-8.03 (m, 2H), 7.84-7.64 (m, 1H), 7.32 (t, J=9.0 Hz, 1H), 4.15 (dd, J=5.9, 2.6 Hz, 2H), 3.69 (s, 3H), 2.73 (s, 1H), 2.43 (s, 3H), 2.29 (s, 3H). MS (ESI): m/z [M+H]$^+$ calcd for C$_{19}$H$_{18}$FN$_3$O$_3$: 390.8, found: 390.4.

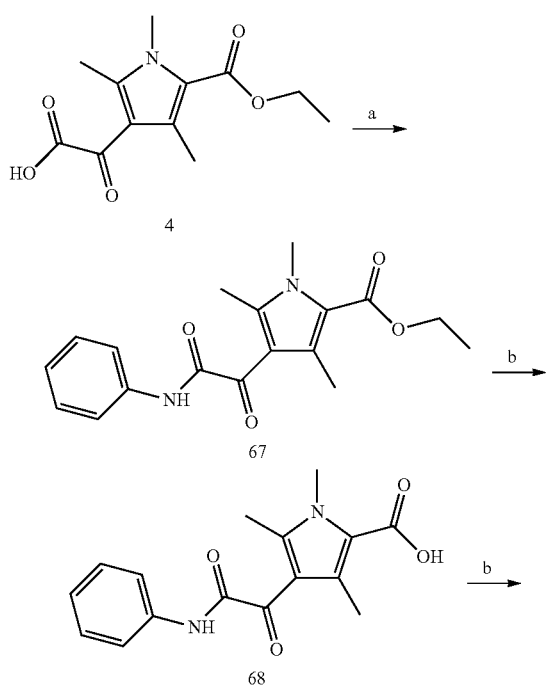

94

-continued

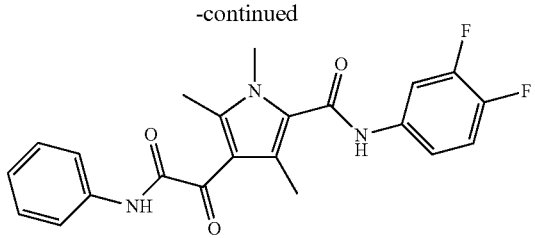

Reagents and conditions: a) CDI, aniline, DMF, 3 h, rt; b) NaOH 5%, MeOH, 16 h, rt; c) 3,4-difluoroaniline, HATU, DIPEA, DMF, 16 h, rt.

1,3,5-trimethyl-4-(2-oxo-2-(phenylamino)acetyl)-1H-pyrrole-2-carboxylic acid (68)

To a solution of 2-(5-ethoxycarbonyl-1,3,5-trimethyl-pyrrol-3-yl)-2-oxo-acetic acid 4 (2.5 g, 9.9 mmol) in DMF (15 mL) and CH$_2$Cl$_2$ (10 mL) was added 1,1'-carbonyldiimidazole (2.4 g, 11.8 mmol) and aniline (1.35 mL, 9.5 mmol). After stirring for 2 h at room temperature, the reaction mixture was poured onto a saturated solution of ammonium chloride and extracted with CH$_2$Cl$_2$ (3×100 mL). The combined organic layers were dried over sodium sulfate and concentrated in vacuo to give 67 as a white solid. To the crude ethyl 1,3,5-trimethyl-4-(2-oxo-2-(phenylamino)acetyl)-1H-pyrrole-2-carboxylate 67 dissolved in methanol (10 mL) and THF (10 mL) was added a 5% solution of sodium hydroxide (10 mL). The reaction mixture was stirred at room temperature overnight and after evaporation of the methanol and THF in vacuo, the aqueous solution was washed with ethyl acetate (2×50 mL), acidified with a 1N HCl solution (pH=1) and extracted again with ethyl acetate (3×50 mL). The combined organic layers were dried over sodium sulfate and concentrated in vacuo. The resulting solid was washed with diethyl ether (50 mL) and hexanes (50 mL) to yield 1,3,5-trimethyl-4-(2-oxo-2-(phenylamino)acetyl)-1H-pyrrole-2-carboxylic acid 68 (1.8 g, 6.0 mmol, 62%). $^1$H NMR (400 MHz, DMSO-d$_6$) δ 10.79 (s, 1H), 7.75-7.67 (m, 2H), 7.37 (t, J=7.9 Hz, 2H), 7.20-7.11 (m, 1H), 3.77 (s, 3H), 2.41 (s, 6H). MS (ESI): m/z [M+H]$^+$ calcd for C$_{16}$H$_{17}$N$_2$O$_4$: 301.3, found: 301.4.

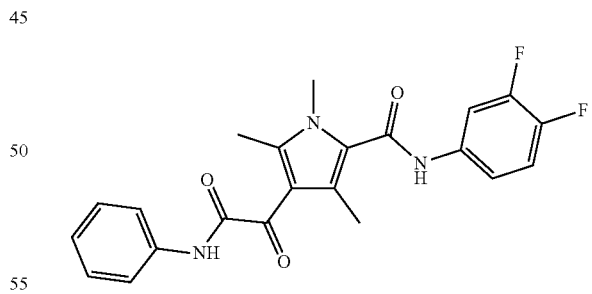

N-(3,4-difluorophenyl)-1,3,5-trimethyl-4-(2-oxo-2-(phenylamino)acetyl)-1H-pyrrole-2-carboxamide (69)

To a solution of 1,3,5-trimethyl-4-(2-oxo-2-(phenylamino)acetyl)-1H-pyrrole-2-carboxylic acid 68 (200 mg, 0.7 mmol), 3,4-difluoroaniline (129 mg, 1.0 mmol) and DIPEA (231 μL, 4.3 mmol) in DMF (5 mL) was added HATU (304 mg, 0.8 mmol) at room temperature. The mixture was stirred at 50° C. for 3 h. In order to reach completion, more 3,4-difluoroaniline (65 mg, 0.5 mmol) was added and the mixture was further stirred overnight at 65° C. The reaction mixture was then poured into a saturated solution of ammonium chloride and extracted with ethyl acetate (3×50 mL). The combined organic layers were dried over sodium sulfate and concentrated in vacuo. The residue was purified by flash chromatography (Hexanes:EtOAc=6:4 v/v) to give compound 69 as a white powder (35%, 110 mg, 0.3 mmol). $^1$H NMR (400 MHz, Acetone-$d_6$) δ 9.73 (s, 1H), 9.52 (s, 1H), 8.02-7.94 (m, 1H), 7.87-7.80 (m, 2H), 7.56-7.48 (m, 1H), 7.43-7.36 (m, 2H), 7.32 (dt, J=10.6, 9.0 Hz, 1H), 7.20-7.13 (m, 1H), 3.70 (s, 3H), 2.46 (s, 3H), 2.31 (s, 3H). MS (ESI): m/z [M+H]$^+$ calcd for $C_{22}H_{20}F_2N_3O_3$: 412.4, found: 412.5.

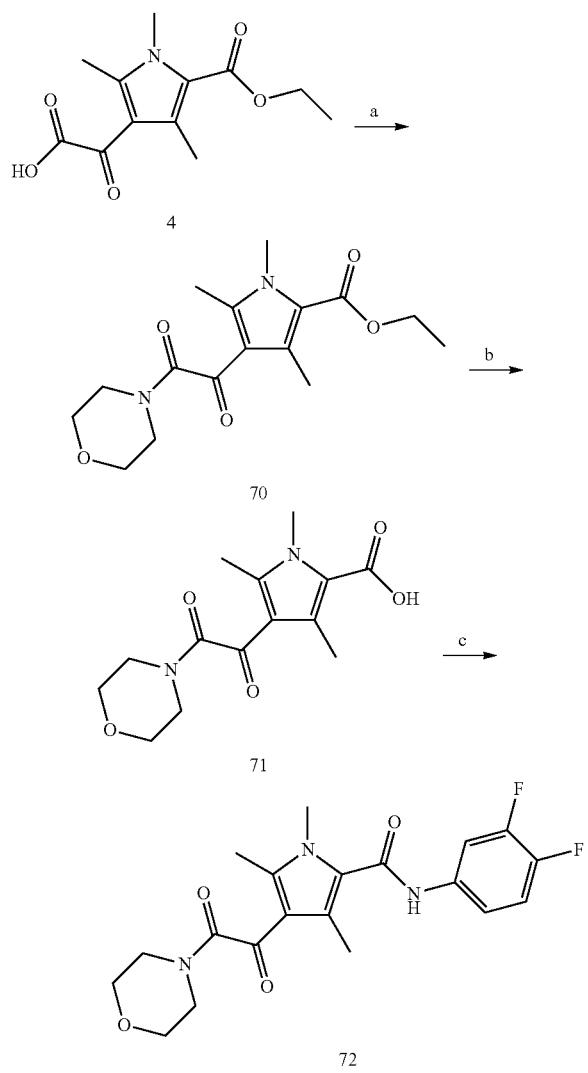

Reagents and conditions: a) CDI, morpholine, DMF, 3 h, rt; b) NaOH 5%, MeOH, 16 h, rt; d) 3,4-difluoroaniline, HATU, DIPEA, DMF, 16 h, rt.

1,3,5-trimethyl-4-(2-morpholino-2-oxoacetyl)-1H-pyrrole-2-carboxylic acid (71)

To a solution of 2-(5-ethoxycarbonyl-1,3,5-trimethyl-pyrrol-3-yl)-2-oxo-acetic acid 4 (0.5 g, 2.0 mmol) in DMF (15 mL) and $CH_2Cl_2$ (10 mL) was added 1,1′-carbonyldiimidazole (0.53 g, 3.2 mmol) and morpholine (0.25 mL, 3.2 mmol). After stirring for 2 h at room temperature, the reaction mixture was poured onto a saturated solution of ammonium chloride and extracted with $CH_2Cl_2$ (3×100 mL). The combined organic layers were dried over sodium sulfate and concentrated in vacuo to give 70 as a yellowish oil. To the crude ethyl 1,3,5-trimethyl-4-(2-morpholino-2-oxoacetyl)-1H-pyrrole-2-carboxylate 70 dissolved in methanol (10 mL) and THF (10 mL) was added a 5% solution of sodium hydroxide (10 m). The reaction mixture was stirred at room temperature overnight and after evaporation of the methanol and THF in vacuo, the aqueous solution was washed with ethyl acetate (2×50 mL), acidified with a 1N HCl solution (pH=1) and extracted again with ethyl acetate (3×50 mL). The combined organic layers were dried over sodium sulfate and concentrated in vacuo. The resulting solid was washed with diethyl ether (50 mL) and hexanes (50 mL) to yield 1,3,5-trimethyl-4-(2-morpholino-2-oxoacetyl)-1H-pyrrole-2-carboxylic acid 71 (0.41 g, 1.3 mmol, 70%). $^1$H NMR (400 MHz, DMSO-$d_6$) δ 12.86 (s, 1H), 3.75 (s, 3H), 3.71-3.63 (m, 2H), 3.59-3.51 (m, 4H), 3.33-3.25 (m, 2H), 2.44 (s, 3H), 2.42 (s, 3H). MS (ESI): m/z [M+H]$^+$ calcd for $C_{14}H_{19}N_2O_5$: 295.3, found: 295.4.

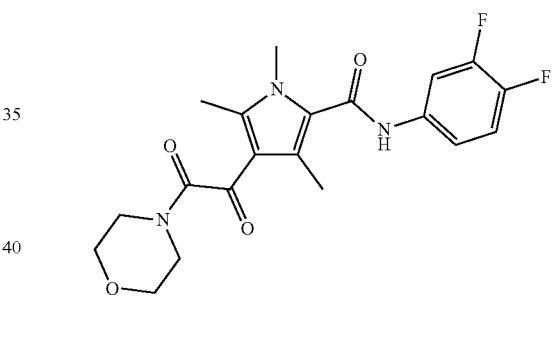

N-(3,4-difluorophenyl)-1,3,5-trimethyl-4-(2-morpholino-2-oxoacetyl)-1H-pyrrole-2-carboxamide (72)

A solution of 1,3,5-trimethyl-4-(2-morpholino-2-oxoacetyl)-1H-pyrrole-2-carboxylic acid 71 (100 mg, 0.3 mmol) and thionyl chloride (210 μL, 2.7 mmol) in toluene (5 mL) was heated to reflux for 1 h. The resulting solution was concentrated in vacuo, solubilized in N,N-dimethylacetamide (5 mL), and added to a solution of 3,4-difluoroaniline (66 mg, 0.5 mmol) in N,N-dimethylacetamide (5 mL) at 0° C. The mixture was stirred at 0° C. for 2 h, poured into a saturated solution of ammonium chloride (50 mL), and extracted with ethyl acetate (3×50 mL). The combined organic layers were dried over sodium sulfate and concentrated in vacuo. The residue was purified by flash chromatography (DCM:MeOH=98:2 v/v) to give compound 72 as a brownish solid (29%, 40 mg, 0.1 mmol). $^1$H NMR (400 MHz, Acetone-$d_6$) δ 9.53 (s, 1H), 8.03-7.93 (m, 1H), 7.58-7.44 (m, 1H), 7.33 (dt, J=10.6, 9.0 Hz, 1H), 3.74-3.67 (m, 6H), 3.66-3.61 (m, 3H), 3.39 (t, J=4.8 Hz, 2H), 2.51 (s, 3H), 2.33 (s, 3H). MS (ESI): m/z [M+H]$^+$ calcd for $C_{20}H_{22}F_2N_3O_4$: 406.4, found: 406.5.

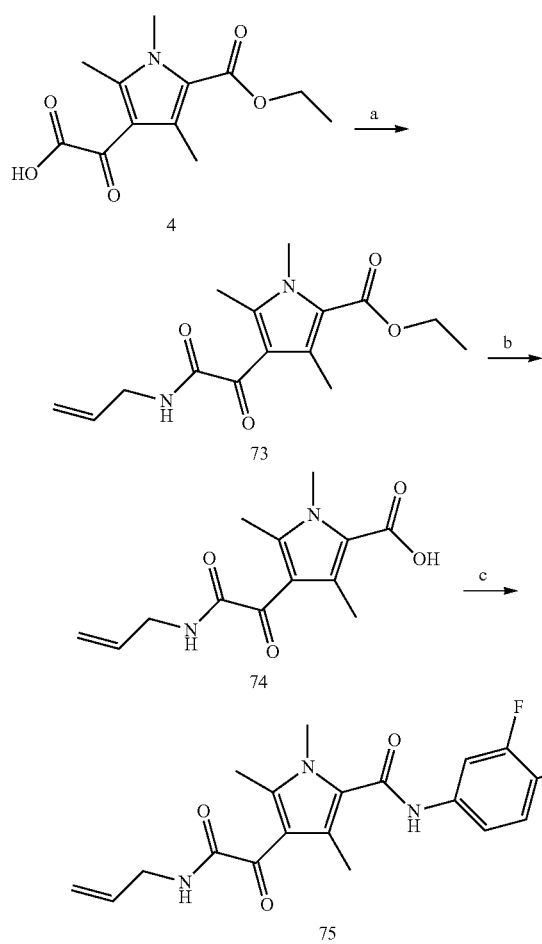

Reagents and conditions: a) CDI, allylamine, DMF, 3 h, RT; b) NaOH 5%, MeOH, 16 h, rt;

4-(2-(allylamino)-2-oxoacetyl)-1,3,5-trimethyl-1H-pyrrole-2-carboxylic acid (74)

To a solution of 2-(5-ethoxycarbonyl-1,3,5-trimethyl-pyrrol-3-yl)-2-oxo-acetic acid 4 (0.5 g, 2.0 mmol) in DMF (15 mL) and $CH_2Cl_2$ (10 mL) was added 1,1'-carbonyldiimidazole (0.53 g, 3.2 mmol) and allylamine (0.18, 3.2 mmol). After stirring for 2 h at room temperature, the reaction mixture was poured onto a saturated solution of ammonium chloride and extracted with $CH_2Cl_2$ (3×100 mL). The combined organic layers were dried over sodium sulfate and concentrated in vacuo to give 73 as a white solid. To the crude ethyl 4-(2-(allylamino)-2-oxoacetyl)-1,3,5-trimethyl-1H-pyrrole-2-carboxylate 73 dissolved in methanol (10 mL) and THF (10 mL) was added a 5% solution of sodium hydroxide (10 m). The reaction mixture was stirred at room temperature overnight and after evaporation of the methanol and THF in vacuo, the aqueous solution was washed with ethyl acetate (2×50 mL), acidified with a 1N HCl solution (pH=1) and extracted again with ethyl acetate (3×50 mL). The combined organic layers were dried over sodium sulfate and concentrated in vacuo. The resulting solid was washed with diethyl ether (50 mL) and hexanes (50 mL) to yield 4-(2-(allylamino)-2-oxoacetyl)-1,3,5-trimethyl-1H-pyrrole-2-carboxylic acid 74 (270 mg, 1.0 mmol, 51%). $^1$H NMR (400 MHz, DMSO-$d_6$) δ 12.74 (s, 1H), 8.86 (t, J=5.8 Hz, 1H), 5.99-5.66 (m, 1H), 5.36-5.05 (m, 2H), 3.85-3.80 (m, 2H), 3.75 (s, 3H), 2.36 (s, 6H). MS (ESI): m/z [M+H]$^+$ calcd for $C_{13}H_{17}N_2O_4$: 265.3, found: 265.4.

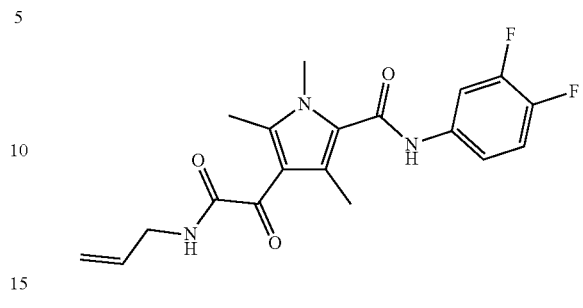

4-(2-(allylamino)-2-oxoacetyl)-N-(3,4-difluorophenyl)-1,3,5-trimethyl-1H-pyrrole-2-carboxamide (75)

A solution of 4-(2-(allylamino)-2-oxoacetyl)-1,3,5-trimethyl-1H-pyrrole-2-carboxylic acid 74 (100 mg, 0.4 mmol) and thionyl chloride (210 µL, 2.7 mmol) in toluene (5 mL) was refluxed for 1 h. The resulting solution was concentrated in vacuo, solubilized in N,N-dimethylacetamide (5 mL), and added to a solution of 3,4-difluoroaniline (73 mg, 0.6 mmol) in N,N-dimethylacetamide (5 mL) at 0° C. The mixture was stirred at 0° C. for 2 h, poured into a saturated solution of ammonium chloride (50 mL), and extracted with ethyl acetate (3×50 mL). The combined organic layers were dried over sodium sulfate and concentrated in vacuo. The residue was purified by flash chromatography (Hexanes:EtOAc=6:4 v/v) to give compound 75 as a white solid (18%, 25 mg, 0.1 mmol). $^1$H NMR (400 MHz, Acetone-$d_6$) δ 9.48 (s, 1H), 8.09-7.94 (m, 1H), 7.89 (s, 1H), 7.59-7.48 (m, 1H), 7.32 (dt, J=10.2, 9.0 Hz, 1H), 6.02-5.86 (m, 1H), 5.28 (dd, J=17.2, 1.6 Hz, 1H), 5.12 (dd, J=10.2, 1.4 Hz, 1H), 3.99-3.94 (m, 2H), 3.68 (s, 3H), 2.42 (s, 3H), 2.28 (s, 3H). MS (ESI): m/z [M+H]$^+$ calcd for $C_{19}H_{20}F_2N_3O_3$: 376.4, found: 376.4.

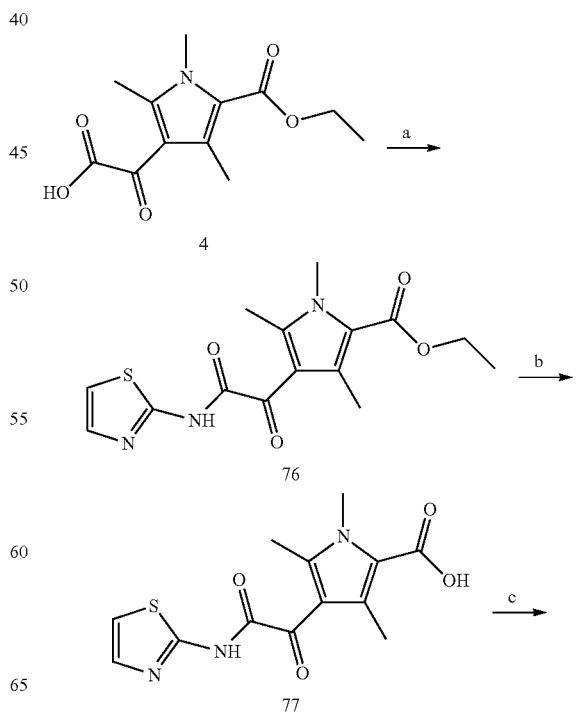

-continued

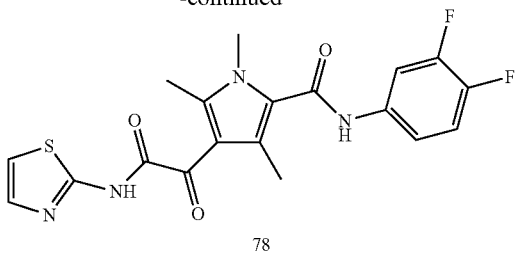

78

Reagents and conditions: a) CDI, 2-aminothiazole, DMF, 3 h, rt; b) NaOH 5%, MeOH, 16 h, rt; c) 3,4-difluoroaniline, HATU, DIPEA, DMF, 16 h, rt.

1,3,5-trimethyl-4-(2-oxo-2-(thiazol-2-ylamino)acetyl)-1H-pyrrole-2-carboxylic acid (77)

To a solution of 2-(5-ethoxycarbonyl-1,3,5-trimethyl-pyrrol-3-yl)-2-oxo-acetic acid 4 (2.0 g, 7.9 mmol) in DMF (15 mL) and CH$_2$Cl$_2$ (10 mL) was added 1,1'-carbonyldiimidazole (1.92 g, 11.8 mmol) and 2-aminothiazole (0.95 g, 9.5 mmol). After stirring for 2 h at room temperature, the reaction mixture was poured onto a saturated solution of ammonium chloride, filtered through fritted funnel, dried under vacuum to give 76 as a yellow solid. To the crude ethyl 1,3,5-trimethyl-4-(2-oxo-2-(thiazol-2-ylamino)acetyl)-1H-pyrrole-2-carboxylate 76 dissolved in methanol (10 mL) and THF (10 mL) was added a 5% solution of sodium hydroxide (10 mL). The reaction mixture was stirred at room temperature overnight and after evaporation of the methanol and THF in vacuo, the aqueous solution was washed with ethyl acetate (2×50 mL), acidified with a 1N HCl solution (pH=1) and extracted again with ethyl acetate (3×50 mL). The combined organic layers were dried over sodium sulfate and concentrated in vacuo. The resulting solid was washed with diethyl ether (50 mL) and hexanes (50 mL) to yield 1,3,5-trimethyl-4-(2-oxo-2-(thiazol-2-ylamino)acetyl)-1H-pyrrole-2-carboxylic acid 77 (1.9 g, 6.1 mmol, 78%) as a yellow solid. $^1$H NMR (400 MHz, DMSO-d$_6$) δ 12.96 (s, 1H), 7.58 (s, 1H), 7.38 (s, 1H), 3.77 (s, 3H), 2.37 (s, 3H), 2.33 (s, 3H). MS (ESI): m/z [M+H]$^+$ calcd for C$_{13}$H$_{14}$N$_3$O$_4$: 308.3, found: 308.4.

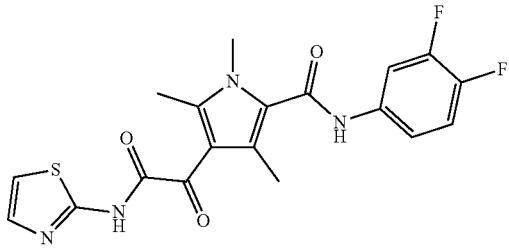 [SMILES: Cc1c(C(=O)C(=O)Nc2nccs2)c(C)n(C)c1C(=O)Nc1ccc(F)c(F)c1]

N-(3,4-difluorophenyl)-1,3,5-trimethyl-4-(2-oxo-2-(thiazol-2-ylamino)acetyl)-1H-pyrrole-2-carboxamide (78)

To a solution of 1,3,5-trimethyl-4-(2-oxo-2-(thiazol-2-ylamino)acetyl)-1H-pyrrole-2-carboxylic acid 77 (250 mg, 0.8 mmol), 3,4-difluoroaniline (158 mg, 1.2 mmol) and DIPEA (283 µL, 1.6 mmol) in DMF (15 mL) was added HATU (0.37 g, 1.0 mmol) at room temperature. The mixture was stirred at 50° C. for 3 h. In order to reach completion, more 3,4-difluoroaniline (80 mg, 0.6 mmol) was added and the mixture was further stirred overnight at 65° C. The reaction mixture was then poured into a saturated solution of ammonium chloride and extracted with ethyl acetate (3×50 mL). The combined organic layers were dried over sodium sulfate and concentrated in vacuo. The residue was purified by flash chromatography (DCM:MeOH=98:2 v/v) to give compound 78 as a yellowish powder (55%, 187 mg, 0.4 mmol). $^1$H NMR (400 MHz, DMSO-d$_6$) δ 13.01 (s, 1H), 10.47 (s, 1H), 7.88 (dd, J=13.3, 7.5 Hz, 1H), 7.58 (d, J=3.6 Hz, 1H), 7.54-7.35 (m, 3H), 3.62 (s, 3H), 2.41 (s, 3H), 2.19 (s, 3H). MS (ESI): m/z [M+H]$^+$ calcd for C$_{19}$H$_{18}$F$_2$N$_3$O$_3$: 419.4, found: 419.4.

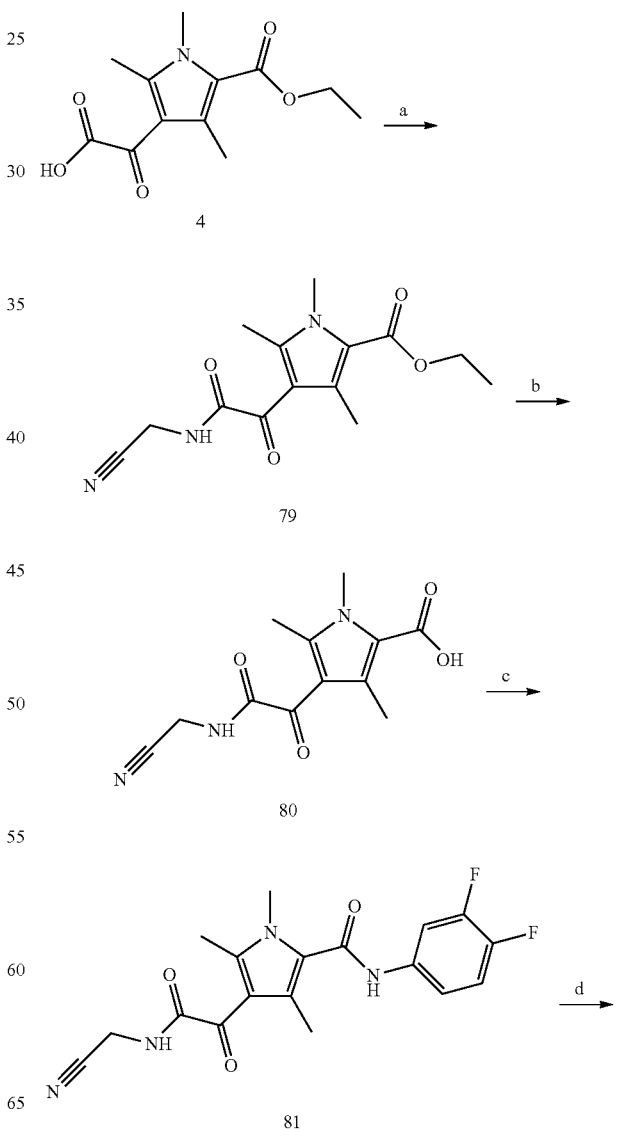

-continued

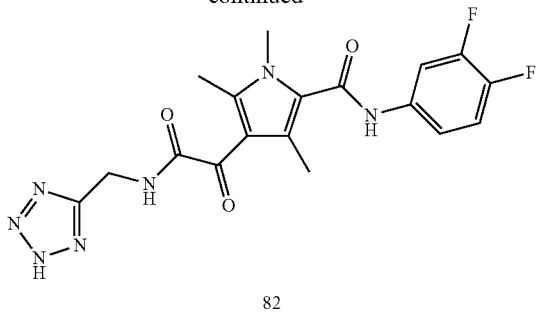

82

Reagents and conditions: a) CDI, aminoacetonitrile hydrochloride, Et₃N, DMF, 3 h, rt; b) NaOH 5%, MeOH, 16 h, rt; c) 3,4-difluoroaniline, HATU, DIPEA, DMF, 16 h, rt; d) NaN₃, ZnBr₂, iPrOH, 110° C. MW, 20 min.

4-(2-((cyanomethyl)amino)-2-oxoacetyl)-1,3,5-trimethyl-1H-pyrrole-2-carboxylic acid (80)

To a solution of 2-(5-ethoxycarbonyl-1,3,5-trimethyl-pyrrol-3-yl)-2-oxo-acetic acid 4 (3.0 g, 11.8 mmol) in DMF (20 mL) and CH₂Cl₂ (20 mL) was added 1,1'-carbonyldiimidazole (2.3 g, 14.2 mmol) and 2-aminoacetonitrile hydrochloride (1.63 g, 17.8 mmol) and diisopropylethylamine (4.12 mL, 23.7 mmol). After stirring for 2 h at room temperature, the reaction mixture was poured onto a saturated solution of ammonium chloride and extracted with CH₂Cl₂ (3×100 mL). The combined organic layers were dried over sodium sulfate and concentrated in vacuo to give 79 as a solid. To the crude ethyl 4-(2-((cyanomethyl)amino)-2-oxoacetyl)-1,3,5-trimethyl-1H-pyrrole-2-carboxylate 79 dissolved in methanol (10 mL) and THF (10 mL) was added a 5% solution of sodium hydroxide (10 m). The reaction mixture was stirred at room temperature overnight and after evaporation of the methanol and THF in vacuo, the aqueous solution was washed with ethyl acetate (2×50 mL), acidified with a 1N HCl solution (pH=1) and extracted again with ethyl acetate (3×50 mL). The combined organic layers were dried over sodium sulfate and concentrated in vacuo. The resulting solid was washed with diethyl ether (50 mL) and hexanes (50 mL) to yield 4-(2-((cyanomethyl)amino)-2-oxoacetyl)-1,3,5-trimethyl-1H-pyrrole-2-carboxylic acid 80 (0.41 g, 15.5 mmol, 13%). ¹H NMR (400 MHz, DMSO-d₆) δ 12.79 (s, 1H), 9.46 (s, 1H), 4.32 (d, J=5.7 Hz, 2H), 3.76 (s, 3H), 2.37 (s, 3H), 2.36 (s, 3H). MS (ESI): m/z [M+H]⁺ calcd for C₁₂H₁₄N₃O₄: 264.3, found: 264.4.

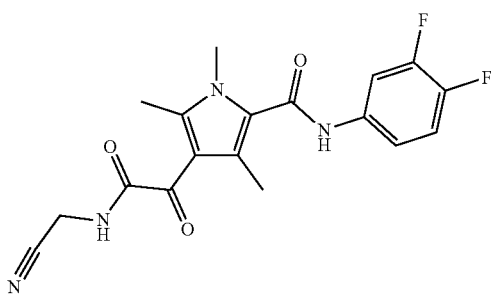 [SMILES: Cc1c(C(=O)C(=O)NCC#N)c(C)n(C)c1C(=O)Nc1ccc(F)c(F)c1]

4-(2-((cyanomethyl)amino)-2-oxoacetyl)-N-(3,4-difluorophenyl)-1,3,5-trimethyl-1H-pyrrole-2-carboxamide (81)

4-(2-((cyanomethyl)amino)-2-oxoacetyl)-1,3,5-trimethyl-1H-pyrrole-2-carboxylic acid 80 (2 g, 7.6 mmol), 3,4-difluoroaniline (1.47 g, 11.4 mmol) and DIPEA (1.98 mL, 11.4 mmol) in DMF (30 mL) was added HATU (3.18 g, 8.3 mmol) at room temperature. The mixture was stirred at 65° C. for 18 h. The reaction mixture was then poured into a saturated solution of ammonium chloride and extracted with ethyl acetate (3×150 mL). The combined organic layers were dried over sodium sulfate and concentrated in vacuo. The residue was purified by flash chromatography (Hexanes: EtOAc=6:4 v/v) to give compound 81 as a white powder (30%, 840 mg, 2.2 mmol). ¹H NMR (400 MHz, Acetone-d₆) δ 9.52 (s, 1H), 8.52 (s, 1H), 8.09-7.90 (m, 1H), 7.58-7.45 (m, 1H), 7.40-7.23 (m, 1H), 4.49-4.36 (m, 2H), 3.74-3.65 (m, 3H), 2.46-2.40 (m, 3H), 2.34-2.25 (m, 3H). MS (ESI): m/z [M+H]⁺ calcd for C₁₈H₁₇F₂N₄O₃: 375.3, found: 375.4.

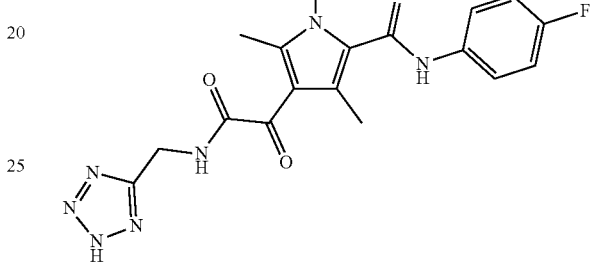

4-(2-(((2H-tetrazol-5-yl)methyl)amino)-2-oxoacetyl)-N-(3,4-difluorophenyl)-1,3,5-trimethyl-1H-pyrrole-2-carboxamide (82)

Sodium azide (26 mg, 0.4 mmol) and zinc bromide (90 mg, 0.4 mmol) were added to a suspension of 4-(2-((cyanomethyl)amino)-2-oxoacetyl)-N-(3,4-difluorophenyl)-1,3,5-trimethyl-1H-pyrrole-2-carboxamide 81 (50 mg, 0.1 mmol) in isopropanol (2 mL). The mixture was heated to 110° C. for 20 min under microwave irradiations. The reaction mixture was then poured onto a saturated solution of sodium carbonate (50 mL) and washed with ethyl acetate (3×20 mL). The aqueous phase was then acidified to pH~1 and extracted with ethyl acetate (3×50 mL). The combined organic phases were dried over sodium sulfate and concentrated in vacuo. The resulting residue was purified by flash chromatography (DCM/MeOH=95:5 v/v), resulting in compound 82 as a white powder (48%, 27 mg, 0.1 mmol). ¹H NMR (400 MHz, DMSO-d₆) δ 10.41 (s, 1H), 9.46 (t, J=5.8 Hz, 1H), 7.92-7.83 (m, 1H), 7.50-7.37 (m, 2H), 4.69 (d, J=5.7 Hz, 2H), 3.58 (s, 3H), 2.33 (s, 3H), 2.17 (s, 3H). LCMS (ESI): m/z [M+H]⁺ calcd for C₁₈H₁₈F₂N₇O₃: 418.4, found: 418.4.

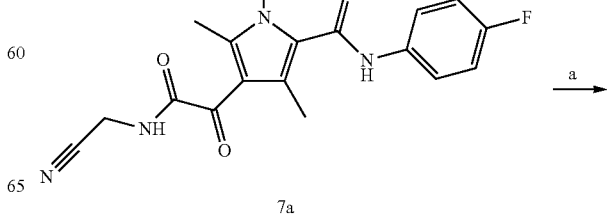

7a

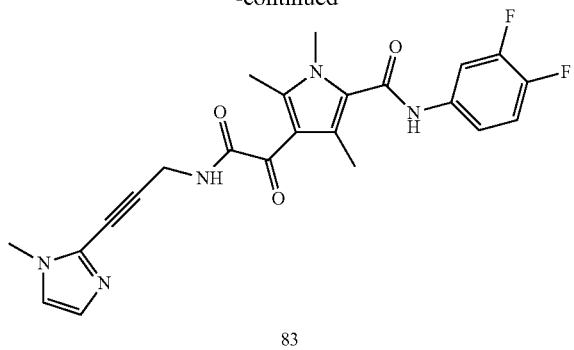

83

N-(3,4-difluorophenyl)-1,3,5-trimethyl-4-(2-((3-(1-methyl-1H-imidazol-2-yl)prop-2-yn-1-yl)amino)-2-oxoacetyl)-1H-pyrrole-2-carboxamide (83)

Compound 7a (100 mg, 268 μmol), 2-bromo-1-methyl-1H-imidazole (65 mg, 402 μmol), triethylamine (73 μL, 541 μmol), and dimethylformamide (2 mL) were combined in a sealed tube. The mixture was sparged for 2 minutes with nitrogen, and bis(triphenylphosphine) palladium dichloride (19 mg, 27 μmol) was added followed by copper iodide (10 mg, 53 μmol). The mixture was sparged again with nitrogen and stirred for 20 minutes at 70° C. under microwave irradiation. The reaction was diluted with ethyl acetate (50 mL), washed with a saturated solution of ammonium chloride (50 mL). The organic phase was dried over sodium sulfate and concentrated under reduced pressure and purified by flash chromatography on silica gel (DCM/MeOH: 96/4) to give compound 83 (62 mg, 137 μmol, 51%). $^1$H NMR (400 MHz, Acetone-$d_6$) δ 9.51 (s, 1H), 8.35 (s, 1H), 7.99 (ddd, J=13.2, 7.4, 2.6 Hz, 1H), 7.57-7.48 (m, 1H), 7.34 (dt, J=10.5, 9.0 Hz, 1H), 7.14 (d, J=1.2 Hz, 1H), 6.92 (d, J=1.2 Hz, 1H), 4.46 (d, J=5.8 Hz, 2H), 3.75 (s, 3H), 3.70 (s, 3H), 2.46 (s, 3H), 2.32 (s, 3H). $^{19}$F NMR (377 MHz, Acetone-$d_6$) δ −139.91−−140.01 (dt, J=22.1, 11.6 Hz), −147.12−−147.23 (dt, J=20.5, 10.4 Hz). MS (ESI): m/z [M+H]$^+$ calcd for $C_{23}H_{22}F_2N_5O_3$: 454.4, found: 454.4.

Example 2

Cellular Toxicity Assays

The toxicity of the compounds was assessed in Vero, human PBM, CEM (human lymphoblastoid), MT-2, and HepG2 cells, as described previously (see Schinazi R. F., Sommadossi J.-P., Saalmann V., Cannon D. L., Xie M.-Y., Hart G. C., Smith G. A. & Hahn E. F. Antimicrob. Agents Chemother. 1990, 34, 1061-67). Cycloheximide was included as positive cytotoxic control, and untreated cells exposed to solvent were included as negative controls. The cytotoxicity IC$_{50}$ was obtained from the concentration-response curve using the median effective method described previously (see Chou T.-C. & Talalay P. Adv. Enzyme Regul. 1984, 22, 27-55; Belen'kii M. S. & Schinazi R. F. Antiviral Res. 1994, 25, 1-11). The results are shown in Table 1 below:

TABLE 1

| Cytotoxicity, CC$_{50}$, μM (% inhibition) | | | | |
| --- | --- | --- | --- | --- |
| | Cytotoxicity; CC$_{50}$ (μM) | | | |
| Compound | PBM | CEM | VERO | HepG2 |
| 7a | >100 | >100 | >90 | |
| 17 | >100 | 53 | 41 | |
| 13 | 64.8 | 17.5 | 66.0 | |
| 8 | 60.5 | 45.4 | >100 | 98.6 |
| 36 | 13.9 | 36.7 | 22.9 | 43.5 |
| 13 | >100 | 78.3 | 55.6 | >100 |
| 20 | >100 | >100 | >100 | >100 |
| 31 | >100 | >100 | 41.9 | 93.9 |
| 27 | | 37.9 | 80.1 | >100 |
| 28 | | >100 | 13.4 | >100 |
| 29 | | >100 | 62.4 | >100 |
| 30 | | >100 | 91.4 | >100 |
| 25 | >100 | >100 | 68.1 | >100 |
| 26 | >100 | >100 | 31.2 | >100 |
| 32 | >100 | >100 | >100 | >100 |
| 7b | >100 | >100 | >100 | >100 |
| 38 | >100 | 29 | 45 | 85 |
| 43 | >100 | 50 | >100 | >100 |
| 44 | 92 | 17 | >100 | 90 |
| 45 | 90 | 36 | 47 | 75 |
| 46 | >100 | 38 | 10 | 7 |
| 47 | >100 | 47 | 51 | 35 |
| 48 | >100 | 27 | >100 | 84 |
| 52 (3057) | >100 | 50 | >100 | >100 |
| 54 | 3 | 4 | 6 | |
| 55 | >100 | 38 | 15 | 88 |
| 56 | >100 | >100 | >100 | >100 |
| 57 | >100 | >100 | >100 | >100 |
| 58 | >100 | >100 | >100 | >100 |
| 59 | 44 | 3 | 12 | 43 |
| 60 | 86 | 23 | 82 | >100 |
| 61 | >100 | >100 | >100 | >100 |
| 62 | >100 | >100 | >100 | >100 |
| 63 | >100 | >100 | >100 | >100 |
| 64 | >100 | 18 | 96 | >100 |
| 65 | >100 | >100 | >100 | >100 |
| 66 | >100 | 52 | 70 | 83 |
| 69 | >100 | >100 | 48 | 59 |
| 72 | 30 | 14 | 51 | 100 |
| 75 | >100 | 66 | 33 | >100 |
| 78 | >100 | 15 | >100 | 84 |
| 81 | 30 | 33 | >100 | 71 |
| 82 | >100 | >100 | >100 | >100 |
| 83 | 7 | 4 | 7 | 42 |

Example 3

Mitochondrial Toxicity Assays in HepG2 Cells i) Effect of Compounds on Cell Growth and Lactic Acid Production: The effect on the growth of HepG2 cells was determined by incubating cells in the presence of 0 μM, 0.1 μM, 1 μM, 10 μM and 100 μM drug. Cells (5×10$^4$ per well) were plated into 12-well cell culture clusters in minimum essential medium with nonessential amino acids supplemented with 10% fetal bovine serum, 1% sodium pyruvate, and 1% penicillin/streptomycin and incubated for 4 days at 37° C. At the end of the incubation period the cell number was determined using a hemocytometer. Also taught by Pan-Zhou X-R, Cui L, Zhou X-J, Sommadossi J-P, Darley-Usmer V M. "Differential effects of antiretroviral nucleoside analogs on mitochondrial function in HepG2 cells," Antimicrob. Agents Chemother. 2000; 44: 496-503.

To measure the effects of the compounds on lactic acid production, HepG2 cells from a stock culture were diluted and plated in 12-well culture plates at 2.5×10$^4$ cells per well. Various concentrations (0 μM, 0.1 μM, 1 μM, 10 μM and 100

μM) of compound were added, and the cultures were incubated at 37° C. in a humidified 5% $CO_2$ atmosphere for 4 days. At day 4, the number of cells in each well was determined and the culture medium collected. The culture medium was then filtered, and the lactic acid content in the medium was determined using a colorimetric lactic acid assay (Sigma-Aldrich). Since lactic acid product can be considered a marker for impaired mitochondrial function, elevated levels of lactic acid production detected in cells grown in the presence of test compounds would indicate a drug-induced cytotoxic effect.

ii) Effect on Compounds on Mitochondrial DNA Synthesis: a real-time PCR assay to accurately quantify mitochondrial DNA content has been developed (see Stuyver L J, Lostia S, Adams M, Mathew J S, Pai B S, Grier J, Tharnish P M, Choi Y, Chong Y, Choo H, Chu C K, Otto M J, Schinazi R F. Antiviral activities and cellular toxicities of modified 2',3'-dideoxy-2',3'-didehydrocytidine analogs. Antimicrob. Agents Chemother. 2002; 46: 3854-60). This assay was used in all studies described in this application that determine the effect of compounds on mitochondrial DNA content. In this assay, low-passage-number HepG2 cells were seeded at 5,000 cells/well in collagen-coated 96-well plates. Test compounds were added to the medium to obtain final concentrations of 0 μM. 0.1 μM, 10 μM and 100 μM. On culture day 7, cellular nucleic acids were prepared by using commercially available columns (RNeasy 96 kit; Qiagen). These kits co-purify RNA and DNA, and hence, total nucleic acids are eluted from the columns. The mitochondrial cytochrome c oxidase subunit II (COXII) gene and the ß-actin or rRNA gene were amplified from 5 μl of the eluted nucleic acids using a multiplex Q-PCR protocol with suitable primers and probes for both target and reference amplifications. For COXII the following sense, probe and antisense primers were used, respectively: 5'-TGCCCGCCATCATCCTA-3' (SEQ ID No: 1), 5'-tetrachloro-6-carboxyfluorescein-TCCTCATCGCCCTCC-CATCCC-TAMRA-3'(SEQ ID NO: 2) and 5'-CGTCTGT-TATGTAAAGGATGCGT-3' (SEQ ID NO: 3). For exon 3 of the ß-actin gene (GenBank accession number E01094) the sense, probe, and antisense primers are 5'-GCGCGGCTA-CAGCTTCA-3' (SEQ ID NO: 4), 5'-6-FAMCAC-CACGGCCGAGCGGGATAMRA-3' (SEQ ID NO: 5) and 5'-TCTCCTTAATGTCACGCACGAT-3'(SEQ ID NO: 6), respectively. The primers and probes for the rRNA gene are commercially available from Applied Biosystems.

Since equal amplification efficiencies are obtained for all genes, the comparative CT method was used to investigate potential inhibition of mitochondrial DNA synthesis. The comparative CT method uses arithmetic formulas in which the amount of target (COXII gene) is normalized to the amount of an endogenous reference (the ß-actin or rRNA gene) and is relative to a calibrator (a control with no drug at day 7). The arithmetic formula for this approach is given by 2-AACT, where AACT is (CT for average target test sample—CT for target control)—(CT for average reference test—CT for reference control) (see Johnson M R, K Wang, J B Smith, M J Heslin, R B Diasio. Quantitation of dihydropyrimidine dehydrogenase expression by real-time reverse transcription polymerase chain reaction. Anal. Biochem. 2000; 278:175-184). A decrease in mitochondrial DNA content in cells grown in the presence of drug indicated mitochondrial toxicity.

The effect of compounds 7 and 9 on the levels of mitochondrial and nuclear DNA, and lactic acid production was evaluated in HepG2 cells (14-day assay), and the data is tabulated below in Table 2:

TABLE 2

| Cmpd | μM | % inhibition MtDNA/nDNA | $IC_{50}$, μM MtDNA/ nDNA | MtDNA (% of control) | Lactic acid production (% of control) |
|---|---|---|---|---|---|
| 7a | 10 | <1/5.4 | >50/>50 | 110 (100-121) | 103 ± 32.0 |
|  | 25 | <1/<1 |  | 91.8 (80.2-105) | 106 ± 19.5 |
|  | 50 | 17.7/13.1 |  | 94.6 (73.8-121) | 193 ± 12.6 |
| ddC (control) | 10 | 97.4/52.4 | <10/<10 | 5.3 (5.0-5.8) | 196 ± 73.0 |
| 3TC (control) | 10 | 8.8/29.6 | >10/>10 | 130 (85.7-196) | 94 ± 20.8 |

The data show that compounds 7a, as described herein, is non-toxic up to 25 μM and very low toxicity was noted even at 50 μM, similar to the negative control 3TC.

Example 4

Mitochondrial Toxicity Assays in Neuro2A Cells

To estimate the potential of the compounds of this invention to cause neuronal toxicity, mouse Neuro2A cells (American Type Culture Collection 131) can be used as a model system (see Ray A S, Hernandez-Santiago B I, Mathew J S, Murakami E, Bozeman C, Xie M Y, Dutschman G E, Gullen E, Yang Z, Hurwitz S, Cheng Y C, Chu C K, McClure H, Schinazi R F, Anderson K S. Mechanism of anti-human immunodeficiency virus activity of beta-D-6-cyclopropylamino-2',3'-didehydro-2',3'-dideoxyguanosine. Antimicrob. Agents Chemother. 2005, 49, 1994-2001). The concentrations necessary to inhibit cell growth by 50% ($CC_{50}$) can be measured using the 3-(4,5-dimethyl-thiazol-2-yl)-2,5-diphenyltetrazolium bromide dye-based assay, as described. Perturbations in cellular lactic acid and mitochondrial DNA levels at defined concentrations of drug can be carried out as described above. ddC and AZT can be used as control nucleoside analogs.

Example 5

Assay for Bone Marrow Cytotoxicity

Primary human bone marrow mononuclear cells can be obtained commercially from Cambrex Bioscience (Walkersville, Md.). CFU-GM assays is carried out using a bilayer soft agar in the presence of 50 units/mL human recombinant granulocyte/macrophage colony-stimulating factor, while BFU-E assays used a ethylcellulose matrix containing 1 unit/mL erythropoietin (see Sommadossi J P, Carlisle R. Toxicity of 3'-azido-3'-deoxythymidine and 9-(1,3-dihydroxy-2-propoxymethyl) guanine for normal human hepatopoietic progenitor cells in vitro. Antimicrob. Agents Chemother. 1987; 31: 452-454; Sommadossi, J P, Schinazi, R F, Chu, C K, and Xie, M Y. Comparison of cytotoxicity of the (−) and (+) enantiomer of 2',3'-dideoxy-3'-thiacytidine in normal human bone marrow progenitor cells. Biochem. Pharmacol. 1992; 44:1921-1925). Each experiment can be performed in duplicate in cells from three different donors. AZT is used as a positive control. Cells can be incubated in the presence of the compound for 14-18 days at 37° C. with 5% $CO_2$, and colonies of greater than 50 cells can be counted using an inverted microscope to determine the $IC_{50}$. The 50% inhibitory concentration ($IC_{50}$) can be obtained by least-squares linear regression analysis of the logarithm of drug concentration versus BFU-E survival fractions. Statistical analysis can be performed with Student's t test for independent non-paired samples.

Example 6

Anti-HBV Assay

The anti-HBV activity of the compounds was determined by treating the AD-38 cell line carrying wild type HBV under the control of tetracycline (see Ladner S. K., Otto M. J., Barker C. S., Zaifert K., Wang G. H., Guo J. T., Seeger C. & King R. W. Antimicrob. Agents Chemother. 1997, 41, 1715-20). Removal of tetracycline from the medium [Tet (−)] results in the production of HBV. The levels of HBV in the culture supernatant fluids from cells treated with the compounds were compared with that of the untreated controls. Control cultures with tetracycline [Tet (+)] were also maintained to determine the basal levels of HBV expression. 3TC was included as positive control.

The median effective concentrations ($EC_{50}$) ranges of several of the compounds described herein against HBV are shown in Table 3:
A=1-9 μM
B=0.1-0.9 μM
C=0.01-0.09 μM
D=0.001-0.009 μM
E=0.0001-0.0009 μM

TABLE 3

| | Anti-HBV activity | |
|---|---|---|
| | $EC_{50}$ | $EC_{90}$ |
| 7a | D | C |
| 17 | B | A |
| 13 | B | B |
| 8 | D | C |
| 36 | B | A |
| 13 | B | A |
| 20 | B | B |
| 31 | C | A |
| 27 | C | A |
| 28 | C | A |
| 29 | B | A |
| 30 | A | A |
| 25 | C | A |
| 26 | B | A |
| 32 | A | A |
| 7b | C | B |
| 38 | D | B |
| 43 | C | B |
| 44 | B | A |
| 45 | B | A |
| 46 | B | A |
| 47 | C | B |
| 48 | D | C |
| 52 | C | B |
| 54 | A | |
| 55 | B | A |
| 56 | >A | |
| 57 | >A | |
| 58 | C | B |
| 59 | A | |
| 60 | B | B |
| 61 | B | B |
| 62 | A | A |
| 63 | B | A |
| 64 | E | D |
| 65 | C | B |
| 66 | D | C |
| 69 | D | C |
| 72 | B | B |
| 75 | D | C |
| 78 | D | C |

TABLE 3-continued

| | Anti-HBV activity | |
|---|---|---|
| | $EC_{50}$ | $EC_{90}$ |
| 81 | D | B |
| 82 | A | |
| 83 | A | |
| 3TC | B | A |

Example 7

Production of secreted HBeAg is predominantly cccDNA-dependent in HepAD38 cells and therefore can serve as a surrogate marker for cccDNA (Ladner, S. K., Otto, M. J., Barker, C. S., Zaifert, K., Wang, G. H., Guo, J. T., Seeger, C., King, R. W. Antimicrob Agents Chemother 1997, 41, 1715-1720; Zhou T, Guo H, Guo J T, Cuconati A, Mehta A, Block™. Antiviral Res. 2006; 72 (2): 116-24.). The effect on the levels of cccDNA formation was assessed using a cell-based assay that measures HBV e antigen (HBeAg) as a cccDNA-dependent marker in the HepAD38 system. HepAD38 cells were seeded at 50,000 cells/well in collagen-coated 96-well plates with DMEM/F12 medium (Life Technologies) supplemented with 10% heat-inactivated fetal bovine serum. Cells were treated with 0.3 μg/ml tetracycline as needed. Test compounds and controls were added to cells to a final concentration of 10 μM or in a dose response manner ranging from 0.001 to 10 μM. Medium and test compounds were replenished every 5 days in culture. Supernatants were harvested at day-14, clarified by centrifugation at 5000 rpm for 5 min, and stored at −70° C. until use. ELISA—Culture medium was diluted 1:15 in DMEM/F12 and the levels of HBeAg secreted in the culture medium were measured by using HBeAg ELISA kit (BioChain Institute Inc. Hayward, Calif.) according to the manufacturer's protocol. The concentration of compound that reduced levels of secreted HBeAg by 50% ($EC_{50}$) was determined by linear regression.

TABLE 4

| | Anti-HBeAg activity (μM) | |
|---|---|---|
| Compound | $EC_{50}$ | $EC_{90}$ |
| 7a | 0.008 | 0.58 |
| 13 | <10 (86%) | ND |

Example 8

Interestingly, some of the compounds synthesized and found active against HBV in vitro were also unexpectedly active against West Nile Virus (WNV). WNV is a mosquito-borne zoonotic arbovirus belonging to the genus Flavivirus in the family Flaviviridae. The genetic material of WNV is a positive-sense, single strand of RNA, which is between 11,000 and 12,000 nucleotides long; these genes encode seven nonstructural proteins and three structural proteins. The RNA strand is held within a nucleocapsid formed from 12-kDa protein blocks; the capsid is contained within a host-derived membrane altered by two viral glycoproteins.

Antiviral Screening Using a Luciferase Reporter Replicon of West Nile Virus (WNV)

Baby hamster kidney (BHK) cells containing a luciferase reporter replicon of WNV (See Shi P Y, Tilgner M, Lo M K.

Virology. 2002; 296 (2): 219-33) were used for high throughput screening. *Renilla* luciferase and blasticitin resistance genes as a selectable marker gene were engineered in the replicon to replace viral structural proteins. Luciferase activities were measured after 48 h of incubation using *Renilla* Luciferase Assay system (Promega).

The susceptibility of West Nile virus to the compounds described herein can also be evaluated using the assay previously described in: Song, G. Y., Paul, V., Choo, H., Morrey, J., Sidwell, R. W., Schinazi, R. F., Chu, C. K. Enantiomeric synthesis of D- and L-cyclopentenyl nucleosides and their antiviral activity against HIV and West Nile virus. J. Med. Chem. 2001, 44, 3985-3993, Example 9

The susceptibility of Yellow fever to the compounds described herein can also be assayed as previously described in: Julander, J. G., Furuta, Y., Shafer, K., Sidwell, R. W. Activity of T-1106 in a Hamster Model of Yellow Fever Virus Infection. *Antimicrob. Agents Chemother.* 2007, 51, 1962-1966.

Example 10

The susceptibility of Dengue to the compounds described herein can be evaluated using the high throughput assay disclosed by Lim et al., A scintillation proximity assay for dengue virus NS5 2'-O-methyltransferase-kinetic and inhibition analyses, Antiviral Research, Volume 80, Issue 3, December 2008, Pages 360-369.

Dengue virus (DENV) NS5 possesses methyltransferase (MTase) activity at its N-terminal amino acid sequence and is responsible for formation of a type 1 cap structure, m7GpppAm2'-O in the viral genomic RNA. Optimal in vitro conditions for DENV2 2'-O-MTase activity can be characterized using purified recombinant protein and a short biotinylated GTP-capped RNA template. Steady-state kinetics parameters derived from initial velocities can be used to establish a robust scintillation proximity assay for compound testing. Pre-incubation studies by Lim et al., Antiviral Research, Volume 80, Issue 3, December 2008, Pages 360-369, showed that MTase-AdoMet and MTase-RNA complexes were equally catalytically competent and the enzyme supports a random bi bi kinetic mechanism. Lim validated the assay with competitive inhibitory agents, S-adenosylhomocysteine and two homologues, sinefungin and dehydrosinefungin. A GTP-binding pocket present at the N-terminal of DENV2 MTase was previously postulated to be the cap-binding site. This assay allows rapid and highly sensitive detection of 2'-O-MTase activity and can be readily adapted for high-throughput screening for inhibitory compounds. It is also suitable for determination of enzymatic activities of a wide variety of RNA capping MTases.

Example 11

Anti-Norovirus Activity

Compounds can exhibit anti-norovirus activity by inhibiting norovirus polymerase and/or helicase, by inhibiting other enzymes needed in the replication cycle, or by other pathways.

There is currently no approved pharmaceutical treatment for Norovirus infection, and this has probably at least in part been due to the lack of availability of a cell culture system. Recently, a replicon system has been developed for the original Norwalk G-I strain (Chang, K. O., et al. (2006) Virology 353:463-473).

Both Norovirus replicons and Hepatitis C replicons require viral helicase, protease, and polymerase to be functional in order for replication of the replicon to occur. Most recently, an in vitro cell culture infectivity assay has been reported utilizing Norovirus genogroup I and II inoculums (Straub, T. M. et al. (2007) Emerg. Infect. Dis. 13(3):396-403). This assay is performed in a rotating-wall bioreactor utilizing small intestinal epithelial cells on microcarrier beads. The infectivity assay can be used to screen entry inhibitors.

Example 12

Anti-Chikungunya Activity

Anti-Chikungunya Activity can be evaluated as outlined in "Anti-Chikungunya Viral Activities of Aplysiatoxin-Related Compounds from the Marine Cyanobacterium *Trichodesmium erythraeum*" Gupta, D. K.; Kaur, P.; Leong, S. T.; Tan, L. T.; Prinsep, M. R.; Chu, J J. H. Mar Drugs. January 2014; 12(1): 115-127; 10.3390/md12010115 and references cited therein.

Example 13

Anti-HCV Activity

The anti-HCV activity of the compounds described herein can be measured, for example, using an HCV replicon assay as described, for example, in Stuyver L et al., Ribonucleoside analogue that blocks replication or bovine viral diarrhea and hepatitis C viruses in culture. Antimicrob. Agents Chemother. 2003, 47, 244-254.

In this assay, Huh 7 Clone B cells containing HCV Replicon RNA can be seeded in a 96-well plate at 5000 cells/well, and the compounds tested at 10 μM in triplicate immediately after seeding. Following five days incubation (37° C., 5% CO2), total cellular RNA can be isolated by using a versaGene RNA purification kit from Gentra. Replicon RNA and an internal control (TaqMan rRNA control reagents, Applied Biosystems) can be amplified in a single step multiplex Real Time RT-PCR Assay. The antiviral effectiveness of the compounds can be calculated by subtracting the threshold RT-PCR cycle of the test compound from the threshold RT-PCR cycle of the no-drug control (ΔCt HCV). A ΔCt of 3.3 equals a 1-log reduction (equal to 90% less starting material) in Replicon RNA levels. The cytotoxicity of the compounds can also be calculated by using the ΔCt rRNA values. 2'-C-Me-C can be used as the positive control. To determine $EC_{90}$ and $IC_{50}$ values, ΔCt: values can first be converted into fraction of starting material and then used to calculate the % inhibition.

To look specifically at whether the compounds inhibit HCV NS5B, one can using an assay such as that described in "A complex network of interactions between S282 and G283 of HCV NS5B and the template strand affect susceptibility to Sofosbuvir and Ribavirin," Kulkarni et al., Antimicrob Agents Chemother. 2016 Jan. 11. pii: AAC.02436-15.

Example 14

Capsid Formation Assay for Use in Monitoring HBV Capsid Assembly

In the absence of compounds which disrupt capsid formation, hepatitis B virus core C-terminally truncated protein (HBV Cp149, protein isolated by reported methods [Zlotnick, A et al; *Biochem* 1996, 35, 7412-7421] normally assembles into an HBV Cp149 capsid. The purpose of this example was to determine whether putative active agents would disrupt capsid formation, and thus be active as anti-HBV agents. Putative active agents were incubated at a concentration of 25 μM for 1 h at 4° C. with HBV Cp149 at a concentration of 10 μM. Capsid assembly was then promoted by adding 300 mM NaCl, and storing the mixture overnight at 4°. Negative-stain electron micrographs were collected using a JEOL JEM-1400 120 kV electron microscope using uranyl acetate as a contrast agent. These images showed whether capsids formed, and if they did form, whether they formed fully-formed hollow spheres, or deformed (i.e., for example, misassembled or incomplete) spheres.

When treated with vehicle, the capsid formation proceed as expected, forming fully-formed hollow spheres with a diameter of approximately 40 nm. When compound GLS4 was added, the capsid formation was disrupted, as shown by the formation of relatively large (around 80-100 nm) misassembled hollow spheres. When Compound 7a was added, the capsid formation was disrupted, as shown by the formation of relatively small (less than around 40 nm) and tightly packed incomplete hollow spheres. The results are shown in FIG. 1.

Figure 2:
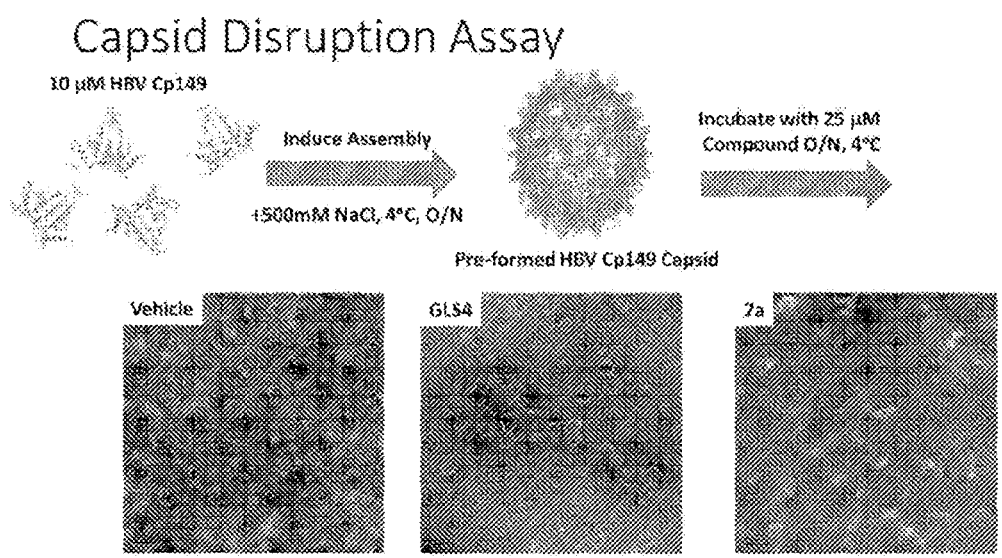
FIG. 2 shows a series of electron micrographs of HBV Cp149 capsids treated with vehicle (showing the capsids in the form of fully-formed hollow spheres), with GLS4, showing that the capsids have formed misassembled hollow spheres, and with Compound 7a, showing that the capsids formed incomplete hollow spheres, in a relatively low abundance.
Figure 3:
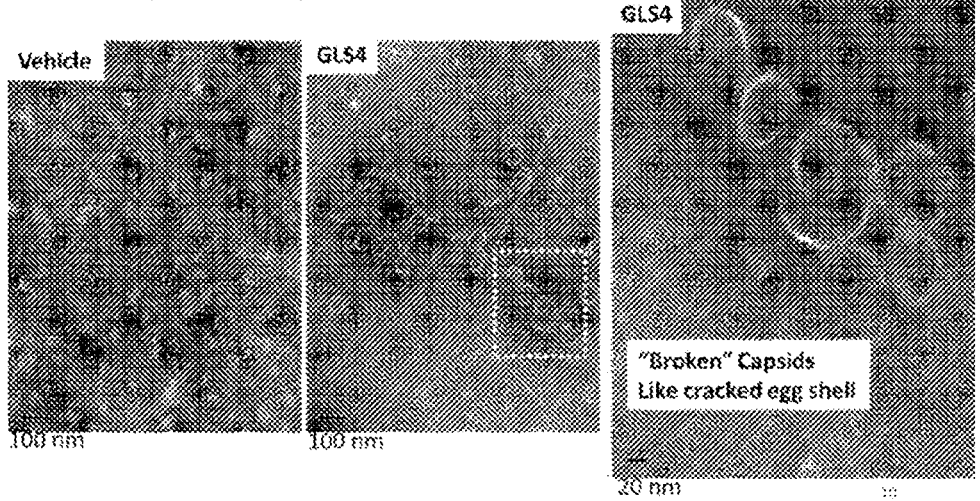
FIG. 3 shows a series of electron micrographs of the capsids shown in FIG. 2, with the first two micrographs repeated, and a third micrograph enlarging the portion of the second micrograph to enhance the view of the damage to the capsids.
Figure 4:
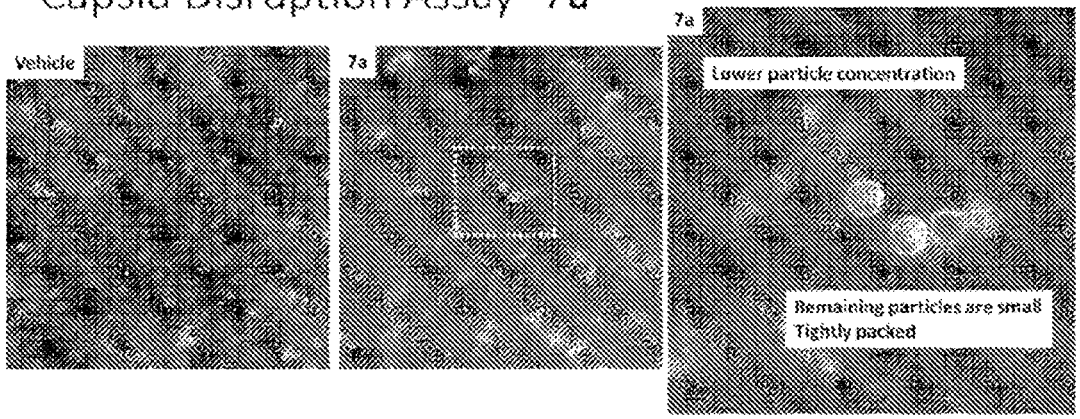
FIG. 4 shows a series of electron micrographs of the capsids shown in FIG. 2, with the first and third micrographs repeated as the first and second micrographs. A third micrograph is shown, enlarging the portion of the second micrograph to enhance the view of the damage to the capsids.

The next question was whether these compounds could disrupt already-formed capsids. Accordingly, the capsids were formed as discussed above (incubation of isolated HBV Cp149 with 300 mM NaCl, stored overnight at 4°). Then, the capsids were incubated with the putative compound (overnight at 4°), and electron micrographs were then taken. FIG. 2 shows electron micrographs of capsids incubated with vehicle, with 25 μM GLS4, and with 25 μM Compound 7a. FIG. 3 shows the results with GLS4, in which the capsids were disrupted. The micrographs show that the capsids were broken, like cracked egg shells. FIG. 4 shows the results with Compound 7a, where the concentration of capsids was clearly, and significantly reduced, and the remaining capsids were relatively small and tightly packed.

Various publications are cited herein, the disclosures of which are incorporated by reference in their entireties for all purposes.

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

We claim:

1. A compound of the following formula:

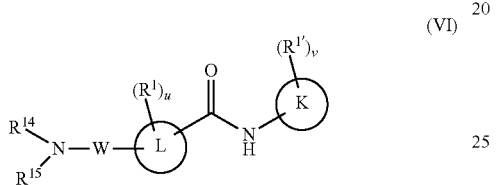

or a pharmaceutically acceptable salt thereof, wherein
when $R^1$ and $R^{1'}$ are attached to a carbon, they are, independently, hydrogen, halogen, $SF_5$, $CF_3$, hydroxy, $N(R')S(O)_2R'$, $S(O)_2R'$, $S(O)_2N(R')_2$, $C_{1-6}$ alkoxy, $C_{1-6}$ haloalkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl;

when $R^1$ and $R^{1'}$ are attached to a nitrogen, they are, independently, hydrogen, $C_{2-6}$ alkoxy, $C_{3-6}$ alkoxyalkyl, $C_{2-6}$ alkenyl, alkoxycarbonyl, carbonylalkyl, carbonyl aryl, $C_{1-6}$ alkyl, heterocyclylalkyl, $C_{2-6}$ hydroxyalkyl, or $S(O)_2R'$;

each R' is independently H, $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl, or if two R' reside on the same nitrogen atom, they can come together to form a $C_{3-6}$ ring optionally containing a N, O, or S heteroatom;

the R' groups, other than H, can optionally be substituted with one or more substituents, which substituents are, independently, halo, $C_{1-6}$ haloalkyl, $C_{1-6}$ hydroxyalkyl, hydroxyl, carboxyl, acyl, aryl, acyloxy, amino, amido, carboxyl derivatives, alkylamino, dialkylamino, arylamino, alkoxy, alkoxyalkyl, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrazine, carbamate, phosphonic acid, or phosphonate;

u and v are independently 0, 1, 2, 3, 4 or 5;

K is a six-membered heteroaromatic ring containing one, two, or three nitrogen atoms, a five-membered heteroaromatic ring containing one, two, or three heteroatoms which are, independently, N, O, or S; or a $C_{4-14}$ bicyclic ring;

L is a five-membered heteroaromatic ring containing one, two, or three heteroatoms which are, independently, N, O, or S, W is

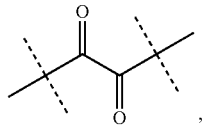

$R^{14}$ is H, $C_{1-6}$ alkyl, $C_{1-6}$ haloalkyl, $C_{2-6}$ alkenyl, or $C_{2-6}$ alkynyl, $R^{15}$ is $C_{1-6}$ alkyl, $C_{1-6}$ haloalkyl, $C_{2-8}$ alkoxyalkyl, a six-membered ring or a six-membered bridged or spiro-fused ring containing zero, one, or two heteroatoms which are, independently, N, O, or S, a seven-membered bridged or spiro-fused ring containing zero, one, or two heteroatoms which are, independently, N, O, S, or Se, a five-membered ring containing zero, one, or two heteroatoms which are, independently, N, O, S or Se; a four-membered ring containing zero, one, or two heteroatoms which are, independently, N, O, S, or Se;

$R^{15}$ is optionally substituted with one or more substituents which are, independently, halogen, $SF_5$, $CF_3$, hydroxy, $N(R')S(O)_2R'$, $S(O)_2R'$, $S(O)_2N(R')_2$, $C_{1-6}$ alkoxy, $C_{1-6}$ haloalkoxy, cyano, azido, $C_{2-6}$ alkynyl, $C_{3-6}$ alkoxyalkyl, alkoxycarbonyl, alkoxycarbonylalkyl, $C_{1-6}$ alkyl, cycloalkyl, arylalkoxycarbonyl, carboxy, $C_{1-6}$ haloalkyl, heterocyclylalkyl, or $C_{1-6}$ hydroxyalkyl; or is optionally substituted with aryl, substituted aryl, heteroaryl, or substituted heteroaryl, where substituents on the substituted aryl and substituted heteroaryl are selected from the group consisting of halogen, $SF_5$, $CF_3$, hydroxy, $N(R')S(O)_2R'$, $S(O)_2R'$, $S(O)_2N(R')_2$, $C(O)R'$, $C_{1-6}$ alkoxy, cyano, azido, $C_{2-6}$ alkynyl, $C_{3-6}$ alkoxyalkyl, alkoxycarbonyl, alkoxycarbonylalkyl, and $C_{1-6}$ alkyl, or $R^{14}$ and $R^{15}$ can come together with the nitrogen to which they are attached form a 6-10 membered bicyclic or bridged ring or a 3 to 8 membered saturated ring; such bicyclic, bridged and saturated ring moiety optionally containing one or more additional heteroatoms which are, independently, O, S or N, and optionally being substituted with one or more substituents each independently selected from the group consisting of halogen, $CF_3$, hydroxy, $N(R')S(O)_2R'$, $S(O)_2R'$, $S(O)_2N(R')_2$, $C_{1-6}$ alkoxy, cyano, azido, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, and $C_{1-6}$ hydroxyalkyl.

2. A pharmaceutical composition comprising a compound of claim 1, or a pharmaceutically acceptable salt thereof, and a pharmaceutically-acceptable carrier.

3. A method for treating a host infected with HBV, comprising administering an effective amount of a compound of claim 1, or a pharmaceutically acceptable salt thereof, to the host in need of treatment thereof.

4. The method of claim 3, wherein the treating a host infected with HBV suppresses HDV infection.

5. The compound of claim 1, wherein $R^{1'}$ is halogen or CN.

6. The compound of claim 1, wherein $R^1$ is methyl.

7. The compound of claim 1, wherein L is an optionally substituted pyrrole.

8. The compound of claim 1, wherein K is optionally substituted pyridyl.

9. The compound of claim 1, wherein $R^{14}$ is $C_{2-6}$ alkenyl or $C_{2-6}$ alkynyl.

\* \* \* \* \*

SEQUENCE LISTING

<160> NUMBER OF SEQ ID NOS: 6

<210> SEQ ID NO 1
<211> LENGTH: 17
<212> TYPE: DNA
<213> ORGANISM: Human

<400> SEQUENCE: 1
tgcccgccat catccta                                                    17

<210> SEQ ID NO 2
<211> LENGTH: 21
<212> TYPE: DNA
<213> ORGANISM: Human

<400> SEQUENCE: 2
tcctcatcgc cctcccatcc c                                               21

<210> SEQ ID NO 3
<211> LENGTH: 23
<212> TYPE: DNA
<213> ORGANISM: Human

<400> SEQUENCE: 3
cgtctgttat gtaaaggatg cgt                                             23

<210> SEQ ID NO 4
<211> LENGTH: 17
<212> TYPE: DNA
<213> ORGANISM: Human

<400> SEQUENCE: 4
gcgcggctac agcttca                                                    17

<210> SEQ ID NO 5
<211> LENGTH: 18
<212> TYPE: DNA
<213> ORGANISM: Human

```
<400> SEQUENCE: 5
caccacggcc gagcggga                                                    18

<210> SEQ ID NO 6
<211> LENGTH: 22
<212> TYPE: DNA
<213> ORGANISM: Human

<400> SEQUENCE: 6
tctccttaat gtcacgcacg at                                               22
```